US009522949B2

(12) United States Patent
Fang et al.

(10) Patent No.: US 9,522,949 B2
(45) Date of Patent: Dec. 20, 2016

(54) FUSION PROTEIN FOR ANTAGONIZING ANGIOGENESIS INDUCIBLE FACTORS AND USES THEREOF

(71) Applicant: YANTAI RC BIOTECHNOLOGIES, Shadong Province (CN)

(72) Inventors: Jianmin Fang, Yantai (CN); Dong Li, Yantai (CN)

(73) Assignee: YANTAI RC BIOTECHNOLOGIES, LTD., Yantai (CN)

( * ) Notice: Subject to any disclaimer, the term of this patent is extended or adjusted under 35 U.S.C. 154(b) by 21 days.

(21) Appl. No.: 13/842,667

(22) Filed: Mar. 15, 2013

(65) Prior Publication Data

US 2013/0190235 A1 Jul. 25, 2013

Related U.S. Application Data

(63) Continuation-in-part of application No. PCT/CN2012/075700, filed on May 18, 2012.

(30) Foreign Application Priority Data

May 20, 2011 (CN) .......................... 2011 1 0131029

(51) Int. Cl.

| | |
|---|---|
| ***C07K 14/705*** | (2006.01) |
| ***C07K 19/00*** | (2006.01) |
| ***A61K 38/16*** | (2006.01) |
| ***A61K 38/17*** | (2006.01) |
| ***C07K 14/71*** | (2006.01) |
| *A61K 38/00* | (2006.01) |

(52) U.S. Cl.

CPC ............... *C07K 14/71* (2013.01); *A61K 38/00* (2013.01); *A61K 38/177* (2013.01); *A61K 38/179* (2013.01); *C07K 14/705* (2013.01); *C07K 2319/00* (2013.01); *C07K 2319/30* (2013.01); *C07K 2319/32* (2013.01)

(58) Field of Classification Search

CPC .... A61K 2300/00; A61K 38/00; A61K 38/16; A61K 2039/70; A61K 38/177; A61K 38/1793; A61K 38/18; C07K 2319/00; C07K 14/71; C07K 14/47; C07K 14/00; C07K 14/705; C07H 21/00

See application file for complete search history.

(56) References Cited

U.S. PATENT DOCUMENTS

2006/0234347 A1* 10/2006 Harding et al. ............. 435/69.1

FOREIGN PATENT DOCUMENTS

WO WO-2006113277 A2 * 10/2006

OTHER PUBLICATIONS

Skolnick et al. From genes to protein structure and function: novel applications of computational approaches in the genomic era. Trends in Biotech 18(1): 34-39, 2000.*

Bork, A. Powers and pitfalls in sequence analysis: the 70% hurdle. Genome Res 10: 398-400, 2000.*

Doerks et al. Protein annotation: detective work for function prediction. Trends in Genetics 14(6): 248-250, 1998.*

Smith et al. The challenges of genome sequence annotation or "The devil is in the details". Nature Biotech 15: 1222-1223, 1997.*

Brenner, S.E. Errors in genome function. Trends in Genetics 15(4): 132-133, 1999.*

Bork et al. Go hunting in sequence databases but watch out for the traps. Trends in Genetics. 12(10): 425-427, 1996.*

Wells. J.A. Additivity of mutational effects in proteins. Biochemistry 29 (37): 8509-8517, 1990.*

Ngo et al. Computational complexity, protein structure prediction, and the Levinthal paradox. The Protein Folding Problem and Tertiary Structure Prediction, pp. 492-495, 1994.*

Phillips, A., The challenge of gene therapy and DNA delivery. J Pharm Pharmacology 53: 1169-1174, 2001.*

Rubanyi, G.M. The future of human gene therapy. Mol Aspects Med 22: 113-142, 2001.*

Juengst, E.T. What next for human gene therapy? BMJ 326: 1410-1411, 2003.*

Holash et al. VEGF-Trap: A VEGF blocker with potent antitumor effects. Proc Natl Acad Sci USA 99(17): 11393-11398, 2002.*

Shinkai et al. Mapping of the sites involved in ligand association and dissociation at the extracellular domain of the kinase insert domain-containing receptor for vascular endothelial growth factor. J Biol Chem 273(47): 31283-31288, 1998.*

Barleon et al. Mapping of the sites for ligand binding and receptor dimerization at the extracellular domain of the vascular endothelial growth factor receptor FLT-1. J Biol Chem 272(6): 10382-10388, 1997.*

Tokuriki et al. Stability effects of mutations and protein evolvability. Curr Opin Structural Biol 19: 596-604, 2009.*

Casanovas, O. et al., "Drug resistance by evasion of antiangiogenic targeting of VEGF signaling in late-stage pancreatic islet tumors," *Cancer Cell,* 2005, vol. 8, No. 4 p. 299-309.

Dorrell, M. et al., "Combination angiostatic therapy completely inhibits ocular and tumor angiogenesis," *Proceedings of the National Academy of Sciences,* 2007, vol. 104, No. 3, p. 967-972.

Ferrera, N. et al., "The biology of VEGF and its receptors," *Nature Medicine,* 2003, vol. 9, p. 669-676.

Ferrera, N., "Vascular Endothelial Growth Factor as a Target for Anticancer Therapy," *Oncologist,* 2004, vol. 1, p. 2-10.

Hanahan, D. et al., "Patterns and Emerging Mechanisms of the Angiogenic Switch during Tumorigenesis," *Cell,* 1996, vol. 86, p. 353-364.

Hanahan, D. et al., "The Hallmarks of Cancer," *Cell,* 2000, vol. 100, No. 1, p. 57-70.

Hsu, J. et al., "Monoclonal Antibodies Targeting Vascular Endothelial Growth Factor," *Biodrugs,* 2009, vol. 23, No. 5, p. 289-304.

Hurwitz, H. et al., "Bevacizumab plus Irinotecan, Fluorouracil, and Leucovorin for Metastatic Colorectal Cancer," *The New England Journal of Medicine,* 2004, vol. 350, No. 23, p. 2335-2342.

Jenab-Wolcott, J. et al., "Bevacizumab: current indications and future development for management of solid tumors," *Expert Opinion on Biological Therapy,* 2009, vol. 9, No. 4, p. 507-517.

(Continued)

*Primary Examiner* — Bridget E Bunner

(74) *Attorney, Agent, or Firm* — Saliwanchik, Lloyd & Eisenschenk

(57) ABSTRACT

The present invention relates to angiogenesis-inhibitory fusion proteins and use thereof. Particularly, the present invention provides fusion proteins inhibiting a plurality of angiogenic factors. More particularly, the present invention relates to the fusion proteins of VEGF receptor and FGF receptor and their applications in the treatment of angiogenesis related diseases.

18 Claims, 10 Drawing Sheets

(56) References Cited

OTHER PUBLICATIONS

Krupitskaya, Y. et al., "Ramucirumab, a fully human mAb to the transmembrane signaling tyrosine kinase VEGFR-2 for the potential treatment of cancer," *Current Opinion in Investigational Drugs,* 2009, vol. 10, No. 6, p. 597-605.

Sandler, A. et al., "Paclitaxel-Carboplatin Alone or with Bevacizumab for Non-Small-Cell Lung Cancer," *The New England Journal of Medicine,* 2006, vol. 355, No. 24, p. 2542-2550.

Summers, J. et al., "FDA Drug Approval Summary: Bevacizumab plus Interferon for Advanced Renal Cell Carcinoma," *Oncologist,* 2010 vol. 15, No. 1, p. 104-111.

Welti, J.C. et al., "Fibroblast growth factor 2 regulates endothelial cell sensitivity to sunitinib," *Oncogene,* 2011, vol. 30, p. 1183-1193.

* cited by examiner concentration of fusion proteins

MWSWKCLLFWAVLVTATLCTARPSPTLPEQAQPWGAPVEVESFLVHPGDLLQLRCRLR
DDVQSINWLRDGVQLAESNRTRITGEEVEVQDSVPADSGLYACVTSSPSGSDTTYFSVN
VSDALPSSEDDDDDDDSSSEEKETDNTKPNPVAPYWTSPEKMEKKLHAVPAAKTVKFK
CPSSGTPNPTLRWLKNGKEFKPDHRIGGYKVRYATWSIIMDSVVPSDKGNYTCIVENEY
GSINHTYQLDVVERSPHRPILQAGLPANKTVALGSNVEFMCKVYSDPQPHIQWLKHIEV
NGSKIGPDNLPYVQILKTAGVNTTDKEMEVLHLRNVSFEDAGEYTCLAGNSIGLSHHSA
WLTVLEALEER (SEQ ID No:77)

FIG. 7A

KLKDPELSLKGTQHIMQAGQTLHLQCRGEAAHKWSLPEMVSKESERLSITKSACGRNG
KQFCSTLTLNTAQANHTGFYSCKYLAVPTSKKKETESAIYIFISDTGRPFVEMYSEIPEIIH
MTEGRELVIPCRVTSPNITVTLKKFPLDTLIPDGKRIIWDSRKGFIISNATYKEIGLLTCEAT
VNGHLYKTNYLTHRQTNTIIDVQISTPRPVKLLRGHTLVLNCTATTPLNTRVQMTWSYP
DEKNKRASVRRRIDQSNSHANIFYSVLTIDKMQNKDKGLYTCRVRSGPSFKSVNTSVHI
YDKAFITVKHRKQQVLETVAGKRSYRLSMKVKAFPSPEVVWLKDGLPATEKSARYLTR
GYSLIIKDVTEEDAGNYTILLSIKQSNVFKNLTATLIVNVKPQIYEKAVSSFPDPALYPLGS
RQILTCTAYGIPQPTIKWFWHPCNHNHSEARCDFCSNNEESFILDADSNMGNRIESITQR
MAIIEGKNKMASTLVVADSRISGIYICIASNKVGTVGRNISFYITDVPNGFHVNLEKMPTE
GEDLKLSCTVNKFLYRDVTWILLRTVNNRTMHYSISKQKMAITKEHSITLNLTIMNVSLQ
DSGTYACRARNVYTGEEILQKKEITIRDQEAPYLLRNLSDHTVAISSSTTLDCHANGVPE
PQITWFKNNHKIQQEPGIILGPGSSTLFIERVTEEDEGVYHCKATNQKGSVESSAYLTVQG
TSDKSNLE (SEQ ID No:78)

FIG. 7B

ASVGLPSVSLDLPRLSIQKDILTIKANTTLQITCRGQRDLDWLWPNNQSGSEQRVEVTEC
SDGLFCKTLTIPKVIGNDTGAYKCFYRETDLASVIYVYVQDYRSPFIASVSDQHGVVYIT
ENKNKTVVIPCLGSISNLNVSLCARYPEKRFVPDGNRISWDSKKGFTIPSYMISYAGMVF
CEAKINDESYQSIMYIVVVVGYRIYDVVLSPSHGIELSVGEKLVLNCTARTELNVGIDFN
WEYPSSKHQHKKLVNRDLKTQSGSEMKKFLSTLTIDGVTRSDQGLYTCAASSGLMTKK
NSTFVRVHEKPFVAFGSGMESLVEATVGERVRIPAKYLGYPPPEIKWYKNGIPLESNHTI
KAGHVLTIMEVSERDTGNYTVILTNPISKEKQSHVVSLVVYVPPQIGEKSLISPVDSYQY
GTTQTLTCTVYAIPPPHHIHWYWQLEEECANEPSQAVSVTNPYPCEEWRSVEDFQGGNK
IEVNKNQFALIEGKNKTVSTLVIQAANVSALYKCEAVNKVGRGERVISFHVTRGPEITLQ
PDMQPTEQESVSLWCTADRSTFENLTWYKLGPQPLPIHVGELPTPVCKNLDTLWKLNAT
MFSNSTNDILIMELKNASLQDQGDYVCLAQDRKTKKRHCVVRQLTVLERVAPTITGNLE
NQTTSIGESIEVSCTASGNPPPQIMWFKDNETLVEDSGIVLKDGNRNLTIRRVRKEDEGL
YTCQACSVLGCAKVEAFFIIEGAQEKTNLE (SEQ ID No:79)

FIG. 7C

FUSION PROTEIN FOR ANTAGONIZING ANGIOGENESIS INDUCIBLE FACTORS AND USES THEREOF

CROSS-REFERENCE TO A RELATED APPLICATION

The present application is a continuation-in-part of International Application PCT/CN2012/075700, filed May 18, 2012; which claims priority to Chinese Application No. 201110131029, filed May 20, 2011; both of which are incorporated by reference herein in their entirety, including any figures, tables, nucleic acid sequences, amino acid sequences, or drawings.

The Sequence Listing for this application is labeled "SeqList-03Mar15.txt" which was created on Mar. 14, 2013Mar. 3, 2015 and is 227 KB. The entire content of the sequence listing is incorporated herein by reference in its entirety.

FIELD OF THE INVENTION

The present invention relates to fusion proteins antagonizing angiogenesis inducing factors and uses thereof. Particularly, the present invention relates to fusion proteins inhibiting a plurality of angiogenic factors and uses thereof. More particularly, the present invention relates to fusion proteins of VEGF receptor and FGF receptor and their applications in the treatment of angiogenesis-related diseases

BACKGROUND OF INVENTION

Angiogenesis is one of the primary factors resulting in the growth and metastasis of malignant tumors [1]. The process of angiogenesis is regulated by many factors, among which some factors promote angiogenesis, while some factors inhibit angiogenesis, and as a result, the regulation of angiogenesis is a very complicated dynamic equilibrium process [2]. Anti-angiogenesis treatment is intended to control the growth of tumor by blocking angiogenic stimulating factors or by using angiogenesis inhibitors.

At present, a large amount of angiogenic stimulating factors are known, such as, for example, vascular endothelial growth factor (VEGF), fibroblast growth factor (FGF), hepatocyte growth factor (HGF), DDR1, EphA1, EphA2, EphA8, EphB1, EphB4, EGFR, HER-2, ErbB3, MET, RON, CSF1R, KIT, PDGFR-A, PDGFR-B, TEK Tie-1, and the like, which stimulate the division and differentiation of vascular endothelial cells and the morphogenesis of blood vessels. Among these factors mentioned above, it is now known that VEGF is the most angiogenesis-specific and the most effective growth factor [3, 4].

In a hypoxic environment inside tumor tissues, VEGFs are secreted by the tumor cells, induce the division and migration of vascular endotheliocytes, and result in the establishment of a tumor vascular network. It has been demonstrated that the inhibition of VEGF may prevent angiogenesis and inhibit the growth of tumor. For this reason, VEGF and its receptors are important targets for anti-angiogenesis medicaments.

At present, anti-angiogenesis medicaments demonstrated in clinical trials to have efficacy include Bevacizumab (under the trade name of Avastin), which is able to block VEGF directly and inhibit the tumor angiogenesis. Bevacizumab was approved for marketing by FDA in 2004, and as a first-line drug for rectal cancer, it is the first marketing-approved drug that plays a role in anticarcinogenesis by inhibiting angiogenesis. Avastin is a humanized anti-VEGF monoclonal antibody, which is produced by Genentech. In a large-scale Phase III clinical trial, the combined therapy by Avastin and chemotherapy may significantly extend the survival time of the patients suffering from various types of cancers, including rectal cancer, lung cancer, breast cancer and renal cancer. [5, 6] The clinical success of Avastin show that the anti-angiogenesis treatment using tumor vascular system as the target is a clinically effective measure and can provide a new path for the tumor treatment.

Besides Avastin, several drugs for anti-VEGF signaling are also in the late phase of human clinical trial, and are expected for clinical application in the next several years. Among others, Aflibercept (also called as VEGF-Trap), developed by the cooperation between Regeneron and Sanofi-Aventis, is now under Phase III clinical trial [7]. Great progress has been achieved in the clinical treatment of tumor using anti-VEGF medicament; however, clinical trials also show that existing anti-VEGF treatment has limitations. From the point of the effect of tumor treatment, Avastin may extend the half survival time of the colon cancer patient for about 3-4 months [9, 10], and extend the half survival time of the breast cancer patient for about 7-8 months [11]; however, Avastin cannot effectively inhibit the growth of tumor blood vessel over long term. The primary causes resulting in the failure of anti-VEGF treatment or the appearance of resistance may depend on the regulation of tumor angiogenesis by a plurality of factors. Although VEGF plays an important role in angiogenesis, it is not the only angiogenesis stimulating factor. Meanwhile, owing to the heterogeneity of tumor cells, the complexity of tumor microenvironment and the compensatory response mechanism of body, when the activity of VEGF is inhibited for a long period of time, other angiogenesis stimulating factors would be expressed [12], and thus the growth of tumor blood vessel is no longer dependent on VEGF signaling path.

The variation of angiogenesis factors expressed by the tumor was studied during anti-VEGFR2 treatment for pancreatic tumor by Hanahan's group, indicating that the expression of several genes changed during anti-VEGF treatment, in which the expression of FGF-2 significantly increased. It has been shown that the expression of FGF, especially FGF-2, increased significantly in the tumor resistant to anti-VEGF treatment so that angiogenesis was activated again and the tumor repopulation was inhibited after blocking FGF signal pathway [13]. It may be seen that the over-expression of FGF-2 is closely related to the ability of tumor to escape from anti-VEGF treatment.

At present, some progress has been made in the aspect of dual- or multi-target antagonism using small molecule medicament, demonstrating that the anti-tumor effect by simultaneous antagonism of VEGF and FGF-2 is better than the single target anti-tumor therapy [14]. However, unexpected side effect may be resulted by small molecule multi-target antagonists due to the lack of specificity, and sometimes, such side effect will be shown only in the late phase of clinical trial, and thus, it is of great risk. While, macromolecule protein medicaments, especially Fc fusion protein and monoclonal antibody, have advantages, which are not possessed by the small molecule medicaments, such as high specificity and long in vivo half-life etc., which make them become the hot area for the research and development of medicament.

Fibroblast growth factor (FGF) is a heparin-binding growth factor family, which has 22 family members in the mammals (FGF 1-14, 16-23). FGF has many important biological functions, such as cell multiplication, differentiation, migration, angiogenesis and tumorigenesis. FGF exerts many biological functions by binding and activating the cell surface FGF receptor (FGFR). (See, for example, Eswarakumar et al. Cytokine Growth Factor Rev. 16: 139-149, 2005). Fibroblast growth factor receptor (FGFR) is the receptor that binds the family members of fibroblast growth factor. A part of fibroblast growth factor receptor is involved in the disease process. In the mammals, there are four FGFR genes: fgfR1-fgfR4. The fibroblast growth factor receptor is composed of extracellular domain, transmembrane domain and intracellular domain.

The family members of FGFR are different from each other in the term of ligand binding properties and kinase domains. However, the extracellular domains thereof are similar. There are three immunoglobulin-like (Ig-like) domains contained in their extracellular domains: the first Ig-like domain, the second Ig-like domain and the third Ig-like domain, and there is also a sequence contained between the first and the second Ig-like domain. Said sequence contained between the first and the second Ig-like domain is referred herein as the intermediate functional sequence region of the Ig-like domain of FGFR. Said intermediate functional sequence region comprises a region of acidic amino acids, referred as acidic box (AB).

No macromolecule fusion protein has been reported so far to be successfully constructed to block both VEGF and FGF. Although a plurality of angiogenesis-inhibitory fusion proteins have already been reported, for example, FGFR-based fusion protein (WO/2008/065543), Notch3-based fusion protein (WO/2010/021729), VEGFR-based fusion protein (WO/2010/105573), LK8-based fusion protein (WO/2008/075833) etc., all these fusion proteins are directed to a single target, and angiogenesis inhibition is realized by the fusion of a part of a single angiogenesis inhibitor and immunoglobulin Fc segment. In the prior art, no fusion protein has been reported to achieve an angiogenesis inhibition effect by inhibiting dual targets through successful fusion of two inhibitory units of blood vessel.

BRIEF SUMMARY

In one aspect, the present invention provides fusion proteins, which comprise at least two angiogenesis-inhibitory units derived from at least two angiogenesis inhibitors. In one embodiment, said fusion protein inhibits angiogenesis. In another embodiment, said fusion protein binds to FGF and VEGF in vivo and/or in vitro.

In one embodiment, the present fusion protein comprises at least two angiogenesis-inhibitory units derived from at least two angiogenesis inhibitors, in which said at least two angiogenesis inhibitors are selected from the group consisting of: VEGFR, for example, VEGFR1, VEGFR2, VEGFR3; and FGFR, for example, FGFR1, FGFR2, FGFR4.

Preferably, the present fusion protein comprises at least two angiogenesis-inhibitory units derived from VEGFR1, VEGFR2 and FGFR1. More preferably, the present fusion protein comprises two angiogenesis-inhibitory units derived from VEGFR1, VEGFR2 and FGFR1, wherein one angiogenesis inhibition unit derived from VEGFR1 and VEGFR2, while the other one derived from FGFR1.

In another embodiment, the present fusion protein comprises at least two angiogenesis-inhibitory units derived from at least two angiogenesis inhibitors, wherein the at least two angiogenesis inhibitors are angiogenesis-inhibitory soluble receptor segment, in which said soluble receptor segment may be selected from the group consisting of: DDR1, EphA1, EphA2, EphA8, EphB1, EphB4, EGFR, HER-2, ErbB3, FGFR1, FGFR2, FGFR4, MET, RON, CSF1R, KIT, PDGFR-A, PDGFR-B, TEK, Tie-1, HGF, VEGFR1, VEGFR2, VEGFR3 and the allelic variants thereof. In one specific embodiment, the angiogenesis inhibitor is selected from angiogenesis-inhibitory receptors VEGFR and FGFR.

In some embodiments, the present fusion protein comprises at least two angiogenesis-inhibitory units derived from at least two (preferably, two or three) angiogenesis inhibitors, wherein the at least two angiogenesis-inhibitory units comprise at least one angiogenesis inhibition unit derived from an extracellular domain of VEGFR and at least one angiogenesis inhibition unit derived from an extracellular domain of FGFR. Preferably, the extracellular domain of VEGFR is a VEGFR1, VEGFR2 and/or VEGFR3 extracellular domain, and the extracellular domain of FGFR is a FGFR1 and/or FGFR2 extracellular domain.

In some other embodiments, the present fusion protein comprises at least two angiogenesis-inhibitory units derived from at least two (preferably, two or three) angiogenesis inhibitors, wherein the at least two angiogenesis-inhibitory units comprise one angiogenesis inhibition unit derived from a VEGFR1 and/or VEGFR2 extracellular domain and one angiogenesis inhibition unit derived from a FGFR1 extracellular domain.

In some other embodiments, the portion derived from VEGFR (such as VEGFR1 and/or VEGFR2) extracellular domain comprises, or consists of, one or more domains selected from: the first Ig-like domain of VEGFR (such as VEGFR1 or VEGFR2) or a moiety thereof, the second Ig-like domain of VEGFR (such as VEGFR1 or VEGFR2) or a moiety thereof, the third Ig-like domain of VEGFR (such as VEGFR1 or VEGFR2) or a moiety thereof, the fourth Ig-like domain of VEGFR (such as VEGFR1 or VEGFR2) or a moiety thereof, the fifth Ig-like domain of VEGFR (such as VEGFR1 or VEGFR2) or a moiety thereof, the sixth Ig-like domain of VEGFR (such as VEGFR1 or VEGFR2) or a moiety thereof, and the seventh Ig-like domain of VEGFR (such as VEGFR1 or VEGFR2) or a moiety thereof.

In some other embodiments, the portion derived from FGFR (such as FGFR1) extracellular domain comprises, or consists of, one or more domains selected from: the first Ig-like domain of FGFR (such as FGFR1) or a moiety thereof, a portion derived from the intermediate functional sequence region of the Ig-like domain of FGFR (such as FGFR1), the second Ig-like domain of FGFR (such as FGFR1) or a moiety thereof, and the third Ig-like domain of FGFR (such as FGFR1) or a moiety thereof.

In some embodiments, the domains and/or segments contained in the present fusion protein may be linked directly and/or indirectly via a linker. In one specific embodiment, the present fusion protein comprises a portion derived from the intermediate functional sequence region of the Ig-like domain of FGFR (such as FGFR1). Preferably, the portion derived from the intermediate functional sequence region of the Ig-like domain of FGFR (such as FGFR1) does not contain any acidic box (AB).

In one specific embodiment, the portion derived from the intermediate functional sequence region comprises, or consists of, a sequence selected from: an amino acid sequence corresponding to the position 134 to the position 162, the position 145 to the position 162, or the position 151 to the position 162 of SEQ ID NO: 1.

In one embodiment, the portion derived from the extracellular domain of VEGFR comprises: the second Ig-like domain of VEGFR1 or VEGFR2 and the third Ig-like domain of VEGFR1 or VEGFR2; the portion derived from FGFR (such as FGFR1) extracellular domain comprises: a portion derived from the intermediate functional sequence region of the Ig-like domain of FGFR, the second Ig-like domain of FGFR, and the third Ig-like domain of FGFR. Preferably, the portion derived from the intermediate functional sequence region of the Ig-like domain of FGFR does not contain any acidic box. In one embodiment, said FGFR is, for example, FGFR1 or FGFR2.

In another embodiment, the portion derived from the extracellular domain of VEGFR comprises: the second Ig-like domain of VEGFR1 and the third Ig-like domain of VEGFR2; the portion derived from the extracellular domain of FGFR comprises: a portion derived from the intermediate functional sequence region of the Ig-like domain of FGFR, the second Ig-like domain of FGFR, and the third Ig-like domain of FGFR. Preferably, the portion derived from the intermediate functional sequence region of the Ig-like domain of FGFR does not contain any acidic box. In one embodiment, said FGFR is, for example, FGFR1 or FGFR2.

In another embodiment, the portion derived from the extracellular domain of VEGFR sequentially comprises, from the N-terminus to the C-terminus, the second Ig-like domain of VEGFR1 and the third Ig-like domain of VEGFR2; the portion derived from the extracellular domain of FGFR sequentially comprises, from the N-terminus to the C-terminus, a portion derived from the intermediate functional sequence region of the Ig-like domain of FGFR, the second Ig-like domain of FGFR, and the third Ig-like domain of FGFR. Preferably, the portion derived from the intermediate functional sequence region of the Ig-like domain of FGFR does not contain any acidic box. In one embodiment, said FGFR is, for example, FGFR1 or FGFR2.

In some specific embodiments, the portion derived from the extracellular domain of VEGFR further comprises the first Ig-like domain of VEGFR1. For example, the first Ig-like domain of VEGFR1 is followed by the second Ig-like domain of VEGFR1. Preferably, the first Ig-like domain of VEGFR1 comprises: the amino acid sequence corresponding to the position 32 to the position 123 of SEQ ID NO: 2, or an amino acid sequence sharing at least 70% identity, preferably at least 80%, 90%, 93%, 95%, 97%, 98% or 99% identity with the amino acid sequence corresponding to the position 32 to the position 123 of SEQ ID NO: 2.

In some other embodiments, the portion derived from FGFR (such as FGFR1) extracellular domain further comprises the first Ig-like domain of FGFR or a moiety thereof. Preferably, the first Ig-like domain of EGFR or a moiety thereof comprises:

the amino acid sequence corresponding to the position 40 to the position 118 of SEQ ID NO: 1, or an amino acid sequence sharing at least 70% identity, preferably at least 80%, 90%, 93%, 95%, 97%, 98% or 99% identity with the sequence corresponding to the position 40 to the position 118 of SEQ ID NO: 1; or the amino acid sequence corresponding to the position 77 to the position 118 of SEQ ID NO: 1, or an amino acid sequence sharing at least 70% identity, preferably at least 80%, 90%, 93%, 95%, 97%, 98% or 99% identity with the amino acid sequence corresponding to the position 77 to the position 118 of SEQ ID NO: 1.

In some preferable embodiments of the invention, the second Ig-like domain of VEGFR1 comprises: the amino acid sequence corresponding to the position 151 to the position 214 of SEQ ID NO: 2, or an amino acid sequence sharing at least 70% identity, preferably at least 80%, 90%, 93%, 95%, 97%, 98% or 99% identity with the amino acid sequence corresponding to the position 151 to the position 214 of SEQ ID NO: 2.

In some other preferable embodiments of the invention, the third Ig-like domain of VEGFR2 comprises: the amino acid sequence corresponding to the position 224 to the position 320 of SEQ ID NO: 3, or an amino acid sequence sharing at least 70% identity, preferably at least 80%, 90%, 93%, 95%, 97%, 98% or 99% identity corresponding to the amino acid sequence of the position 224 to the position 320 of SEQ ID NO: 3.

In some other preferable embodiments of the invention, the second Ig-like domain of FGFR1 comprises: the amino acid sequence corresponding to the position 163 to the position 247 of SEQ ID NO: 1, or an amino acid sequence sharing at least 70% identity, preferably at least 80%, 90%, 93%, 95%, 97%, 98% or 99% identity with the amino acid sequence corresponding to the position 163 to the position 247 of SEQ ID NO: 1.

In still other preferable embodiments of the invention, the third Ig-like domain of FGFR1 comprises: the amino acid sequence corresponding to the position 270 to the position 359 of SEQ ID NO: 1, or an amino acid sequence sharing at least 70% identity, preferably at least 80%, 90%, 93%, 95%, 97%, 98% or 99% identity with the amino acid sequence corresponding to the position 270 to the position 359 of SEQ ID NO: 1.

Preferably, the present fusion protein further comprises a fusion partner, for example, an immunoglobulin Fc region, preferably, a human IgG Fc region, more preferably, a human IgG1 Fc region. In some preferred embodiments, the fusion protein comprises:

the amino acid sequence corresponding to SEQ NO: 7, or an amino acid sequence sharing at least 70% identity, preferably at least 80%, 90%, 93%, 95%, 97%, 98% or 99% identity, with the amino acid sequence of SEQ ID NO: 7; or the amino acid sequence encoded by the nucleotide sequence corresponding to SEQ ID NO: 8, or an amino acid sequence encoded by a nucleotide sequence sharing at least 70% identity, preferably at least 80%, 90%, 93%, 95%, 97%, 98% or 99% identity, with the nucleotide sequence of SEQ ID NO: 8.

In some other embodiments, the present fusion protein further comprises a secretory signal peptide region, for example, VEGFR1 signal peptide region. In preferred embodiments, the secretory signal peptide region comprises the amino acid sequence of corresponding to the position 1 to the position 26 of SEQ ID NO: 2 or the amino acid sequence encoded by the nucleotide sequence of SEQ ID NO: 25.

In another aspect, the present invention provides an Fc fusion protein, said protein comprising:

(1) an amino acid sequence sharing at least 70% identity, preferably at least 80%, 90%, 93%, 95%, 97%, 98% or 99% identity, with an amino acid sequence indicated by any one of SEQ ID NOs: 9-24;

(2) an amino acid sequence encoded by a nucleotide sequence sharing at least 70% identity, preferably at least 80%, 90%, 93%, 95%, 97%, 98% or 99% identity, with a nucleotide sequence indicated by any one of SEQ ID NOs: 26-41; or (3) an amino acid sequence comprising or consisting of any one of SEQ ID NOs: 9-24, or an amino acid sequence encoded by the nucleotide sequence indicated by any one of SEQ ID NOs: 26-41.

In some embodiments of the present invention, the order from the N-terminus to the C-terminus of each part and/or each domain involved in the VEGFR-FGFR-Fc fusion protein may be any order or may be in the order as shown in FIG. 1.

In some embodiments, the VEGFR-FGFR-Fc fusion protein according to the present invention further comprises a signal peptide (SP), preferably a secretory signal peptide, for example, the signal peptide of VEGFR1 that has the amino acid sequence corresponding to the position 1 to the position 26 of SEQ ID NO: 2 or the amino acid sequence encoded by the nucleotide sequence of SEQ ID NO: 25. Preferably, the signal peptide is located at the N-terminus of the fusion protein.

Preferably, the present fusion protein sequentially comprises, from the N-terminus to the C-terminus, a portion derived from the extracellular domain of VEGFR and a portion derived from the extracellular domain of FGFR.

Preferably, in the fusion protein according to the present invention, the immunoglobulin Fc region is a human IgG Fc region, for example, a human IgG1 Fc region. Preferably, the fusion protein comprises:

the amino acid sequence corresponding to SEQ NO: 7, or an amino acid sequence sharing at least 70% identity, preferably at least 80%, 90%, 93%, 95%, 97%, 98% or 99% identity, with the amino acid sequence of SEQ ID NO: 7; or the amino acid sequence encoded by the nucleotide sequence corresponding to SEQ ID NO: 8, or an amino acid sequence encoded by the nucleotide sequence sharing at least 70% identity, preferably at least 80%, 90%, 93%, 95%, 97%, 98% or 99% identity, with the nucleotide sequence of SEQ ID NO: 8.

In one embodiment of the present invention, the immunoglobulin Fc region is located at the C-terminus of the fusion protein.

In some embodiments of the present invention, any order from the N-terminus to the C-terminus of each region and/or each domain involved in the VEGFR-FGFR-Fc fusion protein may be present. In some other embodiments, said order may be as shown in FIG. 1. In some specific embodiments, the VEGFR part and the FGFR part, from the N-terminus to the C-terminus, may be located at the upstream or downstream from each other, respectively. Furthermore, the Fc region may be located at the upstream or downstream of angiogenesis inhibition unit. In one embodiment, the Fc region is located at the C-terminus region of the fusion protein.

In some embodiments, the VEGFR-FGFR-Fc fusion protein of the present invention further comprises one or more intrachain disulfide bonds, and preferably, comprises one or more intrachain disulfide bonds in Ig-like domains.

In one aspect of the present invention, the VEGFR-FGFR-Fc fusion protein may be produced by expressing the present fusion protein in prokaryotic cells or eukaryotic cells, for example, bacterial, fungal (such as yeast) and mammalian cell lines. In particular, the mammalian cell line can be, for example, a CHO cell line. In the aspect of recombination protein expression, the CHO cell is the cell line commonly used in the art. Also, original CHO cells can be modified based on various demands in the large-scale expression, and thereby a series of derived CHO cell lines used for producing recombination proteins can be obtained for special expression purposes, for example, for serum-free culture. These techniques are all known in the art of recombination protein expression.

In another aspect, the domains and/or regions involved in the present fusion protein are linked directly and/or indirectly via a linker. For example, a portion derived from the extracellular domain of VEGFR, a portion derived from the extracellular domain of FGFR and a portion derived from immunoglobulin Fc region can be fused directly or indirectly via a linker. In one embodiment, a portion derived from the extracellular domain of VEGFR, the region derived from the extracellular domain of FGFR and the immunoglobulin Fc region are linked directly. In another embodiment, a portion derived from the extracellular domain of VEGFR, the region derived from the extracellular domain of FGFR and immunoglobulin Fc region are linked via a linker, for example, linked via the $(G4S)_3$ linker.

In another aspect, the present invention provides isolated nucleic acid molecules encoding the fusion protein. Preferably, the nucleic acid molecule comprises a nucleotide sequence of any of SEQ ID NOs: 26-41.

In another aspect, the present invention provides a vector comprising the nucleic acid molecule. In another embodiment, the present invention provides cells, preferably CHO cells, transformed/transfected by a vector of the present invention.

In another aspect, the present invention provides a pharmaceutical composition comprising a fusion protein, nucleic acid molecule, vector, and/or cell of the present invention, and a pharmaceutically acceptable carrier.

The present invention further provides a method for producing a fusion protein for inhibiting angiogenesis, which is accomplished by expressing the present fusion protein in prokaryotic cells or eukaryotic cells, for example, bacterial, fungal (such as yeast) or mammalian cell lines. Preferably, the mammalian cell line can be, for example, a CHO cell line.

In another aspect, the present invention provides a method for inhibiting angiogenesis. In one embodiment, the method comprises administering, to a subject in need of such inhibition, an angiogenesis-inhibiting effective amount of a fusion protein, nucleic acid molecule, vector, cell or pharmaceutical composition. Preferably, the method is carried out in mammals.

In another aspect, the present invention provides a method for the treatment or prevention of tumors in mammals. In one embodiment, the method comprises administering, to a subject in need of prevention or treatment, a therapeutically or preventively effective amount of a fusion protein, nucleic acid molecule, vector, cell or pharmaceutical composition. In a preferred embodiment, the present invention can be used to prevent or treat solid tumors.

In another aspect, the present invention provides a method for the treatment or prevention of ophthalmic angiogenesis related diseases in mammals. In one embodiment, the method comprises administering a therapeutically or preventively effective amount of a fusion protein, nucleic acid molecule, vector, cell, or pharmaceutical composition to a subject in need thereof. Preferably, the present invention can be used to prevent or treat ophthalmic angiogenesis related diseases including, but not limited to, age-related macular degeneration, and diabetic retinopathy.

In another aspect of the present invention, a method for binding FGF and/or VEGF in vitro or in vivo, is provided. In one embodiment, the method comprises contacting FGF and VEGF with a fusion protein of the present invention.

The present invention further relates to use of the fusion protein, the nucleic acid molecule encoding said fusion protein, the vector comprising said nucleic acid molecule, the cell transformed/transfected by said vector or the pharmaceutical composition comprising thereof, in manufacture of a medicament for inhibiting angiogenesis. In addition, the present invention relates to the use of the present fusion protein, the nucleic acid molecule encoding said fusion protein, the vector comprising said nucleic acid molecule, the cell transformed/transfected by said vector or the pharmaceutical composition comprising thereof, in manufacture of a medicament for the treatment or prevention of angiogenesis-related diseases. In one embodiment, the present invention can be used to prevent or treat angiogenesis-related diseases, including, but not limited to, tumors and ophthalmic angiogenesis related diseases.

In the disclosure, only some specific embodiments claimed for protection are illustrated by way of example, in which the technical features described in one or more technical proposals may be combined with any one or more technical proposals, and these technical proposals obtained by combination are also covered in the protection scope of the application, as if these technical proposals obtained by combination were already particularly described in the disclosure.

BRIEF DESCRIPTION OF THE DRAWINGS

FIG. 6 shows the effect of the fusion protein on the HUVEC cell division induced by VEGF or FGF-2 and the relative inhibition rates by the fusion protein.

FIG. 7A shows a part of the sequence of hFGFR1, wherein each Ig-like domain is shown in shaded area sequentially. FIG. 7B shows a part of sequence of hVEGFR1, wherein individual Ig-like domains are shown in shaded areas sequentially and natural linker sequences are present between the individual domains. FIG. 7C shows a part of sequence of hVEGFR2, wherein individual Ig-like domains are shown in shaded area sequentially and natural linking sequences are present between the individual domains.

DETAILED DISCLOSURE

Figure 1:
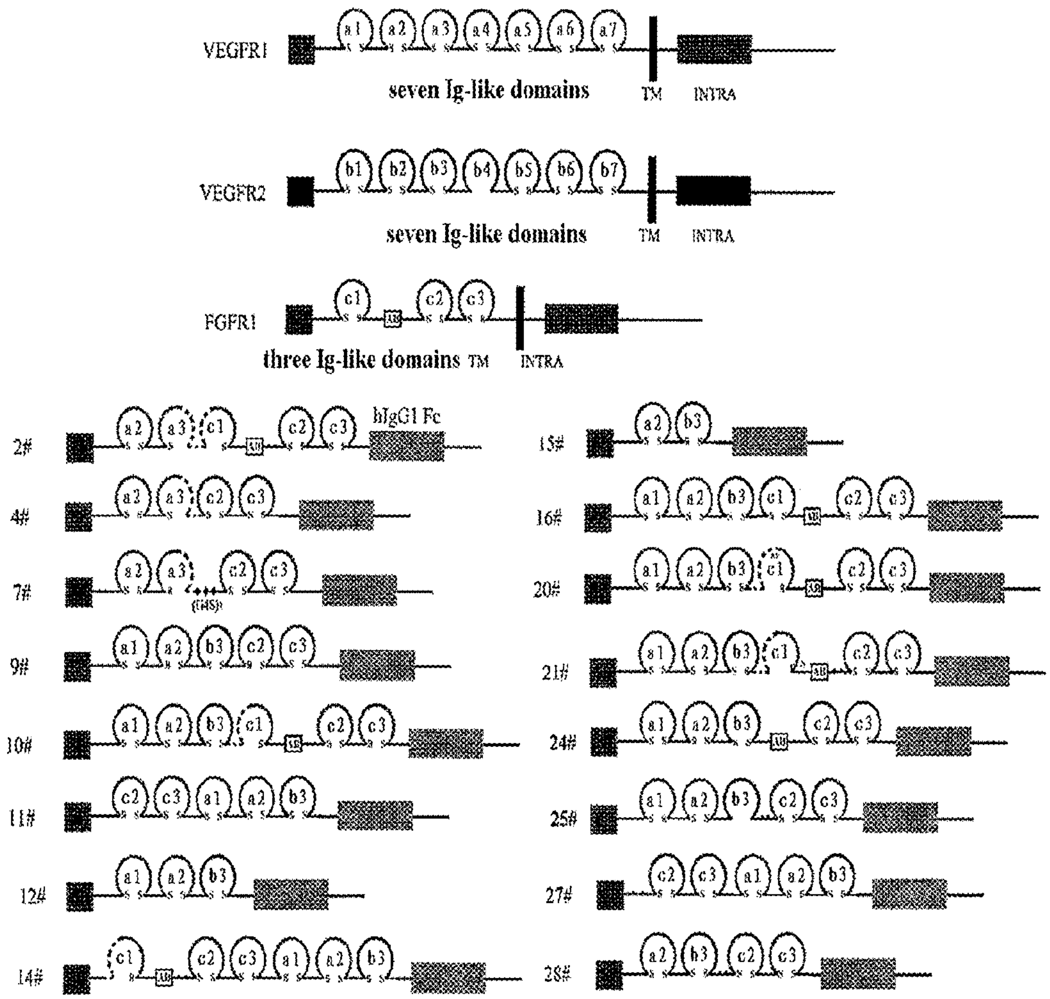
FIG. 1 is a structural representation of a VEGFR-FGFR-Fc fusion protein, in which VEGFR1, VEGFR2 and FGFR1 protein are individually listed. Fc fusion protein is represented by a solid line, and the deleted amino acid is represented by a dashed line; the antibody-like domain is represented by a circle; different antibody-like domains are represented by letter+number, wherein the VEGFR1 domain is represented by a1-a7, the VEGFR2 domain is represented by b1-b7, and the FGFR1 domain is represented by c1-c3; the disulfide bond is represented by s s; human IgG1 Fc is represented by a grey box; the signal peptide is represented by SP; (G4S)3 linking sequence is represented by three diamond boxes; the acidic box sequence is represented by a box with letter AB.

The present invention provides Fc fusion proteins that have high affinity to both vascular endothelial growth factor (VEGF) and fibroblast growth factors (FGF) and can simultaneously antagonize both VEGF and FGF. In one embodiment, the fusion protein of the present invention comprises at least two angiogenesis-inhibitory units derived from at least two angiogenesis inhibitors. In one embodiment, the fusion protein of the present invention comprises human-derived protein sequence.

Advantageously, the VEGF and FGF dual-antagonizing fusion proteins of the present invention can simultaneously block both VEGF and FGF signaling, and can be used for the prevention and treatment of a variety of angiogenesis related diseases.

Definitions

Unless otherwise defined, all scientific terms used herein have the same meaning as commonly understood by those skilled in the art. With regard to the definitions and terms in the art, reference may be made to Current Protocols in Molecular Biology (Ausubel) by the skilled one. Standard three- and/or one-letter code used for expressing one of 20 common L-amino acids in the art are adopted as the abbreviation of amino acid residues.

Although the number ranges and approximate parameter values are given in a broad range in the present invention, all numbers in the specific examples are described as precise as possible. However, certain errors can exist in any numerical values, which may be result from, for example, the standard deviation during measurements. Additionally, all ranges disclosed herein encompass any and all possible sub-ranges contained therein. For example, it should be understood that the range "from 1 to 10" as described herein encompasses any and all possible subranges between the minimum 1 and the maximum 10 (including the endpoints. Additionally, it should be understood that any reference referred as "incorporated herein" is incorporated in its entirety.

Additionally, it should be noted that unless otherwise clearly and explicitly stated, the singular form includes the plural referent, as used in the present invention. The term "or" and the term "and/or" are used interchangeably, unless otherwise clearly indicated in the context.

As used herein, the term "Fc", "Fc region", "Fc fragment" or "immunoglobulin Fc region" refers to the crystallizable fragment of immunoglobulin, and in the present invention, said Fc region is preferably the human IgG1 Fc region.

The term "Fc fusion protein" refers to the antibody-like molecule that incorporates the binding specificity of a heterologous protein and the effector function of a constant region of an immunoglobulin. In the terms of molecular structure, a Fc fusion protein comprises the amino acid sequence having the required binding specificity and the sequence of a constant region of an immunoglobulin. A Fc fusion protein molecule generally comprises a binding site of a receptor or ligand. The sequence of immunoglobulin constant region may be derived from any immunoglobulin, for example, IgG-1, IgG-2, IgG-3 or IgG-4 subtype, IgA (including IgA-1 and IgA-2), IgE, IgD or IgM.

The term "soluble" protein as used herein refers to a protein that may be dissolved in a aqueous solution at a biologically relevant temperature, pH level and osmotic pressure. The "soluble fusion protein" as used herein means that the fusion protein does not contain a transmembrane region or an intracellular region.

As used herein, the term "isolated" refers to a substance and/or entity: (1) which is isolated from at least some components which is present when initially produced (in natural environment and/or in an experiment device) and related thereto and/or (2) which is produced, prepared and/or manufactured artificially. The isolated substance and/or entity may be isolated from at least about 10%, about 20%, about 30%, about 40%, about 50%, about 60%, about 70%, about 80%, about 90%, about 95%, about 98%, about 99%, substantially 100% or 100% other components related to it initially.

The term "part," "segment," or "portion" interchangeably refers to a part of polypeptide, nucleic acid or other molecular constructs.

The term "VEGFR" as used herein refers to vascular endothelial growth factor receptor, which may be VEGFR1, VEGFR2 and/or VEGFR3. Preferably, the VEGFR in the present invention is VEGFR1 and/or VEGFR2, and preferably, is a human VEGFR.

The term "FGFR" as used herein refers to fibroblast growth factor receptor, which may be FGFR1, FGFR2, FGFR3 and/or FGFR4. Preferably, the FGFR in the present invention is FGFR1, and more preferably, is human FGFR1.

The term "Ig-like domain" as used herein refers to immunoglobulin-like domain, which may be found in a plurality of protein families and involved in many biological functions, including cell-cell recognition, cell surface receptor, immune function and the like.

The term "the first Ig-like domain of VEGFR" as used herein refers to the first Ig-like domain in the protein VEGFR from the N-terminus, and preferably, the first Ig-like domain in the protein VEGFR1 from the N-terminus (referred as the first Ig-like domain of VEGFR1 herein) or the first Ig-like domain in the protein VEGFR2 from the N-terminus (referred as the first Ig-like domain of VEGFR2 herein), which has, for example, the amino acid sequence corresponding to the position 32 to the position 123 of SEQ ID NO: 2 or the position 46 to the position 110 of SEQ ID NO: 3. Similarly, the second Ig-like domain of VEGFR has for example the amino acid sequence corresponding to the position 151 to the position 214 of SEQ ID NO: 2 or the position 141 to the position 207 of SEQ ID NO: 3, and the third Ig-like domain of VEGFR has for example the amino acid sequence corresponding to the position 230 to the position 327 of SEQ ID NO: 2 or the position 224 to the position 320 of SEQ ID NO: 3, and the fourth Ig-like domain of VEGFR has for example the amino acid sequence corresponding to the position 335 to the position 421 of SEQ ID NO: 2 or the position 328 to the position 414 of SEQ ID NO: 3, and the fifth Ig-like domain of VEGFR has for example the amino acid sequence corresponding to the position 428 to the position 553 of SEQ ID NO: 2 or the position 421 to the position 548 of SEQ ID NO: 3, and the sixth Ig-like domain of VEGFR has for example the amino acid sequence corresponding to the position 556 to the position 654 of SEQ ID NO: 2 or the position 551 to the position 660 of SEQ ID NO: 3, and the seventh Ig-like domain of VEGFR has for example the amino acid sequence corresponding to the position 661 to the position 747 of SEQ ID NO: 2 or the position 667 to the position 753 of SEQ ID NO: 3. Preferably, the VEGFR may be VEGFR1 or VEGFR2.

As used herein, the term "the first Ig-like domain of FGFR" or "the first Ig-like domain of FGFR1" refers to the first Ig-like domain in the protein FGFR or FGFR1 from the N-terminus, which has for example the amino acid sequence corresponding to the position 40 to the position 118 of SEQ ID NO: 1. Similarly, the term "the second Ig-like domain of FGFR" or "the second Ig-like domain" refers to the second Ig-like domain in the protein FGFR from the N-terminus, which has for example the amino acid sequence corresponding to the position 163 to the position 247 of SEQ ID NO: 1; the term "the third Ig-like domain of FGFR" or "the third Ig-like domain" refers to the first Ig-like domain in the protein EGFR from the N-terminus, which has for example the amino acid sequence corresponding to the position 270 to the position 359 of SEQ ID NO: 1. Preferably, the FGFR is FGFR1, and the first Ig-like domain of FGFR is the first Ig-like domain of FGFR1, and the second Ig-like domain of FGFR is the second Ig-like domain of FGFR1, and the third Ig-like domain of FGFR is the third Ig-like domain of FGFR1.

As used herein, the term "the intermediate functional sequence region of the Ig-like domain of FGFR" or "the intermediate functional sequence region" refers to the sequence between the first Ig-like domain and the second Ig-like domain in the protein FGFR, and preferably, IFS sequence has the amino acid sequence corresponding to the position 118 to the position 162 of SEQ ID NO: 1. Unexpectedly, it has been found by the present inventor that there is a significant effect of the intermediate functional sequence region on the function of the Ig-like domain. The protein FGFR is preferably FGFR1 (SEQ ID NO: 1), especially the protein human FGFR1. The amino acid sequence of the protein human FGFR1 may be found in SEQ ID NO: 1, and its cDNA sequence may be found in SEQ ID NO: 4.

A part of sequence of hFGFR1 is shown in FIG. 7A, in which each Ig-like domain is shown in shaded area sequentially.

In one embodiment, the amino acid sequence of FGFR1 is SEQ ID NO: 1, and its encoding nucleotide sequence is SEQ ID NO: 4.

A part of a sequence of hVEGFR1 is shown in FIG. 7B, in which individual Ig-like domains are shown in shaded areas sequentially and natural linker sequences are present between the individual domains.

In one embodiment, the amino acid sequence of VEGFR1 is SEQ ID NO: 2, and its encoding nucleotide sequence is SEQ ID NO: 5.

A part of a sequence of hVEGFR2 is shown in FIG. 7C, in which individual Ig-like domains are shown in shaded area sequentially and natural linking sequences are present between the individual domains.

In one embodiment, the amino acid sequence of VEGFR2 is SEQ ID NO: 3, and its encoding nucleotide sequence is SEQ ID NO: 6.

As used herein, the term "angiogenesis inhibition unit" refers to a polypeptide section, segment, motif or domain that possesses angiogenesis-inhibiting function. The angiogenesis inhibition unit can refer to any segment of the amino acid sequence in the present fusion protein provided that it possesses the ability for inhibiting angiogenesis. For example, the angiogenesis inhibition unit according to the present invention can include a part derived from the extracellular domain of VEGFR and a part derived from the extracellular domain of FGFR.

As used herein, the term "degenerate variant" refers to the degenerate variant comprises a degenerate change at the third position of the amino acid codon so that the degenerate variant encodes the same amino acid, for example the wobble position of a triplet code comprising one or more changed variants (also referred as synonymous variant).

As used herein, the term "allelic variant" refers to two or more genes present in a particular position of a chromosome.

As used herein, the term "subject" refers to mammals, such as humans. The subject includes other animals, including, but not limited to, domesticated animals (such as dogs and cats), livestocks (such as cattle, sheep, pigs and horses), and experimental animals (such as monkeys, rats, mice, rabbits, and guinea pigs).

As used herein, the term "percentage identity," "homology," or "identity" refers to the sequence identity between two amino acid sequences or nucleic acid sequences. The percentage identity may be determined by alignment between two sequences, and the percentage identity refers to the amount of the same residue (i.e., amino acid or nucleotide) at the same position in the aligned sequences. Sequence alignment and comparison may be performed using standard algorithms in the art (for example Smith and Waterman, 1981, *Adv. Appl. Math.* 2: 482; Needleman and Wunsch, 1970, *J. Mol. Biol.* 48: 443; Pearson and Lipman, 1988, *Proc. Natl. Acad. Sci., USA,* 85: 2444) or by the computerized versions of these algorithms (Wisconsin Genetics Software Package Release 7.0, Genetics Computer Group, 575 Science Drive, Madison, Wis.). Computerized versions that are publicly available include BLAST and FASTA. Additionally, ENTREZ available through National Institutes of Health (Bethesda Md.) may be used for sequence alignment. When BLAST and GAP-BLAST are used, default parameters for each program (for example, BLASTN, available on the website of National Center for Biotechnology Information) may be used. In one embodiment, the percentage identity between two sequences may be determined using GCG with a gap-weight of 1 so that the giving weight of each amino acid gap seems as if it is a single amino acid mismatch between two sequences. Alternatively, ALIGN (version 2.0), which is a part of GCG (Accelrys, San Diego, Calif.) Sequence Alignment Software Package, may be used.

As used herein, the term "hybridization" refers to the process by which a stable double-stranded polynucleotide is formed by non-covalent bonding between two single stranded polynucleotides. The term "hybridization" also may refer to triple-stranded hybridization. The double stranded polynucleotide (generally) produced is the "hybrid" or "duplex". "The condition for hybridization" generally includes a salt concentration lower than about 1 M, and more generally, lower than about 500 mM, and lower than about 200 mM. The hybridization temperature may be as low as 5° C., but it usually higher than about 22° C., and more usually higher than about 30° C., and preferably higher than about 37° C. Hybridization is usually carried out under strict conditions (i.e., the conditions under which the probe will hybridize to its target sequence). Strict hybridization conditions are dependent on the sequence and will be varied under different conditions. Higher hybridization temperature will be probably required by longer segments for specific hybridization. Since the hybridization stringency may be influenced by other factors (including base composition and length of the complementary strand, the presence of organic solvent and the degree of base mismatch), the combination of parameters is more important than the absolute value of any single parameter. Generally, the strict condition is selected as 5° C. lower than the Tm of the sequence under certain ionic strength and pH. Exemplary strict conditions include pH 7.0 to 8.3, sodium ion (or other salts) concentration of at least 0.01 M to no more than 1 M and temperature of at least 25° C. For strict conditions, see, for example Sambrook, Fritsche and Maniatis. "Molecular Cloning A laboratory Manual", 2nd edition, Cold Spring Harbor Press (1989) and Anderson "Nucleic Acid Hybridization", 1st edition, BIOS Scientific Publishers Limited (1999), which are incorporated herein by reference for all purposes mentioned above.

As used herein, the terms "linker," "peptide linker," "linking sequence," and "linker sequence" refer to a short amino acid sequence by which individual domain and/or region involved in the present fusion protein are linked together. The length of the short amino acid sequence is generally 1-20 amino acids, and preferably, 2-10 amino acids.

As used herein, the term of "the amino acid sequence corresponding to SEQ ID NO: N" in a fusion protein or part or domain means that the fusion protein or part or domain has the amino acid sequence substantially as indicated by SEQ ID NO: N, and preferably, containing no more than 1, 2, 3, 4, 5, 10 or 20 substitutions, additions and deletions of amino acids, and yet preferably, said fusion protein or part or domain shares at least 80%, 90%, 93%, 95%, 97%, 98% or 99% identity with the amino acid sequence of SEQ ID NO: N, and more preferably, said fusion protein or part or domain has the amino acid sequence as indicated by SEQ ID NO: N.

As used herein, the term "VEGFR-FGFR-Fc fusion protein" refers to the fusion protein that comprises a portion derived from the extracellular domain of VEGFR, and a portion derived from the extracellular domain of FGFR and the immunoglobulin Fc region. In some embodiments, the portion derived from the extracellular domain of VEGFR and derived from the extracellular domain of FGFR may: (1) has the amino acid sequence as indicated by any one of the positions 1-443 of SEQ ID NO: 9, the positions 1-364 of SEQ ID NO: 10, the positions 1-379 of SEQ ID NO: 11, the positions 1-531 of SEQ ID NO: 12, the positions 1-611 of SEQ ID NO: 13, the positions 1-531 of SEQ ID NO: 14, the positions 1-312 of SEQ ID NO: 15, the positions 1-611 of SEQ ID NO: 16, the positions 1-207 of SEQ ID NO: 17, the positions 1-665 of SEQ ID NO: 18, the positions 1-610 of SEQ ID NO: 19, the positions 1-611 of SEQ ID NO: 20, the positions 1-580 of SEQ ID NO: 21, the positions 1-540 of SEQ ID NO: 22, the positions 1-542 of SEQ ID NO: 23 and the positions 1-435 of SEQ ID NO: 24, or be encoded by a nucleotide sequence as indicated by any one of the positions 1-1326 of SEQ ID NO: 26, the positions 1-1092 of SEQ ID NO: 27, the positions 1-1137 of SEQ ID NO: 28, the positions 1-1593 of SEQ ID NO: 29, the positions 1-1833 of SEQ ID NO: 30, the positions 1-1593 of SEQ ID NO: 31, the positions 1-936 of SEQ ID NO: 32, the positions 1-1833 of SEQ ID NO: 33, the positions 1-621 of SEQ ID NO: 34, the positions 1-1995 of SEQ ID NO: 35, the positions 1-1830 of SEQ ID NO: 36, the positions 1-1833 of SEQ ID NO: 37, the positions 1-1740 of SEQ ID NO: 38, the positions 1-1620 of SEQ ID NO: 39, the positions 1-1626 of SEQ ID NO: 40 and the positions 1-1305 of SEQ ID NO: 41; (2) comprise or consist of the amino acid sequence which shares at least 70% identity, preferably at least 80%, 90%, 93%, 95%, 97%, 98% or 99% identity, with the amino acid sequence as indicated by any one of the positions 1-443 of SEQ ID NO: 9, the positions 1-364 of SEQ ID NO: 10, the positions 1-379 of SEQ ID NO: 11, the positions 1-531 of SEQ ID NO: 12, the positions 1-611 of SEQ ID NO: 13, the positions 1-531 of SEQ ID NO: 14, the positions 1-312 of SEQ ID NO: 15, the positions 1-611 of SEQ ID NO: 16, the positions 1-207 of SEQ ID NO: 17, the positions 1-665 of SEQ ID NO: 18, the positions 1-610 of SEQ ID NO: 19, the positions 1-611 of SEQ ID NO: 20, the positions 1-580 of SEQ ID NO: 21, the positions 1-540 of SEQ ID NO: 22, the positions 1-542 of SEQ ID NO: 23 and the positions 1-435 of SEQ ID NO: 24; or (3) comprise or consist of the amino acid sequence encoded by the nucleotide sequence which shares at least 70% identity, preferably at least 80%, 90%, 93%, 95%, 97%, 98% or 99% identity, with a nucleotide sequence as indicated by any one of the positions 1-1326 of SEQ ID NO: 26, the positions 1-1092 of SEQ ID NO: 27, the positions 1-1137 of SEQ ID NO: 28, the positions 1-1593 of SEQ ID NO: 29, the positions 1-1833 of SEQ ID NO: 30, the positions 1-1593 of SEQ ID NO: 31, the positions 1-936 of SEQ ID NO: 32, the positions 1-1833 of SEQ ID NO: 33, the positions 1-621 of SEQ ID NO: 34, the positions 1-1995 of SEQ ID NO: 35, the positions 1-1830 of SEQ ID NO: 36, the positions 1-1833 of SEQ ID NO: 37, the positions 1-1740 of SEQ ID NO: 38, the positions 1-1620 of SEQ ID NO: 39, the positions 1-1626 of SEQ ID NO: 40 and the positions 1-1305 of SEQ ID NO: 41.

In some preferable embodiments of the invention, the VEGFR-FGFR-Fc fusion protein may: (1) comprise the amino acid sequence as indicated by any one of SEQ ID NOs: 9-24 or be encoded by the nucleotide sequence indicated by any one of SEQ ID NOs: 26-41; (2) comprise or consist of an amino acid sequence that shares at least 70% identity, preferably at least 80%, 90%, 93%, 95%, 97%, 98% or 99% identity, with the amino acid sequence as indicated by any one of SEQ ID NOs: 9-24; or (3) comprise or consist of an amino acid sequence encoded by a nucleotide sequence that shares at least 70% identity, preferably at least 80%, 90%, 93%, 95%, 97%, 98% or 99% identity, with the nucleotide sequence as indicated by any one of SEQ ID NOs: 26-41.

In some preferable embodiments, the VEGFR-FGFR-Fc fusion protein may be encoded by the nucleic acid comprising the sequence of which the complementary sequence is hybridized with the nucleotide sequence as indicated by any one of SEQ ID NOs: 26-41 under stringent conditions, or comprising the degenerative variant of the nucleotide sequence as indicated by any one of SEQ ID NOs: 26-41. In some preferable embodiments, the portion derived from the immunoglobulin Fc region in the VEGFR-FGFR-Fc fusion protein may be encoded by the nucleic acid comprising the sequence of which the complementary sequence is hybridized with the nucleotide sequence indicated by SEQ ID NO: 8 under stringent conditions, or comprising the degenerative variant of the nucleotide sequence indicated by SEQ ID NO: 8.

In other preferable embodiments, the VEGFR-FGFR-Fc fusion protein comprises the VEGFR-FGFR-Fc fusion protein variant, including the variant that has no more than 2, 3, 4, 5, 10, 20, 30 or 50 substitutions, additions or deletions of amino acids in the amino acid sequence as indicated by any one of SEQ ID NOs: 9-24, and preferably, said variant retains angiogenesis-inhibiting ability. In one embodiment, the substitution, addition or deletion is located at a portion derived from the extracellular domain of VEGFR. In another embodiment, the substitution, addition or deletion is located at a portion derived from the extracellular domain of FGFR. In another embodiment, the substitution, addition or deletion is located at a portion derived from immunoglobulin Fc region. In another embodiment, the substitution, addition or deletion is located at the linker or the linking part.

In addition to the naturally occurring modifications in a portion derived from the extracellular domain of FGFR and a portion derived from immunoglobulin Fc region, other post-translational modifications may also be comprised in the VEGFR-FGFR-Fc fusion protein. Such modifications include, but not are limited to, acetylation, carboxylation, glycosylation, phosphorylation, esterification and acylation. As a result, non-amino acid components may exist in the modified VEGFR-FGFR-Fc fusion protein, for example polyethylene glycol, lipid, polysaccharide or monosaccharide, and phosphoric acid. The effect of such non-amino acid components on the function of the VEGFR-FGFR-Fc fusion protein may be tested as described for other VEGFR-FGFR-Fc fusion protein variants herein. When VEGFR-FGFR-Fc fusion protein is produced in a cell, post-translational processing is also possibly important for correct folding and/or protein function. Special cell machines and unique mechanisms exist in different cells (for example CHO, HeLa, MDCK, 293, WI38, NIH-3T3 or HEK293) for these post-translational activities, and different cells may be selected by the skilled artisan to improve modification and processing of VEGFR-FGFR-Fc fusion protein.

The fusion protein as described herein may be produced by any method known in the art. For example, it may be produced by chemical synthesis or from nucleic acid expression. The peptides used in the present invention may be easily prepared according to the established standard liquid, or preferably, solid phase peptide synthesis method known in the art (see, for example J. M. Stewart and J. D. Young, Solid Phase Peptide Synthesis, 2nd edition, Pierce Chemical Company, Rockford, Ill. (1984), in M. Bodanzsky, and A. Bodanzsky, The Practice of Peptide Synthesis, Springer Verlag, New York (1984)). The fusion protein may be produced by the techniques known in the art so that one or more intramolecular crosslinkings may be formed between the cysteine residues located in the polypeptide sequence expected to be comprised in the protein (see, for example U.S. Pat. No. 5,478,925). In addition, general modifications may be performed to the protein described herein by adding, for example, cysteine or biotin to the C-terminus or N-terminus of the protein.

As used herein, "therapeutically effective amount" or "effective amount" refers to a dosage which is sufficient to provide a benefit to whom it is administrated. The administrated dosage, the rate and the time course of administration are dependent on the condition of the patient and the severity of the disease. Finally, the physician is responsible for the prescription (for example decision on the dosage etc.) and will make a decision for the treatment, usually by considering the disease treated, individual condition of the patient, the position of delivery, the method for administration and other factors known to the physician.

In one aspect of the present invention, a fusion protein for inhibiting angiogenesis is provided, which comprises angiogenesis-inhibitory units derived from at least two angiogenesis inhibitors. Preferably, the at least two angiogenesis inhibitors are angiogenesis-inhibitory receptor, and said receptor may, for example, be selected from the group consisting of: DDR1, EphA1, EphA2, EphA8, EphB1, EphB4, EGFR, HER-2, ErbB3, FGFR1, FGFR2, FGFR4, MET, RON, CSF1R, KIT, PDGFR-A, PDGFR-B, TEK, Tie-1, HGF, VEGFR1, VEGFR2, VEGFR3, Notch receptor, LK8, angiostatin, endostatin, plasminogen, collagen XVIII and allelic variants thereof. In one specific embodiment, said angiogenesis inhibitor is angiogenesis-inhibitory receptor VEGFR and FGFR.

Particularly, a series of VEGFR-FGFR-Fc fusion proteins have been constructed according to the present invention, which may bind VEGF and FGF with high affinity and effectively inhibit the cell division induced by VEGF and FGF.

In some embodiments, it is surprisingly found that a fusion protein, which from the N-terminus to the C-terminus sequentially comprises a part derived from the extracellular domain of VEGFR and a part derived from the extracellular domain of FGFR, has excellent VEGF and FGF binding properties, and preferably said part derived from the extracellular domain of VEGFR comprises the first Ig-like domain of VEGFR1, the second Ig-like domain of VEGFR1 and the third Ig-like domain of VEGFR2, and more preferably, said part derived from the extracellular domain of FGFR comprises a portion derived from the intermediate functional sequence region of the Ig-like domain of FGFR1, and the second Ig-like domain of FGFR1 and the third Ig-like domain of FGFR1. More preferably, a portion derived from the intermediate functional sequence region of the Ig-like domain of FGFR1 comprises no acidic box, and more preferably, it has the amino acid sequence corresponding to the position 134 to the position 162, the position 145 to the position 162 or the position 151 to the position 162 of SEQ ID NO: 1.

In some embodiments, the present invention includes the use of (i) VEGFR-FGFR-Fc fusion protein, or (ii) the polynucleotide encoding such fusion protein, in the preparation of the compositions or medicaments for the treatment of diseases mediated by or related to angiogenesis. For example, in one embodiment, the present invention includes the use of (i) VEGFR-FGFR-Fc fusion protein, or (ii) the polynucleotide encoding such fusion protein in the preparation of the medicaments as an angiogenesis inhibitor.

In some embodiments, the VEGFR-FGFR-Fc fusion protein according to the present invention may be produced by the expression of the nucleic acid as indicated by any one of SEQ ID NOs: 26-41 in a mammalian cell line. The mammalian cell line can be, for example, a CHO cell line.

Additionally, in the present invention, the VEGFR-FGFR-Fc fusion protein as described below is also provided, in which a portion derived from the extracellular domain of VEGFR, a portion derived from the extracellular domain of FGFR and a portion derived from immunoglobulin Fc region are linked directly or indirectly via a linker.

In some other embodiments, the present invention includes the isolated nucleic acid molecules encoding the VEGFR-FGFR-Fc fusion protein, and the present invention also includes use of these molecules in manufacture of a medicament. The nucleic acid may be recombinant, synthetic or produced by any available methods in the art, and the methods include cloning by means of using a standard technique.

In some other embodiments, the present invention includes a vector comprising the isolated nucleic acid molecule of the present invention. The vector may be an expression vector, in which the nucleic acid is effectively linked to a control sequence that is able to facilitate the expression of the nucleic acid in a host cell. A plurality of vectors may be used. For example, suitable vectors may include virus (for example poxvirus, adenovirus, baculovirus and the like); or yeast vectors, bacteriophages, chromosomes, artificial chromosomes, plasmids, and cosmids.

In some embodiments, the present invention further includes the cells transfected by these vectors so that the VEGFR-FGFR-Fc fusion protein is expressed. The host cell suitable for the present invention may be prokaryotic cell or eukaryotic cell. They include bacteria, for example *E. coli*, yeast, insect cells and mammalian cells. The mammalian cell lines that may be used include, but are not limited to, Chinese Hamster Ovary (CHO) cells, baby hamster kidney cells, NS0 mouse myeloma cells, monkey and human cell lines, and derivate cell lines thereof, and the like.

In another aspect of the present invention, a method for angiogenesis inhibition is provided, comprising administering the VEGFR-FGFR-Fc fusion protein of the present invention to the subject in need thereof. Preferably, the method is carried out in the mammals.

In another aspect of the present invention, a method for the treatment and prevention of tumors in the mammals is provided, comprising administering, to a subject in need of such treatment or prevention, a VEGFR-FGFR-Fc fusion protein of the present invention. Preferably, the tumor is a solid tumor.

In another aspect, the present invention provides a method for the treatment and prevention of ophthalmic angiogenesis related diseases in the mammals, comprising administering, to a subject in need of such treatment or prevention, a therapeutically effective amount of a VEGFR-FGFR-Fc fusion protein of the present invention. Preferably, the ophthalmic angiogenesis related disease is age-related macular degeneration or diabetic retinopathy.

The present invention also provides the use of VEGFR-FGFR-Fc fusion protein in the preparation of medicaments for angiogenesis inhibition. Additionally, the present invention also relates to the use of VEGFR-FGFR-Fc fusion protein in the preparation of medicaments for the treatment or prevention of angiogenesis-related diseases, and preferably, angiogenesis-related diseases are tumors or ophthalmic angiogenesis related disease.

The angiogenesis-related diseases include, but are not limited to, angiogenesis-dependent cancers, including, for example, solid tumors, hematogenic tumors (for example leukemia) and tumor metastasis; benign tumors, for example, angioma, acoustic neuroma, neurofibroma, trachoma and pyogenic granuloma; rheumatoid arthritis; psoriasis; rubeosis; Osler-Webber Syndrome; myocardial angiogenesis; plaque neovascularization; telangiectasia; hemophiliac joint and angiofibroma.

In some embodiments of the methods described, one or more VEGFR-FGFR-Fc fusion proteins may be administrated together (simultaneously) or at a different time (sequentially). Additionally, the fusion protein may be administrated together with one or more medicaments used for cancer treatment or angiogenesis inhibition.

In some embodiments, the method disclosed in the present invention may be used alone. Alternatively, the subject method may be combined with other conventional anticancer therapies for the treatment or prevention of proliferative diseases (for example tumors). For example, these methods may be used for the prevention of cancers, the prevention of cancer relapse and postoperative metastasis, and may be used as a supplement for other cancer therapies. The effectiveness of conventional cancer therapies (for example, chemotherapy, radiotherapy, phototherapy, immunotherapy and operation) may be enhanced by using target polypeptide therapeutic agents.

In ophthalmology, angiogenesis is related to, for example, diabetic retinopathy, retinopathy of prematurity, age-related macular degeneration, corneal transplantation rejection, neovascular glaucoma and RLF (retrolental fibroplasia). The VEGFR-FGFR-Fc fusion protein disclosed herein may be administrated inside the eye or by other routes. Diseases related to angiogenesis in ophthalmology include, but are not limited to, epidemic keratoconjunctivitis, Vitamin A deficiency, contact lens overwear, atopic keratitis, superior limbic keratitis, pterygium keratitis sicca, sjogren, acne rosacea, phlyctenosis, syphilis, *Mycobacteria* infection, lipid degeneration, chemical burn, bacterial ulcer, fungal ulcer, Herpes simplex infection, Herpes zoster infection, protozoan infection, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy and corneal graph rejection, sickle cell anemia, sarcoid, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infection resulting in retinitis or choroiditis, presumed ocular histoplasmosis, Bests disease, myopia, optic pit, Stargarts disease, pars planitis, chronic retinal detachment, hyperviscosity syndromes, toxoplasmosis, trauma and post-laser complication. Other diseases include, but not limited to, rubeosis (neovasculariation of the angle) related diseases and diseases induced by abnormal hyperplasia of the fibrous blood vessel or fibrous tissue, including all kinds of proliferative vitreoretinopathy.

Administration

The fusion protein of the present invention may be administrated alone, but preferably, as a pharmaceutical composition which usually comprises a suitable pharmaceutical excipient, diluent or carrier selected according to the intended administration route. The fusion protein may be administrated to the patient in need thereof by any suitable route. A precise dosage will be dependent on many factors, including exact properties of the fusion protein.

Some suitable administration routes include (but are not limited to) oral, rectal, nasal, topical (including buccal and sublingual), subcutaneous, vaginal or parenteral (including subcutaneous, intramuscular, intravenous, intracutaneous, intrathecal and extradural) administration.

For intravenous injection and injection at the focal site, active ingredients are present as a parenterally-acceptable aqueous solution, which is free of pyrogen and has appropriate pH value, isotonicity and stability.

The fusion protein may be formulated by the skilled one in the art with appropriate solvent or formulation, for example, isotonic excipients such as sodium chloride injection, Ringer's injection, Ringer's lactate injection. As required, preservative, stabilizer, buffering agent, antioxidant and/or some other additives may be added. The pharmaceutical composition orally administrated may be in a form of tablet, capsule, powder or oral liquid and the like. Solid carrier, such as gelatin or adjuvant, may be comprised in a tablet. Liquid pharmaceutical composition usually comprises liquid carrier, such as water, petroleum, animal or vegetable oil, mineral oil or synthetic oil. Also included may be normal saline solution, glucose or other sugar solutions or glycols such as ethylene glycol, propylene glycol or polyethylene glycol.

Examples of the techniques and schemes as mentioned above and other techniques and schemes as used according to the present invention may be found in Remington's Pharmaceutical Sciences, 16th edition, Oslo, A. (ed), 1980.

Cloning of the Fusion Protein and Construction of the Expression Plasmid

The VEGF receptor and FGF receptor fragment can be obtained from the amplification of the cDNA template of a corresponding receptor through PCR. The IgG1 Fc fragment can be obtained from the cDNA amplification of the human-derived IgG1 through PCR. When PCR primers are designed, linking sequences can be introduced between different fragments so that these different fragments may be finally linked by overlap PCR to form reading frames for different fusion proteins, and endonuclease BspE I and Pst I sites can be added to both ends of the cDNA. The cDNAs for different fusion proteins may be cloned to the expression plasmid after digestion by BspE I and Pst I. The plasmid after cloning may be determined by endonuclease digestion, electrophoresis and finally DNA sequencing.

In the present invention, 2#, 4#, 7#, 9#, 10#, 11#, 12#, 14#, 15#, 16#, 20#, 21#, 24#, 25#, 27# and 28# recombinant expression plasmid are constructed.

2#, 4# and 7# fusion proteins comprise a part of the extracellular domain of VEGFR1, a part of the extracellular domain of FGFR1 and IgG1 Fc; 9#, 10#, 16#, 20#, 21#, 24#, 25# and 28# fusion proteins comprise a part of the extracellular domain of VEGFR1, a part of the extracellular domain of VEGFR2, a part of the extracellular domain of FGFR1 and IgG1 Fc, and the same downstream primer of the extracellular domain of FGFR1 is used for these 11 recombinant expression plasmids above (2#-FGFR1 downstream primer: GTTTTGTCCTCCAGGTACAGGGGCGAGGTC) (SEQ ID NO:42), IgG1 Fc upstream primer (CTGTACCTGGAGGACAAAACTCACACATGC) (SEQ ID NO:43) (and IgG1 Fc downstream primer (GATATCTGCAGTCATTTACCCGGAGACAGG) (SEQ ID NO:44)

The primers of the rest of the fusion proteins are listed as follows:

2# fusion protein:

2#-VEGFR1 upstream primer:
(SEQ ID NO: 45)
ATAGTTCCGGAGGTAGACCATTCGTAGAGATG

2#-VEGFR1 downstream primer:
(SEQ ID NO: 46)
CCTGTGATGCGGGTGCGATTTTTTTCATCAGGGTAACTCC 2#-FGFR1 upstream primer:
(SEQ ID NO: 47)
CTGATGAAAAAAATCGCACCCGCATCACAG 4# fusion protein:

4# VEGFR1 upstream primer is the same as 2#: 2#-VEGFR1 upstream primer

4#-VEGFR1 downstream primer:
(SEQ ID NO: 48)
TTTTTCATCAGGGTAACTCCAGGTCATTTG

4# FGFR1 upstream primer:
(SEQ ID NO: 49)
GGAGTTACCCTGATGAAAAACCAGAAAAGATGGAAAAGAAAT 4# FGFR1 downstream primer is the same as 2#: 2#-FGFR1 downstream primer 7# fusion protein:

7# VEGFR1 upstream primer is the same as 2#: 2#-VEGFR1 upstream primer

7# VEGFR1 downstream primer:
(SEQ ID NO: 50)
ACCGCCAGAGCCACCTCCGCCTGAACCGCCACCACCTTTTTCATCAGGG
TAACTCCAG 7#FGFR1 upstream primer:
(SEQ ID NO: 51)
AGGCGGAGGTGGCTCTGGCGGTGGCGGATCCCCAGAAAAGATGGAAAAG
AAATTG 7# FGFR1 downstream primer is the same as 2#: 2#-FGFR1 downstream primer.

9# fusion protein: 9# fusion protein comprises 5 segments: VEGFR1D1, VEGFR1D2, VEGFR2D3, FGFR and Fc.

VEGFR1D1 is amplified using pBLAST45-hFLT1s7cDNA with the following primers:

9#-VEGFR1D1 upstream primer:
(SEQ ID NO: 52)
TAGTTCCGGAAGCAAATTAAAAGATCCTGAACTGAG 9#-VEGFR1D1 downstream primer:
(SEQ ID NO: 53)
ATCTCTACGAAAGGTCTACCTGTATCACTAATAAATATATAG VEGFR1D2 is amplified using pBLAST45-hFLT1s7cDNA with the following primers:

9#-VEGFR1D2R2D3 upstream primer:
(SEQ ID NO: 54)
GGTAGACCTTTCGTAGAGATGT

9#-VEGFR1D2 downstream primer:
(SEQ ID NO: 75)
CATGAGACGGACTCAGAACCACATCTATGATTGTATTGGTTTG VEGFR2D3 is amplified using pBLAST45-hFLK1s7 as the template with the following primers:

9#-VEGFR2D3 upstream primer:
(SEQ ID NO: 76)
CAAACCAATACAATCATAGATGTGGTTCTGAGTCCGTCTCATG 9#-VEGFR1D2R2D3 downstream primer:
(SEQ ID NO: 55)
AGGTTTTTCATGGACCCTGAC 9#FGFR1 upstream primer:
(SEQ ID NO: 56)
TCAGGGTCCATGAAAAACCTCCAGAAAAGATGGAAAAGAAATTGC 10# fusion protein:

The PCR primers for the domain sequence of 10#VEGFR1 fragment are the same as 9#

10#-FGFR1 upstream primer:
(SEQ ID NO: 57)
TCAGGGTCCATGAAAAACCTAAAAATCGCACCCGCATCACAGG 16# fusion protein:

16#VEGFR1D1 upstream primer is the same as 9#-VEGFR1D1 upstream primer

16# VR1D2R2D3R downstream primer is the same as 9#-VR1D2R2D3R downstream primer

16#FGFR1 upstream primer:
(SEQ ID NO: 58)
GTCAGGGTCCATGAAAAACCTAGGCCGTCCCCGACCTTGCCTG 20# fusion protein:

20#-VEGFR1D1 upstream primer is the same as 9#-VEGFR1D1 upstream primer

20#-VR1D2R2D3R downstream primer is the same as 9#-VR1D2R2D3R downstream primer

20#-FGFR1 upstream primer:
(SEQ ID NO: 59)
CCTGTGATGCGGGTGCGATTAGGTTTTTCATGGACCCTGAC 21# fusion protein:

10# is used as the template for 21 #, in which the following primers are used to change one base in 10#FGFR1D1h so that Cys is changed to Ser:

21#-mutF:
(SEQ ID NO: 60)
CTCCGGCCTCTATGCTTCCGTAACCAGCAGCCCCTC

21#-mutR:
(SEQ ID NO: 61)
GAGGGGCTGCTGGTTACGGAAGCATAGAGGCCGGAG

24# fusion protein:

24#VEGFR1D1 upstream primer is the same as 9#-VEGFR1D1 upstream primer

24# VR1D2R2D3R downstream primer is the same as 9#-VR1D2R2D3R downstream primer

24#FGFR1 upstream primer:
(SEQ ID NO: 62)
TCAGGGTCCATGAAAAACCTTCGGGCAGTGACACCACCTAC 25# fusion protein:

25#VEGFR1D1 upstream primer is the same as 9#-VEGFR1D1 upstream primer

25# VR1 D2R2D3R downstream primer is the same as 9#-VR1 D2R2D3R downstream primer 25#FGFR1 upstream primer:
(SEQ ID NO: 63)
TCAGGGTCCATGAAAAACCTAACCCCGTAGCTCCATATTGG 28# fusion protein:

PCR is performed on 28# using 25# as the template with the same upstream primer as that of 2#-VEGFR1 and the same downstream primer as that of IgG1 Fc.

11#, 14# and 27# fusion protein-proteins comprise a part of the extracellular domain of FGFR1, a part of the extracellular domain of VEGFR1, a part of the extracellular domain of VEGFR2 and IgG1 Fc. Same IgG1 Fc upstream primer and same IgG1 Fc downstream primer are used for these 3 recombinant expression plasmids above.

The rest of the primers used are listed as follows:
11# fusion protein:

11#-FGFR1 upstream primer:
(SEQ ID NO: 64)
CTAGCTCCGGACCAGAAAAGATGGAAAAGAAATTGC

11#-FGFR1 downstream primer:
(SEQ ID NO: 65)
TCAGGATCTTTTAATTTTGACTCCAGGTACAGGGGCGAGGTC 11#-VEGFR1D1 upstream primer:
(SEQ ID NO: 66)
TCAAAATTAAAAGATCCTGAACTG 11#-VEGFR1D1 downstream primer: the same as 9#-VEGFR1D1 downstream primer:
11#VEGFR1D2R2D3 upstream primer is the same as 9#-VR1D2R2D3 upstream primer 11#VEGFR1D2D3 downstream primer:
(SEQ ID NO: 67)
TGGGCATGTGTGAGTTTTGTCAGGTTTTTCATGGACCCTGAC 14# fusion protein:

14#-FGFR1 upstream primer:
(SEQ ID NO: 68)
TAGTTCCGGAAAAAATCGCACCCGCATCACAG

14#FGFR1 downstream primer is the same as 11#-VEGFR1D1 downstream primer
14#VEGFR1D1 upstream primer is the same as 11#-VEGFR1D1 upstream primer
14#VEGFR1D1 downstream primer is the same as 9#-VEGFR1D1 downstream primer
14#VEGFR1D2R2D3 upstream primer is the same as 9#-VEGFR1D2R2D3 upstream primer
14#VEGFR1D2R2D3 downstream primer is the same as 11#-VEGFR1D2R2D3 downstream primer
27# fusion protein:
PCR is performed on 27# using 14# as the template with the same upstream primer as that of 27#-FGFR1 (TAGTTCCGGAAAACCTAACCCCGTAGCTCCAT) (SEQ ID NO:69) and the same downstream primer as that of IgG1 Fc:
12# fusion protein comprises a part of the extracellular domain of VEGFR1, a part of the extracellular domain of VEGFR2 and IgG1 Fc. The primers used are as follows:
12# upstream primer is the same as 9#-FGFR1 upstream primer
12#VEGFR2 downstream primer is the same as 11#VEGFR1D2D3 downstream primer Fc upstream primer 1: FcFor1:
(SEQ ID NO: 70)
GACAAAACTCACACATGCCCACC Fc downstream primer: the same as IgG1 Fc downstream primer above.
Fusion protein 15# comprises a part of the extracellular domain of VEGFR1 and IgG1 Fc. The primers used are as follows:
15# upstream primer is the same as 2#-VEGFR1 upstream primer:
(SEQ ID NO: 45)
ATAGTTCCGGAGGTAGACCATTCGTAGAGATG 15#VEGFR2 downstream primer is the same as 11#VEGFR1D2D3 downstream primer Fc upstream primer 1: FcFor1:
(SEQ ID NO: 70)
GACAAAACTCACACATGCCCACC Fc downstream primer: the same as IgG1 Fc downstream primer above.
Expression and Purification of the Fusion Protein
The present fusion protein may be expressed and purified by techniques commonly used in the art. DNA from corresponding fusion protein plasmid can be purified using plasmid purification kit (MAX) available from Qiagen, and the concentration of plasmid DNA is determined using UV spectrophotometry, and the plasmid can be transfected to CHO cell using FUGENE 6 liposome (Roche). Specific methods for transfection can be performed according to the specification of the product.
Based on the expression amount required for the proteins, two methods can be employed in the present invention for protein expression: (1) transient expression, in which the fusion protein contained culture supernatant is usually harvested 48-72 h after transfection, and the relative content of the fusion protein is then determined using human IgG ELISA so that the fusion protein may be rapidly and efficiently obtained; (2) establishing a stable cell line and producing the common DHFR-defective CHO cell expression system using the recombinant protein medicament expression, the basic process of which includes cell transfection, selection of stably transfected cell, clone screening, stress amplification, culture medium and process optimization and the like, and finally realizing a large-scale suspension culture of CHO engineering cell strain in a serum free culture medium. The culture product is collected and the fusion protein is purified using Protein A affinity column. The purified protein is analyzed by sodium dodecyl sulfate polyacrylamide gel electrophoresis (SDS-PAGE), and subsequently all eluents in which the required expression product is contained were combined and filtered using a 0.22 μm filter, and then protein quantification is carried out according to a plurality of methods such as Lowry protein assay. The volume of CHO cell culture in the present invention is at a level of 10 L bioreactor, through which the fusion protein obtained after purification could satisfy the protein amount required in the animal experiments, and also a basis is established for future scaling-up.
Neutralization of VEGF and FGF by the Fusion Protein is Validated at a Protein Level
After the fusion protein expressed by CHO is obtained, the binding capacity of the fusion protein to VEGF and FGF is evaluated in the present invention at a level of protein. Binding experiment and affinity experiment are performed for validation in the present invention, in which steps of the binding experiment included: after initially coated by VEGF and FGF-2 on a 96-well ELISA plate, the coated well is blocked by BSA followed by adding each fusion protein at the same concentration, and then a secondary antibody to human IgG Fc-HRP is added after washing, and the samples are developed, stopped and read at 450 nm on a ELISA plate, and finally the fusion protein which had binding capacity to VEGF and FGF-2 is screened based on the signal strength. The affinity experiment is performed in order to determine the affinity of the fusion protein to VEGF or FGF-2 in the solution system, which comprised the following steps: VEGF or FGF-2 is initially coated on a 96-well ELISA plate to capture the antibody, and then the coated well is blocked by BSA, and subsequently a mixture of the fusion protein and VEGF or FGF-2 which is previously prepared and incubated are added with a gradient of diluted standards, and after incubation, an HRP-labeled detection antibody is added (using antibody 2 which specifically detected free VEGF or FGF-2), and subsequently the samples are developed, stopped and read at 450 nm on a ELISA plate, and finally the relative concentration of free VEGF or FGF-2 is detected in the mixture of the fusion protein and VEGF or FGF-2. Through the experiments above, the fusion protein having a dual-blocking effect on VEGF and FGF-2 is screened.

Neutralization of VEGF and FGF by the Fusion Protein is Validated at a Cellular Level After the binding capacity of the fusion protein to VEGF and FGF-2 is determined at a level of protein, its angiogenesis-inhibiting effect is validated at a cellular level in the present invention. The inhibition capacity of the fusion protein on the division and migration of the vascular endotheliocyte is examined by the division test using human umbilical vein endothelial cell (HUVEC) and the HUEVC cell migration test. The inhibition capacity of the fusion protein on the division of HUVEC cell can be examined by the HUVEC cell division test, which comprises the following steps during the experiment: 3000 HUVEC cells/well are inoculated to a 96-well plate and cultured at 37° C. in an incubator supplemented with 5% CO2, and then VEGF or FGF-2 as well as a mixture of the fusion protein at different concentrations with VEGF or FGF-2 are added respectively, and after culturing for another 3-4 days, 10% CCK-8 is added and cultured for 2 h before the sample is read at 450 nm on a ELISA plate. The inhibition capacity of the fusion protein on the division of vascular endotheliocyte induced by VEGF or FGF-2 is evaluated based on the difference of absorbance, and the median effective concentration of the fusion protein is obtained for VEGF or FGF-2 inhibition. The inhibition capacity of the fusion protein on HUVEC cell migration is examined by the HUVEC cell migration test, which comprises the following steps during the experiment: 50000 HUVEC cells as well as the fusion protein at various concentrations are initially inoculated in the upper chamber, while 600 μL VEGF or FGF-2 containing culture liquid is added into the lower chamber, and subsequently, the sample is cultured at 37° C. in an incubator supplemented with 5% CO2 for 20-24 h before cells on the face side of the membrane of the upper chamber are removed, and then cells on the back side of the membrane are fixed, stained and washed with PBS before observed and counted under an inverted microscope. The migration of HUVEC cells induced by the stimulation of VEGF or FGF-2 is demonstrated by counting the HUVEC cells on the back side of the membrane, and the inhibition capacity of the fusion protein on the migration of the vascular endotheliocyte is tested by adding the fusion protein at various concentrations into the culture liquid. Through the experiments mentioned above, the inhibition capacity of the new fusion protein constructed in the present invention is validated on the division and migration of the vascular endotheliocyte induced by VEGF and FGF-2, which can be used in animal experiments.

Tumor Growth-Inhibiting Capacity of the Fusion Protein is Validated by a Tumor Model The blocking effect of the fusion protein of the present invention on VEGF and FGF-2 signal is demonstrated by experiments at a protein level and a cellular level. Also, its anti-tumor capacity is tested in animal tumor models.

Specifically, the anti-angiogenesis and anti-tumor effect of the fusion protein are investigated in models commonly used in searching medicaments for angiogenesis and tumor, for example, LLC mouse lung cancer, U87 gliocytoma, B16 melanoma and so on. In animal experiments, conventional control groups, control medicaments, such as VEGF-Trap, FP-1039, are used to obtain comparative data for anti-tumor capacity.

In the experiments, 100 μL tumor cell liquid at an appropriate amount is subcutaneously injected into C57 mouse on one side of the back, and the tumor volume is measured with a vernier caliper twice a week. When the tumor grows to about 200 $mm^3$, the fusion protein at various concentrations is subcutaneously injected into the mice and the mice are sacrificed after 2-3 weeks. Subsequently, the tumor volume is measured with a vernier caliper.

The fusion protein of the present invention reduces tumor size and has anti-tumor effects. Also, individual tumor tissue can be analyzed using methods such as immunohistochemistry to determine the mechanism of the fusion proteins in inhibiting angiogenesis.

EXAMPLES

Following are examples that illustrate embodiments and procedures for practicing the invention. The examples should not be construed as limiting.

Example 1

Construction of Recombinant Expression Plasmid for the Dual-Target Fusion Protein A commercially available cDNA (PCR Ready First Strand cDNA, derived from human adult colon cancer tissue, BioChain) is used as the template for FGFR1 fragment. A commercially available plasmid pBLAST45-hFLT1s7cDNA (InvivoGen) is used as the template for VEGFR1 fragment, and a commercially available plasmid pBLAST45-hFLK1s7 (InvivoGen) is used as the template for VEGFR2 fragment.

Total RNA is extracted from the blood of healthy human subjects using human blood RNA extraction kit (QIAGEN). According to the manufacturer's instruction of reverse transcription kit (Promega), RT-PCR is performed using M-MLV reverse transcriptase (Promega) so that RNA is reversely transcribed to cDNA is for use as the template for IgG1 Fc fragment. RT-PCR is performed according to the manufacturer's instruction of reverse transcription kit, which has the following steps: Oligo dT, dNTP, total RNA and DEPC $H_2O$ are mixed homogeneously and reacted at 70° C. for 10 min before placed on ice for 5 min, and subsequently RNase inhibitor, M-MLV reverse transcriptase and reaction buffer are added. The mixture is reacted at 42° C. for 1 h and subsequently at 70° C. for 15 min, and the cDNA obtained can be used as a template.

Various FGFR1 fragments are individually amplified by PCR using the cDNA from human adult colon cancer tissue as the template (the primers are listed in table 1), and various VEGFR1 and VEGFR2 fragments are amplified using a commercially available plasmid as the template (the primers are listed in table 1), and IgG1 Fc fragment is amplified by PCR using human blood cDNA as the template (the primers are listed in Table 1 and 2).

When PCR primers are designed, 20 or more complementary base sequences are introduced as the linking sequence among VEGFR1 fragment, VEGFR2 fragment, FGFR1 fragment and IgG1 Fc fragment so that each fragment may be subsequently linked by overlap PCR to form reading frames for different fusion proteins, and at the same time, restriction endonuclease BspE I and Pst I sites are added at both ends of the PCR product.

Subsequently, overlap PCR is carried out to obtain each FGFR1-Fc fusion protein fragment by amplification. The reaction conditions for the PCR are as follows: 5 min of pre-denaturalization at 98° C., total 30 cycles of 30 s of denaturalization at 98° C., 45 s of annealing at 56° C. and 2 min of extension at 72° C., and finally another 10 min of extension. When PCR primers are designed, the linking sequence is introduced between different fragments so that different fragments may be linked by overlap PCR. The process of the overlap PCR reaction may be divided into two rounds, in which the fragment required for linking and containing no primer is included in the first round with reaction conditions as follows: 5 min of pre-denaturalization at 98° C., 6 cycles of 30 s of denaturalization at 98° C., 45 s of annealing at 56° C. and 5 min of extension at 72° C., and finally another 10 min of extension at 72° C.; after the first round, the second round of PCR is carried out by adding the primers for both ends with reaction conditions as follows: 5 min of pre-denaturalization at 98° C., 30 cycles of 30 s of denaturalization at 98° C., 45 s of annealing at 56° C. and 2 min of extension at 72° C., and finally another 10 min of extension at 72° C.; through the process above, reading frames for different fusion proteins are spliced, and at the same time, endoenzyme BspE I and Pst I sites are added at both ends of the cDNA.

After amplification, the fragments amplified by PCR are purified using QIAquick PCR purification kit (QIAGEN). cDNAs of various fusion proteins and the eukaryotic expression plasmid pSV2-dhfr (ATCC) are digested by BspE I and Pst I, respectively. Subsequently, 1% agarose gel electrophoresis is performed on the digested samples under a voltage of 90 V. Target fragments are recovered using QIAquick gel extraction kit (QIAGEN) before ligating at 16° C. for 1 h using a ligase (NEB). The mixture for ligation reaction is transformed to the competent Top10 *E. coli* under the conditions of 90 s of reaction at 42° C. followed by 3 min of standing on ice. After the sterile LB culture broth (free of antibody) added, the mixture is shaken at 250 rpm in a shaker at 37° C. for 1 h before coating on a LB plate supplemented with ampicillin. The plate is cultured overnight in a thermostated incubator at 37° C., and then single colonies are picked out and transferred to an ampicillin-containing LB culture broth. The inoculated culture broth is shaken at 250 rpm in a shaker at 37° C. overnight before the plasmid is extracted using alkaline lysis. Subsequently, the sample is digested by restriction endonuclease before evaluated by 1% agarose gel electrophoresis under a voltage of 90 V. The recombinant plasmid with correct endonuclease digestion is confirmed by DNA sequencing. Based on the steps as mentioned above, 2#, 4#, 7#, 9#, 10#, 11#, 12#, 14#, 15#, 16#, 20#, 21#, 24#, 25#, 27# and 28# recombinant expression plasmid are constructed.

Among others, 2#, 4# and 7# fusion protein comprise a part of the extracellular domain of VEGFR1, a part of the extracellular domain of FGFR1 and IgG1 Fc, in which said a part of the extracellular domain of VEGFR1 is amplified by PCR using pBLAST45-hFLT1s7cDNA as the template, and said a part of the extracellular domain of FGFR1 is amplified by PCR using human colon cancer tissue cDNA as the template, and the human IgG1 Fc region is amplified using human blood cDNA as the template. Subsequently, a PCR product with three linked fragments is obtained by overlap PCR, which is introduced into an expression vector after digestion and ligation. The primers used are listed in table 1.

9#, 10#, 16#, 20#, 21#, 24#, 25# and 28# comprise a part of the extracellular domain of VEGFR1, a part of the extracellular domain of VEGFR2, a part of the extracellular domain of FGFR1 and IgG1 Fc. First of all, 9# construct is constructed, in which fragment VEGFR1D1 and fragment VEGFR1D2 are amplified by PCR using pBLAST45-hFLT1s7cDNA as the template, and fragment VEGFR2D3 is amplified by PCR using pBLAST45-hFLK1s7 as the template, said a part of the extracellular domain of FGFR1 is amplified by PCR using human colon cancer tissue cDNA as the template, and the human IgG1 Fc region is amplified using human blood cDNA as the template. Subsequently, a PCR product with five linked fragments is obtained by overlap PCR, which is introduced into an expression vector after digestion and ligation. Subsequently, VEGFR fragment is amplified by PCR using 9# construct as the template, and said a part of the extracellular domain of FGFR1 is amplified by PCR using human colon cancer tissue cDNA as the template, and the human IgG1 Fc region is amplified using human blood cDNA as the template. Subsequently, a PCR product of three linked fragments is obtained by overlap PCR, which is introduced into an expression vector after digestion and ligation to obtain 10#, 16#, 20#, 24# and 25# construct. Subsequently, one base in 10#FGFR1D1h is mutated by PCR with the primers indicated in Table 1 using 10# as the template. Particularly, 214 construct is obtained by changing Cys into Ser according to the manufacturer's instruction for site-directed mutagenesis kit (QuikChange™ Site-Directed Mutagenesis Kit, STRATAGEN), the specific process of which is as follows: PCR reaction is carried out by adding de-ionized water, 10# plasmid, dNTP, mutation primers indicated in Table 1, reaction buffer solution and Pfu enzyme into a PCR tube under the following conditions: 2 min of pre-denaturalization at 95° C., 18 cycles of 50 s of denaturalization at 95° C., 50 s of annealing at 60° C. and 8 min of extension at 68° C., and finally another 10 min of extension. After PCR, 1 μL Dpn I (NEB) is added for 1 h of reaction at 37° C. 2 μL reaction product is collected for transforming competent Top10 *E. coli* under the following conditions: 90 s of reaction at 42° C. before 3 min of standing on ice; sterile LB culture broth (free of antibody) added, and then cultured in a shaker at 250 rpm for 1 h at 37° C. before coating on a LB plate supplemented with ampicillin; the plate cultured overnight in a thermostated incubator at 37° C., and then single colonies picked out and transferred to a ampicillin containing LB culture broth; the inoculated culture broth cultured at 250 rpm in a shaker at 37° C. overnight before extracting the plasmid using alkaline lysis; subsequently, evaluating the sample by DNA sequencing. 28# construct is obtained by PCR with 2#-VEGFR1 upstream primer and IgG1 Fc downstream primer using 25# as the template. The primers used are listed in table 1.

11#, 14# and 27# comprise a part of the extracellular domain of FGFR1, a part of the extracellular domain of VEGFR1, a part of the extracellular domain of VEGFR2 and IgG1 Fc. Said a part of the extracellular domain of FGFR1 is amplified by PCR using human colon cancer tissue cDNA as the template, and VEGFR fragment is amplified by PCR using 9# construct as the template, and the human IgG1 Fc region is amplified using human blood cDNA as the template. Subsequently, a PCR product of three linked fragments is obtained by overlap PCR, which is introduced into an expression vector after digestion and ligation, and 11# and 14# construct are obtained thereby. 27# construct is then obtained by PCR using 14# construct as the template. The primers used are listed in table 1.

12# fusion protein comprises a part of the extracellular domain of VEGFR1, a part of the extracellular domain of VEGFR2 and IgG1 Fc. Using 9# construct as the template, human IgG1 Fc region is amplified with 9#-VEGFR1D1 upstream primer and 11#VEGFR1D2D3 downstream primer using human blood cDNA as the template. Subsequently, a PCR product of two linked fragments is obtained by overlap PCR, which is introduced into an expression vector after digestion and ligation, and thereby 12# is constructed.

15# fusion protein comprises a part of the extracellular domain of VEGFR1, a part of the extracellular domain of VEGFR2 and IgG1 Fc. Using 9# construct as the template, human IgG1 Fc region is amplified with 2#-VEGFR1 upstream primer and 11#VEGFR1D2D3 downstream primer using human blood cDNA as the template. Subsequently, a PCR product of two linked fragments is obtained by overlap PCR, which is introduced into an expression vector after digestion and ligation, and thereby 15# is constructed.

26# fusion protein comprises a part of the extracellular domain of FGFR1 and IgG1 Fc. Said a part of the extracellular domain of FGFR1 is amplified by PCR using human colon cancer tissue cDNA as the template, and human IgG1 Fc region is amplified with the upstream primer of SEQ ID NO: 73 and the downstream primer of SEQ ID NO: 74 using human blood cDNA as the template. Subsequently, a PCR product of two linked fragments is obtained by overlap PCR, which is introduced into an expression vector after digestion and ligation, and thereby 26# is constructed.

The protein sequence of VEGFR-FGFR-Fc in each fusion protein and its encoding nucleotide sequence are listed in Table 2. The schematic diagram of the fusion protein structure is shown in FIG. 1.

TABLE 1

Primers used for amplification of VEGFR and FGFR fragment during vector construction

| Fusion protein | Fragment | Upstream primer | Downstream primer |
|---|---|---|---|
| 2# | 2#VEGFR1 | SEQ ID NO: 45 | SEQ ID NO: 46 |
| | 2#FGFR1 | SEQ ID NO: 47 | SEQ ID NO: 42 |
| | Fc | SEQ ID NO: 43 | SEQ ID NO: 44 |
| 4# | 4#VEGFR1 | SEQ ID NO: 45 | SEQ ID NO: 48 |
| | 4#FGFR1 | SEQ ID NO: 49 | SEQ ID NO: 42 |
| | Fc | SEQ ID NO: 43 | SEQ ID NO: 44 |
| 7# | 7#VEGFR1 | SEQ ID NO: 45 | SEQ ID NO: 50 |
| | 7#FGFR1 | SEQ ID NO: 51 | SEQ ID NO: 42 |
| | Fc | SEQ ID NO: 43 | SEQ ID NO: 44 |
| 9# | 9#-VEGFR1D1 | SEQ ID NO: 52 | SEQ ID NO: 53 |
| | 9#-VEGFR1D2 | SEQ ID NO: 54 | SEQ ID NO: 75 |
| | 9#-VEGFR2D3 | SEQ ID NO: 76 | SEQ ID NO: 55 |
| | 9#FGFR1 | SEQ ID NO: 56 | SEQ ID NO: 42 |
| | Fc | SEQ ID NO: 43 | SEQ ID NO: 44 |
| 10# | 10#-VEGFR1D1 | SEQ ID NO: 52 | SEQ ID NO: 53 |
| | 10#-VEGFR1D2R2D3 | SEQ ID NO: 54 | SEQ ID NO: 55 |
| | 10#FGFR1 | SEQ ID NO: 57 | SEQ ID NO: 42 |
| | Fc | SEQ ID NO: 43 | SEQ ID NO: 44 |
| 11# | 11#FGFR1 | SEQ ID NO: 64 | SEQ ID NO: 65 |
| | 11#-VEGFR1D1 | SEQ ID NO: 66 | SEQ ID NO: 53 |
| | 11#-VEGFR1D2R2D3 | SEQ ID NO: 54 | SEQ ID NO: 67 |
| | Fc | SEQ ID NO: 43 | SEQ ID NO: 44 |
| 12# | 12#VEGFR | SEQ ID NO: 56 | SEQ ID NO: 67 |
| | Fc | SEQ ID NO: 43 | SEQ ID NO: 44 |
| 14# | 14#FGFR1 | SEQ ID NO: 68 | SEQ ID NO: 53 |
| | 14#-VEGFR1D1 | SEQ ID NO: 66 | SEQ ID NO: 53 |

TABLE 1-continued

Primers used for amplification of VEGFR and FGFR fragment during vector construction

| Fusion protein | Fragment | Upstream primer | Downstream primer |
|---|---|---|---|
| | 14#-VEGFR1D2R2D3 | SEQ ID NO: 54 | SEQ ID NO: 67 |
| | Fc | SEQ ID NO: 43 | SEQ ID NO: 44 |
| 15# | 15#VEGFR | SEQ ID NO: 45 | SEQ ID NO: 67 |
| | Fc | SEQ ID NO: 70 | SEQ ID NO: 44 |
| 16# | 16#-VEGFR1D1 | SEQ ID NO: 52 | SEQ ID NO: 53 |
| | 16#-VEGFR1D2R2D3 | SEQ ID NO: 54 | SEQ ID NO: 55 |
| | 16#FGFR1 | SEQ ID NO: 58 | SEQ ID NO: 42 |
| | Fc | SEQ ID NO: 43 | SEQ ID NO: 44 |
| 20# | 20#-VEGFR1D1 | SEQ ID NO: 52 | SEQ ID NO: 53 |
| | 20#-VEGFR1D2R2D3 | SEQ ID NO: 54 | SEQ ID NO: 55 |
| | 20#FGFR1 | SEQ ID NO: 59 | SEQ ID NO: 42 |
| | Fc | SEQ ID NO: 43 | SEQ ID NO: 44 |
| 21# | 21# | SEQ ID NO: 60 | SEQ ID NO: 61 |
| 24# | 24#VEGFR | SEQ ID NO: 52 | SEQ ID NO: 55 |
| | 24#FGFR1 | SEQ ID NO: 62 | SEQ ID NO: 42 |
| | Fc | SEQ ID NO: 43 | SEQ ID NO: 44 |
| 25# | 25#VEGFR | SEQ ID NO: 52 | SEQ ID NO: 55 |
| | 25#FGFR1 | SEQ ID NO: 63 | SEQ ID NO: 42 |
| | Fc | SEQ ID NO: 43 | SEQ ID NO: 44 |
| 26# | 26#FGFR1 | SEQ ID NO: 73 | SEQ ID NO: 74 |
| | Fc | SEQ ID NO: 43 | SEQ ID NO: 44 |
| 27# | 27#VEGFR-FGFR1-Fc | SEQ ID NO: 69 | SEQ ID NO: 44 |
| 28# | 28#VEGFR-FGFR1-Fc | SEQ ID NO: 45 | SEQ ID NO: 44 |

TABLE 2

Protein sequences and nucleotide sequences for the fusion proteins in the present invention

| Fusion protein | Amino acid sequence | Nucleotide sequence |
|---|---|---|
| 2# | SEQ ID NO: 9 | SEQ ID NO: 26 |
| 4# | SEQ ID NO: 10 | SEQ ID NO: 27 |
| 7# | SEQ ID NO: 11 | SEQ ID NO: 28 |
| 9# | SEQ ID NO: 12 | SEQ ID NO: 29 |
| 10# | SEQ ID NO: 13 | SEQ ID NO: 30 |
| 11# | SEQ ID NO: 14 | SEQ ID NO: 31 |
| 12# | SEQ ID NO: 15 | SEQ ID NO: 32 |
| 14# | SEQ ID NO: 16 | SEQ ID NO: 33 |
| 15# | SEQ ID NO: 17 | SEQ ID NO: 34 |
| 16# | SEQ ID NO: 18 | SEQ ID NO: 35 |
| 20# | SEQ ID NO: 19 | SEQ ID NO: 36 |
| 21# | SEQ ID NO: 20 | SEQ ID NO: 37 |
| 24# | SEQ ID NO: 21 | SEQ ID NO: 38 |
| 25# | SEQ ID NO: 22 | SEQ ID NO: 39 |
| 26# | SEQ ID NO: 71 | SEQ ID NO: 72 |
| 27# | SEQ ID NO: 23 | SEQ ID NO: 40 |
| 28# | SEQ ID NO: 24 | SEQ ID NO: 41 |

Example 2

Transient Expression and Quantification of the Fusion Proteins

The DNA of individual fusion protein plasmid is purified using MAX Plasmid Purification Kit (Qiagen). The concentration of the plasmid DNA is determined by UV spectrophotometry. 1 μg recombinant plasmid and 6 μL liposome (FuGENE 6 Transfection Reagent, Roche) are homogeneously mixed into 100 μL fresh IMDM culture broth (GIBCO); after standing for 15 min, the mixture is added to the CHO cells (ATCC) cultured overnight after inoculation at a cell density of $3\times10^5$/mL into a 6-well plate; the mixture is cultured at 37° C. in an incubator supplemented with 5% $CO_2$ for 48 h with a cell complete culture broth containing 88% IMDM, 10% FBS, 1% HT and 1% glutamine (all supplied by GIBCO); subsequently, the supernatant is collected and determined for the relative content of the fusion protein using human IgG ELISA kit for protein quantification (BETHYL).

The relative content of the fusion protein expressed and secreted by CHO is determined with the following steps: 100 μL anti-human IgG-Fc protein (10 μg/mL) purified by affinity is coated to a 96-well ELISA plate (IMMULON) and subsequently washed for 5 times using 300 μL PBST washing solution; each coated well is blocked with 200 μL freshly prepared blocking working solution (blocking stock solution:PBS=1:19) and incubated at 37° C. for 1 h; after washed in 300 μL PBST washing solution for 5 times, 100 μL IgG solution diluted in a gradient (200 ng/mL original concentration and diluted by PBS in the multiple proportion of 1:2) as a standard and 100 μL culture supernatant of each fusion protein diluted in a gradient (starting with the concentration of each culture supernatant, and diluted by PBS in the multiple proportion of 1:5) are added to each well and incubated at 37° C. for 2 h; after washed in 300 μL PBST washing solution for 5 times, 100 μL anti-human IgG Fc-HRP secondary antibodies diluted with PBS in a ratio of 1:10000 is added and incubated at 37° C. for 1 h; after washed in 300 μL PBST ishing solution for 5 times, the well is developed by adding 100 μL developing solution (KPL); finally, after the development is stopped by adding 1004 stopping solution (KPL), the absorbance of the ELISA plate is read at a wavelength of 450 nm on a ELISA reader. The concentrations of various fusion proteins may thereby be determined according to the standard curve.

Example 3

Binding of the Fusion Proteins

The binding capacities of the fusion proteins as constructed above to VEGF and FGF-2 are detected using ELISA. Initially, a 96-well ELISA plate (IMMULON Company) is coated by 100 μL solution (100 ng/mL heparin (Sigma) contained) containing 20 ng/mL VEGF (R & D Systems) and 50 ng/mL FGF-2 (R & D Systems). Subsequently, the plate is washed in 300 μL PBST washing solution for 5 times before each coated well is blocked in 200 μL freshly prepared blocking working solution (KPL Company) (blocking stock solution:PBS=1:19) and incubated at 37° C. for 1 h. After washed in 300 μL PBST washing solution for 5 times, 100 μL solutions of various fusion proteins (dissolve in PBS, pH=7.2, concentration of 20 ng/ml) are added and incubated at 37° C. for 2 h. After washed in 3004 PBST washing solution for 5 times, 100 μL anti-human IgG Fc-HRP secondary antibody (BETHYL Company) diluted with PBS in a ratio of 1:10000 is added and incubated at 37° C. for 1 h. After washed in 300 μL PBST ishing solution for 5 times, the well is developed by adding 100 μL developing solution (KPL Company), and finally the development is stopped by adding 1004 stopping solution (KPL Company) before the absorbance of the ELISA plate is read at a wavelength of 450 nm on a ELISA reader. If the binding capacity of the fusion protein to VEGF or FGF2 is higher, the absorbance is higher and the signal is stronger.

Figure 2:
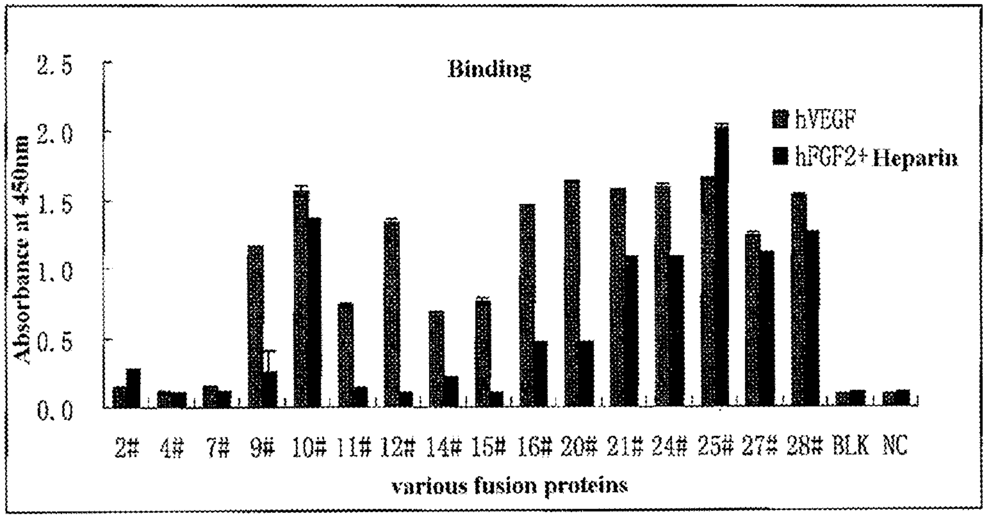
FIG. 2 is a comparative figure showing VEGF and FGF-2 binding by respective Fc fusion proteins, in which the binding between respective Fc fusion protein (20 ng/mL) and coated VEGF165 and/or FGF-2 (containing 100 ng/mL Heparin) is detected by enzyme-linked immunosorbent assay (ELISA).

Based on the intensity of the signal, 25# and 28# fusion protein are determined to have high binding capacity to both VEGF and FGF-2. Comparison between binding of the fusion protein to VEGF and FGF-2 is shown in FIG. 2.

Example 4

Stable Expression and Purification of the Fusion Proteins

DHFR-defective CHO cells (ATCC) are transfected by the recombinant expression plasmid of 25# fusion protein (high binding capacity) as well as 12# and 15# fusion protein (control) through a liposome (Roche). Particularly, 5 μg recombinant plasmid and 30 μL liposome (FuGENE 6 Transfection Reagent, Roche) are homogeneously mixed into 100 μL fresh IMDM culture broth (GIBCO); after standing for 15 min, the mixture is added to the DHFR-defective CHO cells (ATCC) cultured overnight after inoculation at a cell density of $3\times10^5$/mL in a 10 cm culture dish (Corning); the mixture is cultured at 37° C. in an incubator supplemented with 5% $CO_2$ for 2-3 days with a cell complete culture broth containing 10% FBS, 1% HT and 1% glutamine in a IMDM culture medium (all supplied by GIBCO); subsequently, the cells are digested by trypsin (GIBCO), inoculated at a cell density of $3\times10^5$/mL in 30 mL serum-free 302 culture medium (SAFC) in a flask, and selectively cultured at 37° C. in an incubator supplemented with 5% $CO_2$ at 100 rpm to a cell density of $10^6$/mL.

Subsequently, 3000 cells are inoculated into a 10 cm culture dish (Corning) (the culture broth containing 10% FBS and 1% glutamine in an IMDM culture medium) and cultured at 37° C. in an incubator supplemented with 5% $CO_2$ to form single clones. These single clones are picked out and cultured in a 96-well plate (Corning). The relative content of the fusion protein expressed and secreted by each individual single clone is determined using a human IgG ELISA kit for protein quantification (BETHYL) under the same conditions and steps as described in Example 2 for the determination of the relative content of the fusion protein. The clone with the highest expression amount is screened out and transferred to a 6-well plate for culturing to a confluence rate of about 70%. The cells are digested by trypsin and transferred to a 10 cm culture dish. Subsequently, gradual stress amplification is carried out by adding methotrexate (MTX, Sigma) with various concentrations (10 nM, 20 nM, 50 nM, 100 nM, 200 nM and 500 nM). After stress amplification, the cells are digested by trypsin and inoculated at a cell density of $3\times10^5$/mL in a flask. The expression amount of a single cell is determined so that genetically engineered stains of CHO are obtained for expressing a particular fusion protein.

Finally, large-scale suspension culture (volume of 10 L) of the genetically engineered stain of CHO is carried out at 37° C., 5% $CO_2$, 40% dissolved oxygen and 80 rpm in a serum-free 302 culture medium (pH 7.0, SAFC). The culture product is collected by centrifugation. After the supernatant is filtered using 0.45 μm filter membrane (Millipore), affinity chromatography is performed according to the instruction manual of Protein A affinity column (GE) with the specific steps as follows: initially, a protein A affinity column is equilibrated by a PBS buffer (pH 7.0); subsequently, the supernatant is loaded on the column and washed again with the PBS buffer; finally, the column is eluted with a citric acid buffer (pH 3.0), and the eluent is collected and filtered by a 0.45 μm filter membrane. After virus inactivation by adding S/D (0.3% tributyl phosphate/1% Tween 80) at 24° C. for 6 h, the target protein is further purified by a molecular sieve chromatography with the following steps: first, the eluent obtained from the Protein A affinity chromatography is dialyzed in a dialysis bag against a PBS buffer; subsequently, the sample is concentrated in a 10 KD ultrafiltration cup (Millipore); the sample concentrated using the ultrafiltration cup is then loaded on a molecular sieve chromatography column Superdex 200 (GE) equilibrated by a PBS buffer, and subsequently the column is eluted with a PBS buffer and the eluting peak is collected.

Figure 3:
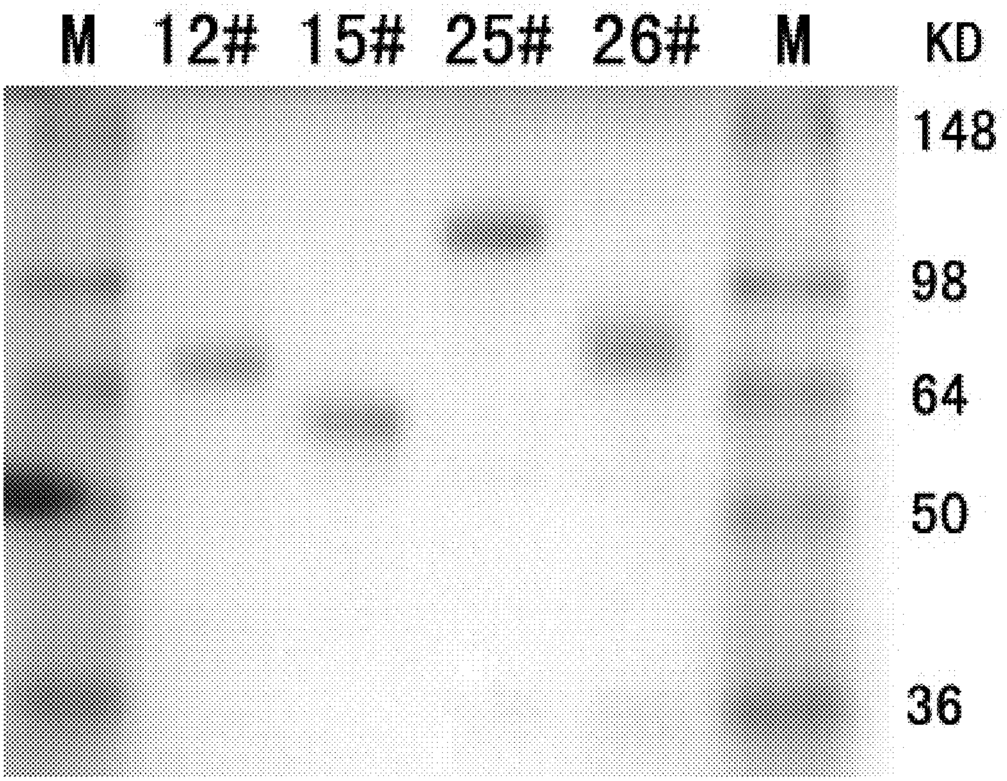
FIG. 3 is a figure showing SDS-PAGE analysis of the fusion protein.

The purified protein is analyzed by SDS-PAGE (FIG. 3); and subsequently, the eluents containing the required expression product is combined and filtered with a 0.22 μm filter membrane (Millipore) before the protein content is determined using many methods such Lowry protein assay.

Example 5

Gradient-Binding Experiment of the Fusion Proteins

Figure 4A:
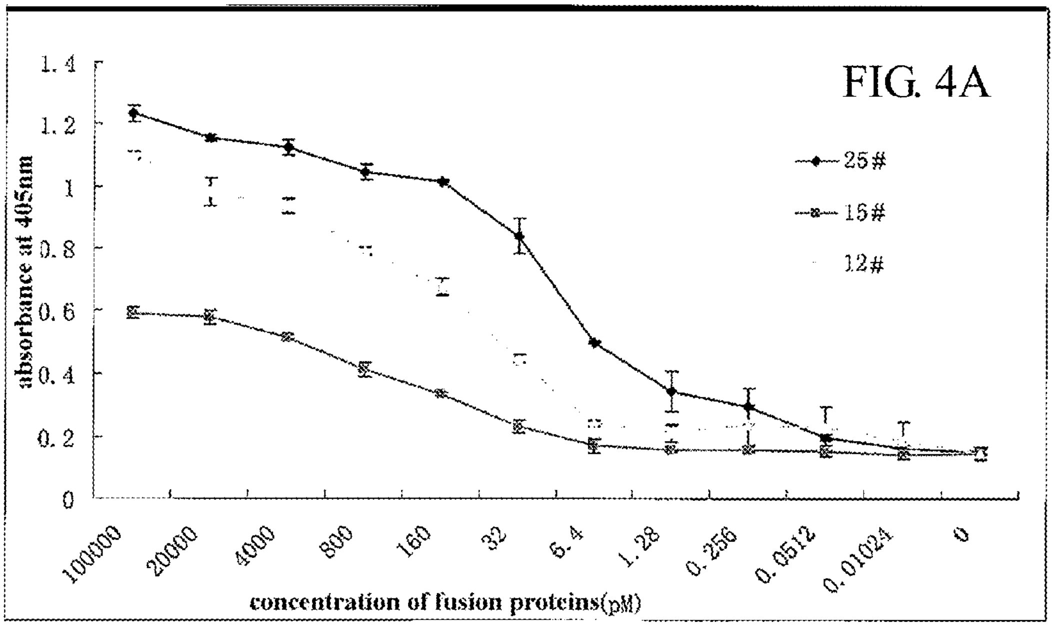
FIG. 4 shows the binding of VEGF (A) and FGF-2 (B) by a gradient concentration of fusion proteins.
Figure 4B:
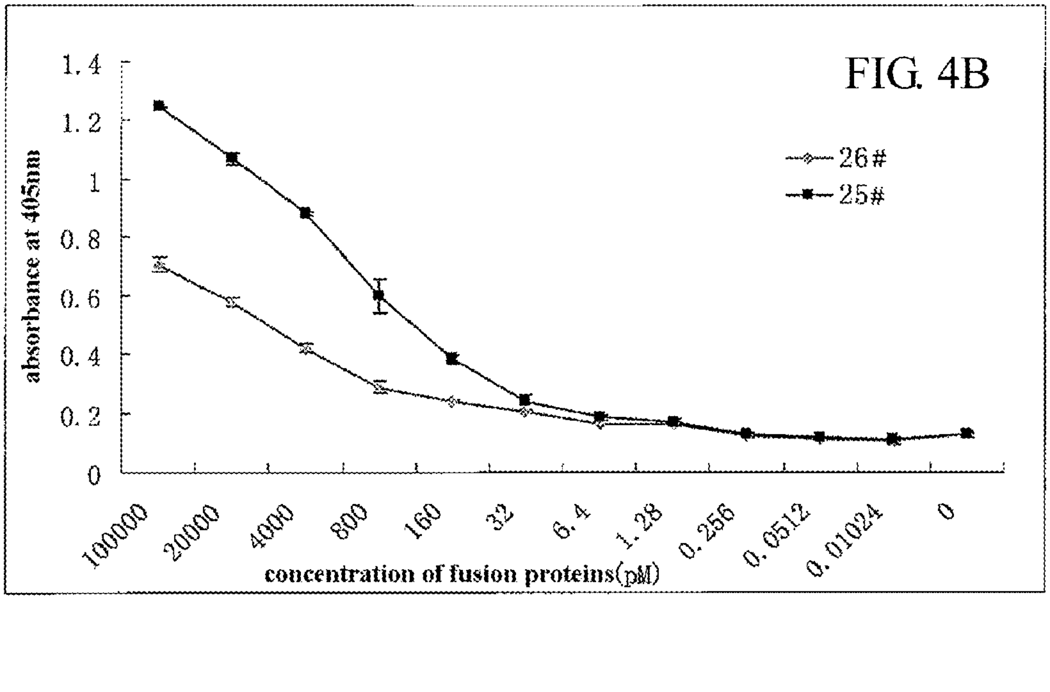

The binding capacities of the fusion proteins as constructed above to VEGF and FGF-2 are detected by ELISA, similarly as in Example 3. Initially, a 96-well ELISA plate is coated by 100 μL solution containing 20 ng/mL VEGF and 50 ng/mL FGF-2 (R&D Systems). Subsequently, the plate is washed in 300 μL PBST washing solution for 5 times before each coated well is blocked by 200 μL freshly prepared blocking working solution (KPL) (blocking stock solution: PBS=1:19) and incubated at 37° C. for 1 h. After washed in 300 μL PBST washing solution for 5 times, 100 μL solutions containing various fusion proteins at different concentrations (the starting content of protein is 1000000 pM, and is diluted in a ratio of 1:5) are added and incubated at 37° C. for 2 h. After washed in 300 μL PBST washing solution for 5 times, 100 μL anti-human IgG Fc-HRP secondary antibody (BETHYL) diluted with PBS in a ratio of 1:10000 is added and incubated at 37° C. for 2 h. After washed in 300 μL PBST washing solution for 5 times, the well is developed by adding 100 μL developing solution (KPL), and finally the development is stopped by adding 100 μL stopping solution (KPL) before the absorbance of the ELISA plate is read at a wavelength of 450 nm on a ELISA reader. Based on the intensity of the signal, the gradient binding capacities of the fusion proteins to VEGF and FGF-2 are determined Comparison of the gradient binding capacity to VEGF and FGF-2 among 12#, 15# and 25# fusion protein is shown in FIG. 4A. Furthermore, 25# is also compared with an FGFR-Fc fusion protein (Designated as 26#), as shown in FIG. 4B. Among others, 26# FGFR-Fc fusion protein comprises the second Ig-like domain of FGFR, the third Ig-like domain of FGFR and Fc region, and its amino acid sequence is shown in SEQ ID NO: 71 and its encoding nucleotide sequence is shown in SEQ ID NO: 72. The 26# fusion protein may be obtained by the following steps: similarly as in Example 1, FGFR1 fragment is amplified by PCR using human adult colon cancer tissue cDNA as the template (primers: SEQ ID NO: 73 and SEQ ID NO: 74), and IgG1 Fc fragment is amplified by PCR using human blood cDNA as the template (primers: SEQ ID NO: 43 and SEQ ID NO: 44), and then they are cloned into an expression vector through ligation by overlap PCR.

As demonstrated in this Example, the binding capacity to VEGF and FGF-2 increases as the molar concentration of the present VEGFR-FGFR-Fc fusion protein increases, as indicated by a stronger signal at the wavelength of 450 nm; while the binding capacity to VEGF and FGF-2 decreases correspondingly with the gradient dilution of the molar concentration of the present fusion protein.

Example 6

Affinity Experiment of the Fusion Proteins

The affinity of the fusion protein to VEGF or FGF-2 in a solution system is determined by an affinity experiment. Initially, a 96-well ELISA plate is coated by 1004 solution containing 1.0 μg/mL VEGF or 100 μL solution containing 2.0 μg/mL FGF-2 capture antibody (R&D Systems). Subsequently, the plate is washed in 300 μL PBST washing solution for 5 times before each coated well is blocked by a blocking working solution (KPL) (as seen in Example 3) and incubated at 37° C. for 1 h. After washed in 300 μL PBST washing solution for 5 times, previously prepared and incubated mixture of the fusion proteins and FGF-2 as well as the standard diluted in a gradient are added, in which the preparation of the mixture is as follows: the starting concentration of 12#, 15# and 25# Fc fusion protein is 800000 μM (dissolved in PBS) and diluted in a gradient ratio of 10-fold, and the solutions of the fusion protein are 1:1 mixed with 20 pM VEGF solution, and that is, the starting final concentration of each fusion protein is 400000 pM, and the final concentration of VEGF is 10 pM; the starting concentration of 25# and 26# Fc fusion protein is 200 pM (dissolved in PBS) and diluted in a gradient ratio of 2-fold, and the solutions of the fusion protein are 1:1 mixed with 20 pM FGF-2 solution, and that is, the starting final concentration of each fusion protein is 200 pM, and the final concentration of FGF-2 is 10 pM. The plate is incubated at 37° C. for 2 h and washed in 300 μL PBST washing solution for 5 times before 100 μL VEGF detection antibody solution (100 ng/mL) or 100 μL FGF-2 detection antibody solution (250 ng/mL) is added (R&D systems, which may specifically detect free antibodies against VEGF or FGF-2). The plate is incubated at 37° C. for 2 h and washed in 300 μL PBST washing solution for 5 times, and subsequently, HRP labeled streptavidin (R&D systems) is added (diluted by PBS in 1:200). The plate is incubated at 37° C. for 2 h and washed in 300 μL PBST washing solution for 5 times before the well is developed for an appropriate duration (about 15-30 min) by adding 100 μL developing solution (KPL). Finally, after the development is stopped by adding 100 μL stopping solution (KPL), the absorbance of the ELISA plate is read at a wavelength of 450 nm on an ELISA reader. The relative concentration of free VEGF or FGF-2 in the mixture of the fusion protein and VEGF or FGF-2 is determined.

Figure 5A:
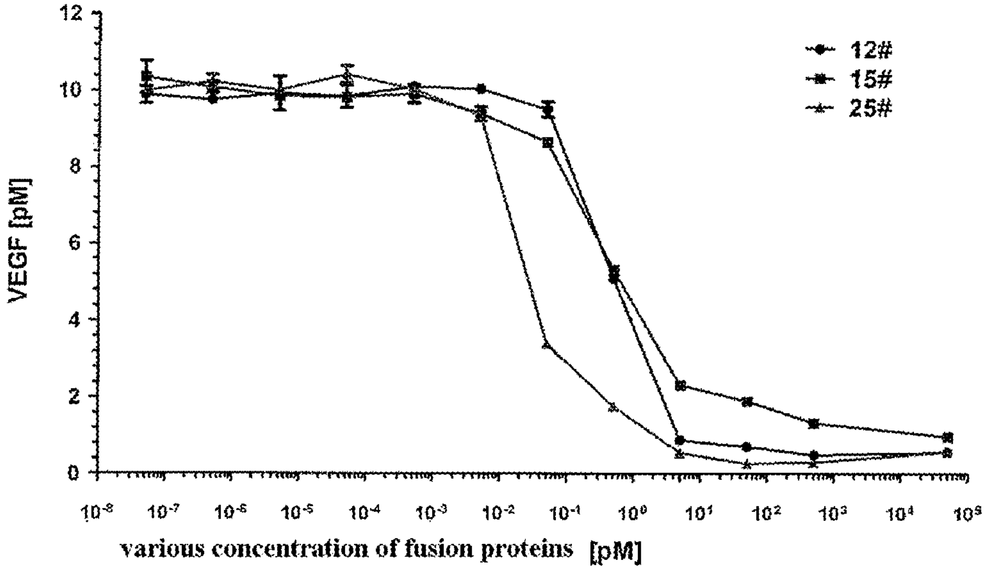
FIG. 5 shows the affinity of VEGF (A) and FGF-2 (B) to the fusion protein.
Figure 5B:
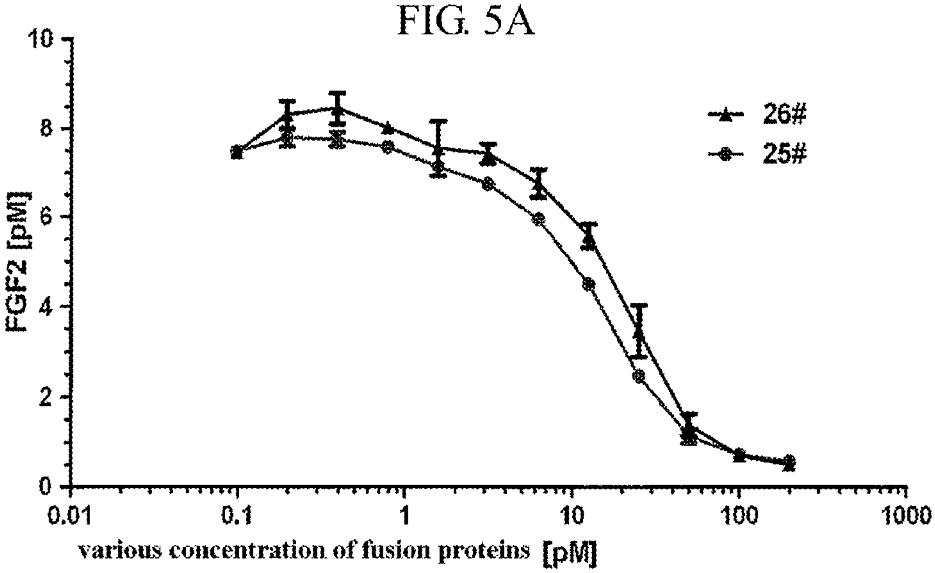
Figure 6A:
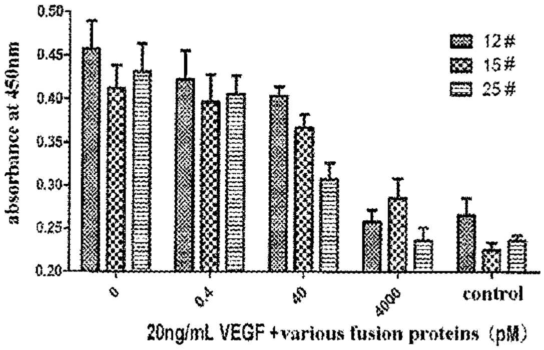
FIG. 6A shows the effect of the fusion protein on HUVEC cell proliferation induced by VEGF.
Figure 6B:
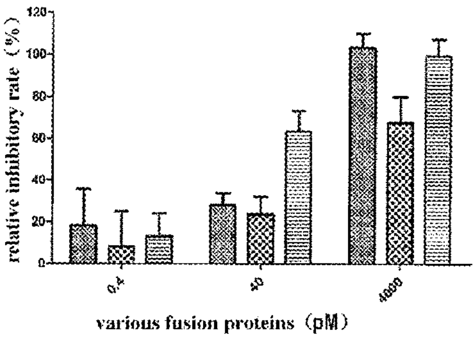
FIG. 6B shows the relative inhibition rates of the fusion protein on HUVEC cell proliferation induced by VEGF.
Figure 6C:
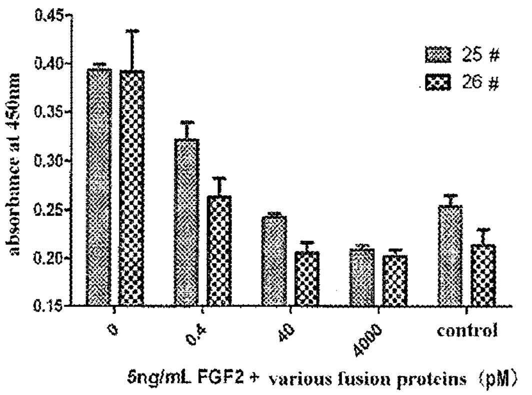
FIG. 6C shows the effect of the fusion protein on HUVEC cell proliferation induced by FGF2.
Figure 6D:
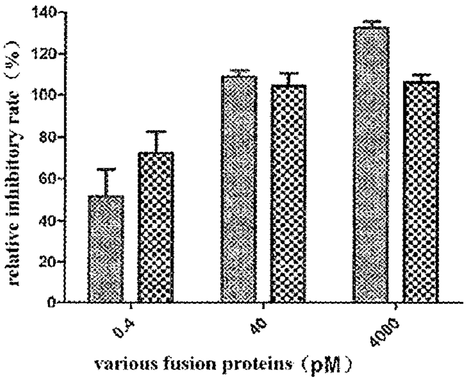
FIG. 6D shows the relative inhibition rates of the fusion protein on HUVEC cell proliferation induced by FGF2.

The affinities of 12#, 15# and 25# fusion protein to VEGF or FGF-2 in a solution system are compared, as seen in FIGS. 5A and 5B. Furthermore, 25# fusion protein is compared with an FGFR-Fc fusion protein (designated as 26#), as seen in FIGS. 5C and 5D. Among others, 26# FGFR-Fc fusion protein comprises the second Ig-like domain of FGFR, the third Ig-like domain of FGFR and Fc region. As demonstrated in this Example, the VEGFR-FGFR-Fc fusion proteins constructed in the present invention (for example 12#, 15# and 25#) have high affinity to both VEGF and FGF-2 in a solution system. The affinity increases as the concentration increases, as indicated by a reduced amount of free VEGF and FGF-2 with an increased concentration of the fusion protein. The affinities of 12#, 15# and 25# VEGFR-FGFR-Fc fusion protein according to the present invention to VEGF or FGF-2 in a solution system are shown in FIG. 5. As demonstrated in this Example, the VEGFR-FGFR fusion proteins as constructed in the present invention have affinity to both VEGF and FGF-2 in a solution system. The affinity increases as the concentration increases, as indicated by a reduced amount of free VEGF and FGF-2.

Example 7

Inhibitory Test for Division on Human Umbilical Vein Endothelial Cell

The inhibitory ability of the fusion proteins on the division of vascular endothelial cells is examined in a division test for human umbilical vein endothelial cell (HUVEC). HUVEC cells (AllCells) are cultured to the exponential growth phase in an HUVEC complete medium (AllCells) at 37° C. in an incubator supplemented with 5% $CO_2$. HUVEC cells are counted after digested by trypsin. 3000 HUVEC cells are inoculated per well in an HUVEC basal medium containing 1% FBS (AllCells) in a 96-well plate. The plate is cultured overnight at 37° C. in an incubator supplemented with 5% $CO_2$. 100 μL VEGF (R&D Systems) solution (final concentration of 20 ng/mL) or FGF-2 (R&D Systems) solution (final concentration of 5 ng/mL) diluted by an HUVEC basal medium containing 1% FBS, as well as 100 μL mixture of various amount of the fusion proteins and FGF-2 (in which the final concentration of the fusion protein is 40 pM, diluted in an HUVEC basal medium containing 1% FBS with a ratio of 1:10, and the final concentration of FGF-2 is 5 ng/mL) are added and cultured for another 3-4 days. Subsequently, the culture medium is taken out and a culture medium containing 10% CCK-8 (DOJINDO) is added for another 2 h of culture before the absorbance of the ELISA plate is read at a wavelength of 450 nm on an ELISA reader. Based on the difference of the absorbance, the inhibitory ability of the fusion proteins on the division of vascular endothelial cells induced by VEGF or FGF-2 is determined.

The effect of the fusion proteins on HUVEC cell division induced by VEGF or FGF-2 and the relative inhibitory rates are shown in FIG. 6. As demonstrated in this Example, the VEGFR-FGFR-Fc fusion proteins as constructed in the present invention (for example 12#, 15# and 25#) have biological activity and function at the cellular level, which can inhibit HUVEC cell division induced by VEGF or FGF-2 and have the binding capacity to VEGF and FGF-2. Such binding capacity increases as the molar concentration increases, as indicated by the inhibition of HUVEC cell division induced by VEGF or FGF-2.

Example 8

Anti-Tumor Effect of the Fusion Protein

This Example shows that the VEGFR-FGFR protein of the present invention has potent anti-tumor effects.

Human lung carcinoma cell line A549 cells ($5\times10^6$ cells/mouse) and human renal carcinoma cell line Caki-1 cells ($2\times10^6$ cells/mouse) are suspended in serum-free medium, and are subsequently subcutaneously (s.c.) injected into the right flanks of 6 to 8 weeks old female, athymic BALB/c nu/nu mice. Tumor volume is calculated twice a week with a caliper by the formula of [tumor volume ($mm^3$)=(length×width×width)/2]. When the volume of tumor reached around 50 $mm^3$, animals are randomized into seven groups (n=10-11). The animals receive intraperitoneally (i.p.) injection of #28 fusion protein and #15 fusion protein at a dose of 10 μM, 2 μM and PBS twice a week.

Figure 8:
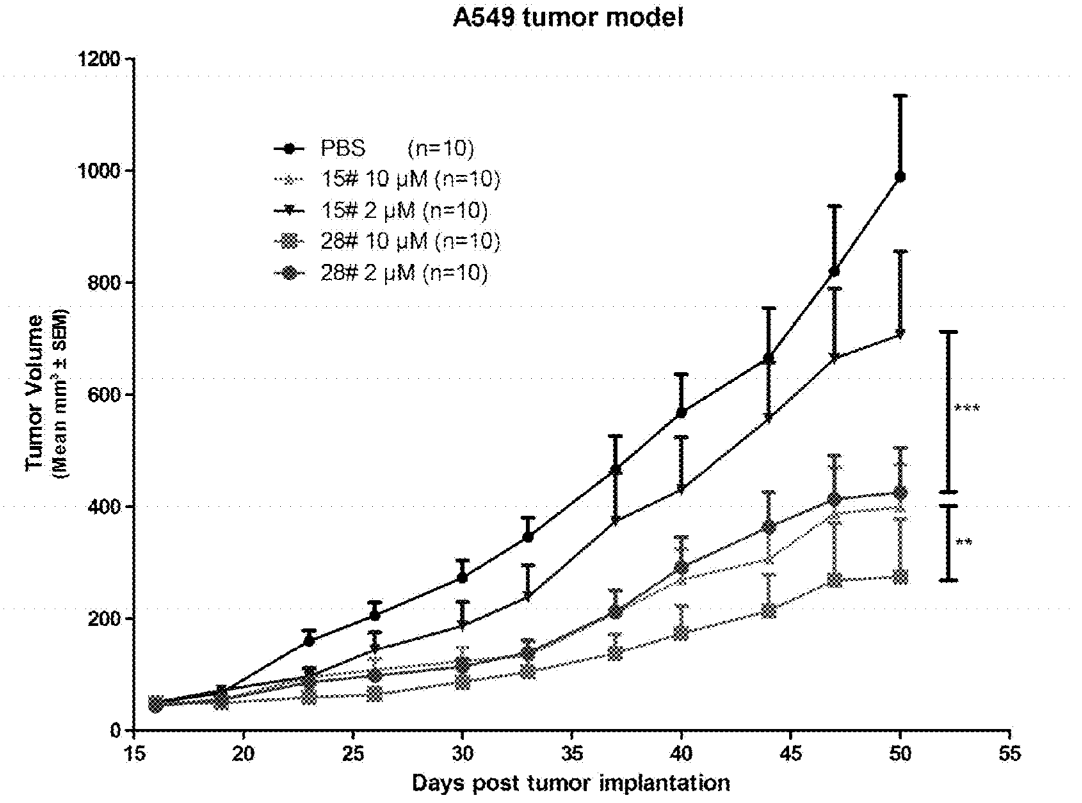
FIG. 8 shows the anti-tumor effect of the fusion protein of the present invention (#28) in a lung carcinoma animal model.

As shown in FIG. 8, in an A549 tumor model, the fusion protein of the present invention (#28) has far greater anti-tumor effect than #15 protein. P values are determined by two-way ANOVA. $P<0.05$ is considered statistically significant.

Figure 9:
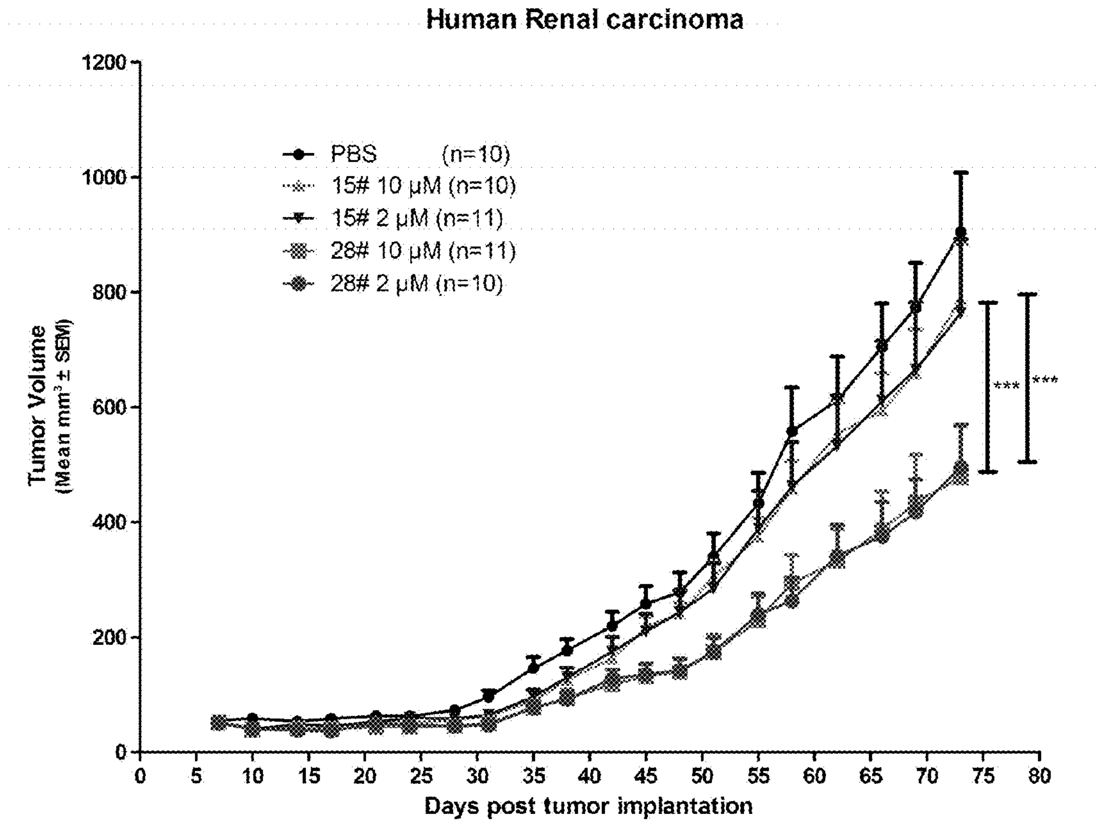
FIG. 9 shows the anti-tumor effect of the fusion protein of the present invention (#28) in a renal carcinoma animal model.

As shown in FIG. 9, in a Caki-1 tumor model, the fusion protein of the present invention (#28) has far greater anti-tumor effect than #15 protein. P values are determined by two-way ANOVA. $P<0.05$ is considered statistically significant.

The present invention has already been illustrated by specific examples. However, it will be appreciated by a person of ordinary skill in the art that the present invention is not limited to each specific embodiments. Various changes and modifications may be made by a person of ordinary skill under the scope of the present invention, and each technical feature mentioned in the specification may be combined without departing from the spirit and scope of the invention. Such changes and modifications fall into the scope of the present invention.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

[1] Hanahan D, Weinberg R A. The hallmarks of cancer. Cell, 2000, 100(1): 57-70.
[2] Hanahan D, Folkman J. Patterns and emerging mechanisms of the angiogenic switch during tumorigenesis. Cell. 1996, 86: 353-64.
[3] Ferrara N, Gerber H P, LeCouter J. The biology of VEGF and its receptors. Nat. Med. 2003, 9: 669-76.
[4] Ferrara N. Vascular endothelial growth factor as a target for anticancer therapy. Oncologist. 2004, 1: 2-10.
[5] Jenab-Wolcott J, Giantonio B J. Bevacizumab: current indications and future development for management of solid tumors. Expert Opin Biol Ther. 2009, 9(4): 507-17.
[6] Summers J, Cohen M H, Keegan P, Pazdur R. FDA drug approval summary: bevacizumab plus interferon for advanced renal cell carcinoma. Oncologist. 2010, 15(1): 104-11.
[7] Hsu J Y, Wakelee H A. Monoclonal antibodies targeting vascular endothelial growth factor: current status and future challenges in cancer therapy. BioDrugs. 2009, 23(5): 289-304.
[8] Krupitskaya Y, Wakelee H A. Ramucirumab, a fully human mAb to the transmembrane signaling tyrosine kinase VEGFR-2 for the potential treatment of cancer. Curr Opin Investig Drugs. 2009, 10(6): 597-605.
[9] Hurwitz H, Fehrenbacher L, Novotny W, Cartwright T, Hainsworth J, Heim W, Berlin J, Baron A, Griffing S, Holmgren E, Ferrara N, Fyfe G, Rogers B, Ross R, Kabbinavar F. Bevacizumab plus irinotecan, fluorouracil, and leucovorin for metastatic colorectal cancer. N Engl J. Med. 2004, 350(23): 2335-42.
[10] Sandler A, Gray R, Perry M C, Brahmer J, Schiller J H, Dowlati A, Lilenbaum R, Johnson D H. Paclitaxel-carboplatin alone or with bevacizumab for non-small-cell lung cancer. N Engl J. Med. 2006, 355(24): 2542-50.
[11] Jenab-Wolcott J, Giantonio B J. Bevacizumab: current indications and future development for management of solid tumors. Expert Opin Biol Ther, 2009, 9(4): 507-17.

[12]. Dorrell M I, Aguilar E, Scheppke L, Barnett F H, Friedlander M. Combination angiostatic therapy completely inhibits ocular and tumor angiogenesis. Proc Natl Acad Sci USA. 2007, 104(3): 967-72.

[13] Casanovas O, Hicklin D J, Bergers G, Hanahan D. Drug resistance by evasion of antiangiogenic targeting of VEGF signaling in late-stage pancreatic islet tumors. Cancer Cell. 2005, 8(4): 299-309.

[14] Welti J C, Gourlaouen M, Powles T, Kudahetti S C, Wilson P, Berney D M, Reynolds A R. Fibroblast growth factor 2 regulates endothelial cell sensitivity to sunitinib. Oncogene. 2010, doi: 10.1038/one.2010.503.

We claim:

1. An angiogenesis-inhibitory fusion protein, comprising two units, wherein one unit comprises a part derived from an extracellular domain of VEGFR and a second unit comprises a part derived from an extracellular domain of FGFR, wherein the part derived from the extracellular domain of VEGFR comprises:

i) a second Ig-like domain of VEGFR1 or VEGFR2 comprising an amino acid sequence having at least 90% identity with amino acids 151 to 214 of SEQ ID NO: 2, or an amino acid sequence having at least 90% identity with amino acids 141 to 207 of SEQ ID NO: 3, and ii) a third Ig-like domain of VEGFR1 or VEGFR2 comprising an amino acid sequence having at least 90% identity with amino acids 230 to 327 of SEQ ID NO: 2, or an amino acid sequence having at least 90% identity with amino acids 224 to 320 of SEQ ID NO: 3; and wherein the part derived from the extracellular domain of FGFR comprises:

i) a part derived from an intermediate functional sequence region of an Ig-like domain of FGFR, ii) a second Ig-like domain of FGFR comprising an amino acid sequence having at least 90% identity with the amino acids 163 to 247 of SEQ ID NO: 1, and/or, iii) a third Ig-like domain of FGFR comprising an amino acid sequence having at least 90% identity with amino acids 270 to 359 of SEQ ID NO: 1;

wherein the part derived from the intermediate functional sequence region of the Ig-like domain of FGFR is a sequence between the first Ig-like domain and the second Ig-like domain of FGFR comprising an amino acid sequence having at least 90% identity amino acids 118 to 162 of SEQ ID NO: 1; and wherein said fusion protein further comprises an Fc region, wherein the Fc region is located closer to the C-terminus of the fusion protein than either of said units.

2. The fusion protein, according to claim 1, which comprises, from the N-terminus to the C-terminus, a part derived from the extracellular domain of VEGFR, and a part derived from the extracellular domain of FGFR.

3. The fusion protein, according to claim 2, wherein the part derived from the extracellular domain of VEGFR comprises, from the N-terminus to the C-terminus, the second Ig-like domain of VEGFR1 or VEGFR2, and the third Ig-like domain of VEGFR1 or VEGFR2; and wherein the part derived from the extracellular domain of FGFR comprises, from the N-terminus to the C-terminus, a part derived from the intermediate functional sequence region of the Ig-like domain of FGFR, the second Ig-like domain of FGFR, and the third Ig-like domain of FGFR.

4. The fusion protein, according to claim 2, wherein the part derived from the extracellular domain of VEGFR further comprises a first Ig-like domain of VEGFR1 or VEGFR2; and wherein the part derived from the extracellular domain of FGFR comprises, from the N-terminus to the C-terminus, a part derived from the intermediate functional sequence region of the Ig-like domain of FGFR, a second Ig-like domain of FGFR, and a third Ig-like domain of FGFR.

5. The fusion protein, according to claim 4, wherein the first Ig-like domain of VEGFR1 comprises the amino acid sequence corresponding to position 32 to position 123 of SEQ ID NO: 2, or wherein the first Ig-like domain of VEGFR2 comprises the amino acid sequence corresponding to position 46 to position 110 of SEQ ID NO: 3.

6. The fusion protein, according to claim 1, wherein the part derived from the extracellular domain of FGFR further comprises a first Ig-like domain of FGFR.

7. The fusion protein, according to claim 6, wherein the first Ig-like domain of FGFR comprises the amino acid sequence corresponding to position 77 to position 118 of SEQ ID NO: 1.

8. The fusion protein, according to claim 1, comprising:

a second Ig-like domain of VEGFR1 comprising the amino acid sequence corresponding to position 151 to position 214 of SEQ ID NO: 2, a third Ig-like domain of VEGFR2 comprising the amino acid sequence corresponding to position 224 to position 320 of SEQ ID NO: 3, a second Ig-like domain of FGFR1 comprising the amino acid sequence corresponding to position 163 to position 247 of SEQ ID NO: 1, and/or a third Ig-like domain of FGFR1 comprising the amino acid sequence corresponding to position 270 to position 359 of SEQ ID NO: 1.

9. The fusion protein, according to claim 1, further comprising a secretory signal peptide region.

10. An isolated nucleic acid molecule encoding a fusion protein of claim 1.

11. A vector comprising a nucleic acid molecule of claim 10.

12. An isolated cell comprising a vector of claim 11.

13. A pharmaceutical composition, comprising a fusion protein of claim 1, and a pharmaceutically acceptable carrier.

14. A method for producing an angiogenesis-inhibitory fusion protein, comprising expressing a fusion protein of claim 1 in a cell in vitro.

15. The fusion protein, according to claim 1, wherein the part derived from the intermediate functional sequence region of the Ig-like domain of FGFR is the sequence between the first Ig-like domain and the second Ig-like domain of FGFR, and wherein said part derived from the intermediate functional sequence region comprises the amino acid sequence corresponding to position 118 to the position 162 of SEQ ID NO: 1.

16. The fusion protein, according to claim 15, wherein the part derived from the intermediate functional sequence region comprises a sequence selected from: an amino acid sequence corresponding to the position 134 to the position 162, the position 145 to the position 162, or the position 151 to the position 162 of SEQ ID NO: 1.

17. A fusion protein that comprises:

(1) a polypeptide having the amino acid sequence of any one of SEQ ID NOs: 18-24;

(2) a polypeptide encoded by the nucleotide sequence of any one of SEQ ID NOs: 35-41; or (3) a polypeptide having the amino acid sequence having at least 90% identity with an amino acid sequence of any one of SEQ ID NOs: 18-24.

18. An isolated nucleic acid molecule comprising the nucleotide sequence of one of SEQ ID NOs: 35-41.

* * * * *

UNITED STATES PATENT AND TRADEMARK OFFICE

CERTIFICATE OF CORRECTION

PATENT NO. : 9,522,949 B2
APPLICATION NO. : 13/842667
DATED : December 20, 2016
INVENTOR(S) : Jianmin Fang et al.

It is certified that error appears in the above-identified patent and that said Letters Patent is hereby corrected as shown below:

In the Specification

Column 1,
Line 16-17, "Mar. 14, 2013Mar. 3, 2015" should read --March 3, 2015--.

Column 12,
Line 16, "protein EGFR" should read --protein FGFR--.

Column 17,
Line 62, "like);" should read --like.);--.

Column 22,
Line 61, "protein-proteins" should read --proteins--.

Column 28,
Line 29, "214 construct" should read --21# construct--.

Column 31,
Line 27, "adding 1004" should read --adding 100µL--.

Column 31,
Line 52, "in 3004" should read --in 300µL--.

Column 31,
Line 58, "1004" should read --100µL--.

Column 33,
Line 42, "determined" should read --determined.--.

Signed and Sealed this
Ninth Day of May, 2017

Michelle K. Lee
*Director of the United States Patent and Trademark Office*

Column 34,
Line 7, “1004” should read --100μL--.

Column 181,
Line 22, “NO: 3, and” should read --NO: 3,--.

SEQUENCE LISTING

```
<160> NUMBER OF SEQ ID NOS: 76

<210> SEQ ID NO 1
<211> LENGTH: 820
<212> TYPE: PRT
<213> ORGANISM: Homo sapiens
<220> FEATURE:
<221> NAME/KEY: Ig1_FGFR
<222> LOCATION: (40)..(118)
<220> FEATURE:
<221> NAME/KEY: Ig2_FGFR
<222> LOCATION: (163)..(247)
<220> FEATURE:
<221> NAME/KEY: Ig3_FGFR
<222> LOCATION: (270)..(359)

<400> SEQUENCE: 1

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
```

-continued

```
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365

Ser Pro Leu Tyr Leu Glu Ile Ile Ile Tyr Cys Thr Gly Ala Phe Leu
    370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                405                 410                 415

Lys Ser Ile Pro Leu Arg Arg Gln Val Thr Val Ser Ala Asp Ser Ser
            420                 425                 430

Ala Ser Met Asn Ser Gly Val Leu Leu Val Arg Pro Ser Arg Leu Ser
        435                 440                 445

Ser Ser Gly Thr Pro Met Leu Ala Gly Val Ser Glu Tyr Glu Leu Pro
    450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
        515                 520                 525

Glu Met Glu Met Met Lys Met Ile Gly Lys His Lys Asn Ile Ile Asn
    530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
        595                 600                 605

Met Glu Tyr Leu Ala Ser Lys Lys Cys Ile His Arg Asp Leu Ala Ala
    610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
        675                 680                 685

Trp Glu Ile Phe Thr Leu Gly Gly Ser Pro Tyr Pro Gly Val Pro Val
    690                 695                 700
```

```
Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
        755                 760                 765

Met Pro Leu Asp Gln Tyr Ser Pro Ser Phe Pro Asp Thr Arg Ser Ser
    770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820


<210> SEQ ID NO 2
<211> LENGTH: 1338
<212> TYPE: PRT
<213> ORGANISM: Homo sapiens

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
```

```
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670
```

-continued

```
Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile  Ser Tyr Ser Phe Gln  Val Ala Arg
        995                 1000                1005

Gly Met  Glu Phe Leu Ser Ser  Arg Lys Cys Ile His  Arg Asp Leu
    1010                1015                1020

Ala Ala  Arg Asn Ile Leu Leu  Ser Glu Asn Asn Val  Val Lys Ile
    1025                1030                1035

Cys Asp  Phe Gly Leu Ala Arg  Asp Ile Tyr Lys Asn  Pro Asp Tyr
    1040                1045                1050

Val Arg  Lys Gly Asp Thr Arg  Leu Pro Leu Lys Trp  Met Ala Pro
    1055                1060                1065

Glu Ser  Ile Phe Asp Lys Ile  Tyr Ser Thr Lys Ser  Asp Val Trp
    1070                1075                1080
```

-continued

```
Ser Tyr  Gly Val Leu Leu Trp  Glu Ile Phe Ser Leu  Gly Gly Ser
    1085                 1090                 1095

Pro Tyr  Pro Gly Val Gln Met  Asp Glu Asp Phe Cys  Ser Arg Leu
    1100                 1105                 1110

Arg Glu  Gly Met Arg Met Arg  Ala Pro Glu Tyr Ser  Thr Pro Glu
    1115                 1120                 1125

Ile Tyr  Gln Ile Met Leu Asp  Cys Trp His Arg Asp  Pro Lys Glu
    1130                 1135                 1140

Arg Pro  Arg Phe Ala Glu Leu  Val Glu Lys Leu Gly  Asp Leu Leu
    1145                 1150                 1155

Gln Ala  Asn Val Gln Gln Asp  Gly Lys Asp Tyr Ile  Pro Ile Asn
    1160                 1165                 1170

Ala Ile  Leu Thr Gly Asn Ser  Gly Phe Thr Tyr Ser  Thr Pro Ala
    1175                 1180                 1185

Phe Ser  Glu Asp Phe Phe Lys  Glu Ser Ile Ser Ala  Pro Lys Phe
    1190                 1195                 1200

Asn Ser  Gly Ser Ser Asp Asp  Val Arg Tyr Val Asn  Ala Phe Lys
    1205                 1210                 1215

Phe Met  Ser Leu Glu Arg Ile  Lys Thr Phe Glu Glu  Leu Leu Pro
    1220                 1225                 1230

Asn Ala  Thr Ser Met Phe Asp  Asp Tyr Gln Gly Asp  Ser Ser Thr
    1235                 1240                 1245

Leu Leu  Ala Ser Pro Met Leu  Lys Arg Phe Thr Trp  Thr Asp Ser
    1250                 1255                 1260

Lys Pro  Lys Ala Ser Leu Lys  Ile Asp Leu Arg Val  Thr Ser Lys
    1265                 1270                 1275

Ser Lys  Glu Ser Gly Leu Ser  Asp Val Ser Arg Pro  Ser Phe Cys
    1280                 1285                 1290

His Ser  Ser Cys Gly His Val  Ser Glu Gly Lys Arg  Arg Phe Thr
    1295                 1300                 1305

Tyr Asp  His Ala Glu Leu Glu  Arg Lys Ile Ala Cys  Cys Ser Pro
    1310                 1315                 1320

Pro Pro  Asp Tyr Asn Ser Val  Val Leu Tyr Ser Thr  Pro Pro Ile
    1325                 1330                 1335


<210> SEQ ID NO 3
<211> LENGTH: 1356
<212> TYPE: PRT
<213> ORGANISM: Homo sapiens

<400> SEQUENCE: 3

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110
```

-continued

```
Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525
```

```
Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
    770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
    850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
    930                 935                 940

Phe Arg Gln Gly Lys Asp Tyr Val Gly Ala Ile Pro Val Asp Leu Lys
```

-continued

```
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
            980                 985                 990

Glu Asp Leu Tyr Lys Asp Phe Leu  Thr Leu Glu His Leu  Ile Cys Tyr
        995                 1000                1005

Ser Phe  Gln Val Ala Lys Gly  Met Glu Phe Leu Ala  Ser Arg Lys
    1010                 1015                1020

Cys Ile  His Arg Asp Leu Ala  Ala Arg Asn Ile Leu  Leu Ser Glu
    1025                 1030                1035

Lys Asn  Val Val Lys Ile Cys  Asp Phe Gly Leu Ala  Arg Asp Ile
    1040                 1045                1050

Tyr Lys  Asp Pro Asp Tyr Val  Arg Lys Gly Asp Ala  Arg Leu Pro
    1055                 1060                1065

Leu Lys  Trp Met Ala Pro Glu  Thr Ile Phe Asp Arg  Val Tyr Thr
    1070                 1075                1080

Ile Gln  Ser Asp Val Trp Ser  Phe Gly Val Leu Leu  Trp Glu Ile
    1085                 1090                1095

Phe Ser  Leu Gly Ala Ser Pro  Tyr Pro Gly Val Lys  Ile Asp Glu
    1100                 1105                1110

Glu Phe  Cys Arg Arg Leu Lys  Glu Gly Thr Arg Met  Arg Ala Pro
    1115                 1120                1125

Asp Tyr  Thr Thr Pro Glu Met  Tyr Gln Thr Met Leu  Asp Cys Trp
    1130                 1135                1140

His Gly  Glu Pro Ser Gln Arg  Pro Thr Phe Ser Glu  Leu Val Glu
    1145                 1150                1155

His Leu  Gly Asn Leu Leu Gln  Ala Asn Ala Gln Gln  Asp Gly Lys
    1160                 1165                1170

Asp Tyr  Ile Val Leu Pro Ile  Ser Glu Thr Leu Ser  Met Glu Glu
    1175                 1180                1185

Asp Ser  Gly Leu Ser Leu Pro  Thr Ser Pro Val Ser  Cys Met Glu
    1190                 1195                1200

Glu Glu  Glu Val Cys Asp Pro  Lys Phe His Tyr Asp  Asn Thr Ala
    1205                 1210                1215

Gly Ile  Ser Gln Tyr Leu Gln  Asn Ser Lys Arg Lys  Ser Arg Pro
    1220                 1225                1230

Val Ser  Val Lys Thr Phe Glu  Asp Ile Pro Leu Glu  Glu Pro Glu
    1235                 1240                1245

Val Lys  Val Ile Pro Asp Asp  Asn Gln Thr Asp Ser  Gly Met Val
    1250                 1255                1260

Leu Ala  Ser Glu Glu Leu Lys  Thr Leu Glu Asp Arg  Thr Lys Leu
    1265                 1270                1275

Ser Pro  Ser Phe Gly Gly Met  Val Pro Ser Lys Ser  Arg Glu Ser
    1280                 1285                1290

Val Ala  Ser Glu Gly Ser Asn  Gln Thr Ser Gly Tyr  Gln Ser Gly
    1295                 1300                1305

Tyr His  Ser Asp Asp Thr Asp  Thr Thr Val Tyr Ser  Ser Glu Glu
    1310                 1315                1320

Ala Glu  Leu Leu Lys Leu Ile  Glu Ile Gly Val Gln  Thr Gly Ser
    1325                 1330                1335

Thr Ala  Gln Ile Leu Gln Pro  Asp Ser Gly Thr Thr  Leu Ser Ser
    1340                 1345                1350
```

Pro Pro Val
1355

<210> SEQ ID NO 4
<211> LENGTH: 5911
<212> TYPE: DNA
<213> ORGANISM: Homo sapiens

<400> SEQUENCE: 4
agatgcaggg gcgcaaacgc caaaggagac caggctgtag gaagagaagg gcagagcgcc 60
ggacagctcg gcccgctccc cgtcctttgg ggccgcggct ggggaactac aaggcccagc 120
aggcagctgc agggggcgga ggcggaggag ggaccagcgc gggtgggagt gagagagcga 180
gccctcgcgc cccgccggcg catagcgctc ggagcgctct tgcggccaca ggcgcggcgt 240
cctcggcggc gggcggcagc tagcgggagc cgggacgccg gtgcagccgc agcgcgcgga 300
ggaacccggg tgtgccggga gctgggcggc cacgtccgga cgggaccgag acccctcgta 360
gcgcattgcg gcgacctcgc cttccccggc cgcgagcgcg ccgctgcttg aaaagccgcg 420
gaacccaagg acttttctcc ggtccgagct cggggcgccc cgcagggcgc acggtacccg 480
tgctgcagtc gggcacgccg cggcgccggg gcctccgcag ggcgatggag cccggtctgc 540
aaggaaagtg aggcgccgcc gctgcgttct ggaggagggg ggcacaaggt ctggagaccc 600
cgggtggcgg acgggagccc tccccccgcc ccgcctccgg ggcaccagct ccggctccat 660
tgttcccgcc cgggctggag gcgccgagca ccgagcgccg ccgggagtcg agcgccggcc 720
gcggagctct tgcgaccccg ccaggacccg aacagagccc gggggcggcg ggccggagcc 780
ggggacgcgg gcacacgccc gctcgcacaa gccacggcgg actctcccga ggcggaacct 840
ccacgccgag cgagggtcag tttgaaaagg aggatcgagc tcactgtgga gtatccatgg 900
agatgtggag ccttgtcacc aacctctaac tgcagaactg ggatgtggag ctggaagtgc 960
ctcctcttct gggctgtgct ggtcacagcc acactctgca ccgctaggcc gtccccgacc 1020
ttgcctgaac aagcccagcc ctggggagcc cctgtggaag tggagtcctt cctggtccac 1080
cccggtgacc tgctgcagct tcgctgtcgg ctgcgggacg atgtgcagag catcaactgg 1140
ctgcgggacg gggtgcagct ggcggaaagc aaccgcaccc gcatcacagg ggaggaggtg 1200
gaggtgcagg actccgtgcc cgcagactcc ggcctctatg cttgcgtaac cagcagcccc 1260
tcgggcagtg acaccaccta cttctccgtc aatgtttcag atgctctccc ctcctcggag 1320
gatgatgatg atgatgatga ctcctcttca gaggagaaag aaacagataa caccaaacca 1380
aaccccgtag ctccatattg gacatcccca gaaaagatgg aaaagaaatt gcatgcagtg 1440
ccggctgcca agacagtgaa gttcaaatgc ccttccagtg ggaccccaaa ccccacactg 1500
cgctggttga aaaatggcaa agaattcaaa cctgaccaca gaattggagg ctacaaggtc 1560
cgttatgcca cctggagcat cataatggac tctgtggtgc cctctgacaa gggcaactac 1620
acctgcattg tggagaatga gtacggcagc atcaaccaca cataccagct ggatgtcgtg 1680
gagcggtccc ctcaccggcc catcctgcaa gcagggttgc ccgccaacaa aacagtggcc 1740
ctgggtagca acgtggagtt catgtgtaag gtgtacagtg acccgcagcc gcacatccag 1800
tggctaaagc acatcgaggt gaatgggagc aagattggcc cagacaacct gccttatgtc 1860
cagatcttga agactgctgg agttaatacc accgacaaag agatggaggt gcttcactta 1920
agaaatgtct cctttgagga cgcaggggag tatacgtgct tggcgggtaa ctctatcgga 1980
ctctcccatc actctgcatg gttgaccgtt ctggaagccc tggaagagag gccggcagtg 2040

-continued

```
atgacctcgc ccctgtacct ggagatcatc atctattgca caggggcctt cctcatctcc   2100
tgcatggtgg ggtcggtcat cgtctacaag atgaagagtg gtaccaagaa gagtgacttc   2160
cacagccaga tggctgtgca caagctggcc aagagcatcc ctctgcgcag acaggtaaca   2220
gtgtctgctg actccagtgc atccatgaac tctggggttc ttctggttcg gccatcacgg   2280
ctctcctcca gtgggactcc catgctagca ggggtctctg agtatgagct tcccgaagac   2340
cctcgctggg agctgcctcg ggacagactg gtcttaggca aacccctggg agagggctgc   2400
tttgggcagg tggtgttggc agaggctatc gggctggaca aggacaaacc caaccgtgtg   2460
accaaagtgg ctgtgaagat gttgaagtcg gacgcaacag agaaagactt gtcagacctg   2520
atctcagaaa tggagatgat gaagatgatc gggaagcata agaatatcat caacctgctg   2580
ggggcctgca cgcaggatgg tcccttgtat gtcatcgtgg agtatgcctc caagggcaac   2640
ctgcgggagt acctgcaggc ccggaggccc ccagggctgg aatactgcta caaccccagc   2700
cacaacccag aggagcagct ctcctccaag gacctggtgt cctgcgccta ccaggtggcc   2760
cgaggcatgg agtatctggc ctccaagaag tgcatacacc gagacctggc agccaggaat   2820
gtcctggtga cagaggacaa tgtgatgaag atagcagact ttggcctcgc acgggacatt   2880
caccacatcg actactataa aaagacaacc aacggccgac tgcctgtgaa gtggatggca   2940
cccgaggcat tatttgaccg gatctacacc caccagagtg atgtgtggtc tttcggggtg   3000
ctcctgtggg agatcttcac tctgggcggc tccccatacc ccggtgtgcc tgtggaggaa   3060
cttttcaagc tgctgaagga gggtcaccgc atggacaagc ccagtaactg caccaacgag   3120
ctgtacatga tgatgcggga ctgctggcat gcagtgccct cacagagacc caccttcaag   3180
cagctggtgg aagacctgga ccgcatcgtg gccttgacct ccaaccagga gtacctggac   3240
ctgtccatgc ccctggacca gtactccccc agctttcccg acacccggag ctctacgtgc   3300
tcctcagggg aggattccgt cttctctcat gagccgctgc ccgaggagcc ctgcctgccc   3360
cgacacccag cccagcttgc caatggcgga ctcaaacgcc gctgactgcc acccacacgc   3420
cctccccaga ctccaccgtc agctgtaacc ctcacccaca gcccctgctg ggcccaccac   3480
ctgtccgtcc ctgtcccctt tcctgctggc aggagccggc tgcctaccag gggccttcct   3540
gtgtggcctg ccttcacccc actcagctca cctctccctc cacctcctct ccacctgctg   3600
gtgagaggtg caaagaggca gatctttgct gccagccact tcatcccctc ccagatgttg   3660
gaccaacacc cctccctgcc accaggcact gcctggaggg cagggagtgg gagccaatga   3720
acaggcatgc aagtgagagc ttcctgagct ttctcctgtc ggtttggtct gttttgcctt   3780
cacccataag cccctcgcac tctggtggca ggtgccttgt cctcagggct acagcagtag   3840
ggaggtcagt gcttcgtgcc tcgattgaag gtgacctctg ccccagatag gtggtgccag   3900
tggcttatta attccgatac tagtttgctt tgctgaccaa atgcctggta ccagaggatg   3960
gtgaggcgaa ggccaggttg gggcagtgt tgtggccctg gggcccagcc ccaaactggg   4020
ggctctgtat atagctatga agaaaacaca aagtgtataa atctgagtat atatttacat   4080
gtctttttaa aagggtcgtt accagagatt tacccatcgg gtaagatgct cctggtggct   4140
gggaggcatc agttgctata tattaaaaac aaaaaagaaa aaaaaggaaa atgtttttaa   4200
aaaggtcata tattttttgc tacttttgct gttttatttt tttaaattat gttctaaacc   4260
tattttcagt ttaggtccct caataaaaat tgctgctgct tcatttatct atgggctgta   4320
tgaaaagggt gggaatgtcc actggaaaga agggacaccc acgggccctg gggctaggtc   4380
```

-continued

```
tgtcccgagg gcaccgcatg ctcccggcgc aggttccttg taacctcttc ttcctaggtc   4440
ctgcacccag acctcacgac gcacctcctg cctctccgct gcttttggaa agtcagaaaa   4500
agaagatgtc tgcttcgagg gcaggaaccc catccatgca gtagaggcgc tgggcagaga   4560
gtcaaggccc agcagccatc gaccatggat ggtttcctcc aaggaaaccg gtggggttgg   4620
gctggggagg gggcacctac ctaggaatag ccacggggta gagctacagt gattaagagg   4680
aaagcaaggg cgcggttgct cacgcctgta atcccagcac tttgggacac cgaggtgggc   4740
agatcacttc aggtcaggag tttgagacca gcctggccaa cttagtgaaa ccccatctct   4800
actaaaaatg caaaaattat ccaggcatgg tggcacacgc ctgtaatccc agctccacag   4860
gaggctgagg cagaatccct tgaagctggg aggcggaggt tgcagtgagc cgagattgcg   4920
ccattgcact ccagcctggg caacagagaa aacaaaaagg aaaacaaatg atgaaggtct   4980
gcagaaactg aaacccagac atgtgtctgc cccctctatg tgggcatggt tttgccagtg   5040
cttctaagtg caggagaaca tgtcacctga ggctagtttt gcattcaggt ccctggcttc   5100
gtttcttgtt ggtatgcctc cccagatcgt ccttcctgta tccatgtgac cagactgtat   5160
ttgttgggac tgtcgcagat cttggcttct tacagttctt cctgtccaaa ctccatcctg   5220
tccctcagga acggggggaa aattctccga atgtttttgg tttttggct gcttggaatt   5280
tacttctgcc acctgctggt catcactgtc ctcactaagt ggattctggc tcccccgtac   5340
ctcatggctc aaactaccac tcctcagtcg ctatattaaa gcttatattt tgctggatta   5400
ctgctaaata caaaagaaag ttcaatatgt tttcatttct gtagggaaaa tgggattgct   5460
gctttaaatt tctgagctag ggattttttg gcagctgcag tgttggcgac tattgtaaaa   5520
ttctctttgt ttctctctgt aaatagcacc tgctaacatt acaatttgta tttatgttta   5580
aagaaggcat catttggtga acagaactag gaaatgaatt tttagctctt aaaagcattt   5640
gctttgagac cgcacaggag tgtctttcct tgtaaaacag tgatgataat ttctgccttg   5700
gccctacctt gaagcaatgt tgtgtgaagg gatgaagaat ctaaaagtct tcataagtcc   5760
ttgggagagg tgctagaaaa atataaggca ctatcataat tacagtgatg tccttgctgt   5820
tactactcaa atcacccaca aatttcccca aagactgcgc tagctgtcaa ataaaagaca   5880
gtgaaattga cctgaaaaaa aaaaaaaaaa a                                  5911
```

<210> SEQ ID NO 5
<211> LENGTH: 7123
<212> TYPE: DNA
<213> ORGANISM: Homo sapiens

<400> SEQUENCE: 5

```
atcgaggtcc gcgggaggct cggagcgcgc caggcggaca ctcctctcgg ctcctccccg     60
gcagcggcgg cggctcggag cgggctccgg ggctcgggtg cagcggccag cgggcgcctg    120
gcggcgagga ttacccgggg aagtggttgt ctcctggctg gagccgcgag acgggcgctc    180
agggcgcggg gccggcggcg gcgaacgaga ggacggactc tggcggccgg gtcgttggcc    240
gcggggagcg cgggcaccgg gcgagcaggc cgcgtcgcgc tcaccatggt cagctactgg    300
gacaccgggg tcctgctgtg cgcgctgctc agctgtctgc ttctcacagg atctagttca    360
ggttcaaaat taaaagatcc tgaactgagt ttaaaaggca cccagcacat catgcaagca    420
ggccagacac tgcatctcca atgcaggggg gaagcagccc ataaatggtc tttgcctgaa    480
atggtgagta aggaaagcga aaggctgagc ataactaaat ctgcctgtgg aagaaatggc    540
aaacaattct gcagtacttt aaccttgaac acagctcaag caaaccacac tggcttctac    600
```

-continued

```
agctgcaaat atctagctgt acctacttca aagaagaagg aaacagaatc tgcaatctat    660
atatttatta gtgatacagg tagacctttc gtagagatgt acagtgaaat ccccgaaatt    720
atacacatga ctgaaggaag ggagctcgtc attccctgcc gggttacgtc acctaacatc    780
actgttactt taaaaaagtt tccacttgac actttgatcc ctgatggaaa acgcataatc    840
tgggacagta gaaagggctt catcatatca aatgcaacgt acaaagaaat agggcttctg    900
acctgtgaag caacagtcaa tgggcatttg tataagacaa actatctcac acatcgacaa    960
accaatacaa tcatagatgt ccaaataagc acaccacgcc cagtcaaatt acttagaggc   1020
catactcttg tcctcaattg tactgctacc actcccttga acacgagagt tcaaatgacc   1080
tggagttacc ctgatgaaaa aaataagaga gcttccgtaa ggcgacgaat tgaccaaagc   1140
aattcccatg ccaacatatt ctacagtgtt cttactattg acaaaatgca gaacaaagac   1200
aaaggacttt atacttgtcg tgtaaggagt ggaccatcat tcaaatctgt taacacctca   1260
gtgcatatat atgataaagc attcatcact gtgaaacatc gaaaacagca ggtgcttgaa   1320
accgtagctg gcaagcggtc ttaccggctc tctatgaaag tgaaggcatt tccctcgccg   1380
gaagttgtat ggttaaaaga tggggttacct gcgactgaga aatctgctcg ctatttgact   1440
cgtggctact cgttaattat caaggacgta actgaagagg atgcagggaa ttatacaatc   1500
ttgctgagca taaaacagtc aaatgtgttt aaaaacctca ctgccactct aattgtcaat   1560
gtgaaacccc agatttacga aaaggccgtg tcatcgtttc cagacccggc tctctaccca   1620
ctgggcagca gacaaatcct gacttgtacc gcatatggta tccctcaacc tacaatcaag   1680
tggttctggc acccctgtaa ccataatcat tccgaagcaa ggtgtgactt ttgttccaat   1740
aatgaagagt cctttatcct ggatgctgac agcaacatgg gaaacagaat tgagagcatc   1800
actcagcgca tggcaataat agaaggaaag aataagatgg ctagcacctt ggttgtggct   1860
gactctagaa tttctggaat ctacatttgc atagcttcca ataaagttgg gactgtggga   1920
agaaacataa gcttttatat cacagatgtg ccaaatgggt ttcatgttaa cttggaaaaa   1980
atgccgacgg aaggagagga cctgaaactg tcttgcacag ttaacaagtt cttatacaga   2040
gacgttactt ggattttact gcggacagtt aataacagaa caatgcacta cagtattagc   2100
aagcaaaaaa tggccatcac taaggagcac tccatcactc ttaatcttac catcatgaat   2160
gtttccctgc aagattcagg cacctatgcc tgcagagcca ggaatgtata cacaggggaa   2220
gaaatcctcc agaagaaaga aattacaatc agagatcagg aagcaccata cctcctgcga   2280
aacctcagtg atcacacagt ggccatcagc agttccacca ctttagactg tcatgctaat   2340
ggtgtccccg agcctcagat cacttggttt aaaaacaacc acaaaataca acaagagcct   2400
ggaattattt taggaccagg aagcagcacg ctgtttattg aaagagtcac agaagaggat   2460
gaaggtgtct atcactgcaa agccaccaac cagaagggct ctgtggaaag ttcagcatac   2520
ctcactgttc aaggaacctc ggacaagtct aatctggagc tgatcactct aacatgcacc   2580
tgtgtggctg cgactctctt ctggctccta ttaaccctct ttatccgaaa aatgaaaagg   2640
tcttcttctg aaataaagac tgactaccta tcaattataa tggacccaga tgaagttcct   2700
ttggatgagc agtgtgagcg gctcccttat gatgccagca agtgggagtt tgcccgggag   2760
agacttaaac tgggcaaatc acttggaaga ggggcttttg gaaaagtggt tcaagcatca   2820
gcatttggca ttaagaaatc acctacgtgc cggactgtgg ctgtgaaaat gctgaaagag   2880
ggggccacgg ccagcgagta caaagctctg atgactgagc taaaaatctt gacccacatt   2940
```

-continued

```
ggccaccatc tgaacgtggt taacctgctg ggagcctgca ccaagcaagg agggcctctg   3000
atggtgattg ttgaatactg caaatatgga aatctctcca actacctcaa gagcaaacgt   3060
gacttatttt ttctcaacaa ggatgcagca ctacacatgg agcctaagaa agaaaaaatg   3120
gagccaggcc tggaacaagg caagaaacca agactagata gcgtcaccag cagcgaaagc   3180
tttgcgagct ccggctttca ggaagataaa agtctgagtg atgttgagga agaggaggat   3240
tctgacggtt tctacaagga gcccatcact atggaagatc tgatttctta cagttttcaa   3300
gtggccagag gcatggagtt cctgtcttcc agaaagtgca ttcatcggga cctggcagcg   3360
agaaacattc ttttatctga gaacaacgtg gtgaagattt gtgattttgg ccttgcccgg   3420
gatatttata agaaccccga ttatgtgaga aaaggagata ctcgacttcc tctgaaatgg   3480
atggctcctg aatctatctt tgacaaaatc tacagcacca agagcgacgt gtggtcttac   3540
ggagtattgc tgtgggaaat cttctcctta ggtgggtctc catacccagg agtacaaatg   3600
gatgaggact tttgcagtcg cctgagggaa ggcatgagga tgagagctcc tgagtactct   3660
actcctgaaa tctatcagat catgctggac tgctggcaca gagacccaaa agaaaggcca   3720
agatttgcag aacttgtgga aaaactaggt gatttgcttc aagcaaatgt acaacaggat   3780
ggtaaagact acatcccaat caatgccata ctgacaggaa atagtgggtt tacatactca   3840
actcctgcct tctctgagga cttcttcaag gaaagtattt cagctccgaa gtttaattca   3900
ggaagctctg atgatgtcag atacgtaaat gctttcaagt tcatgagcct ggaaagaatc   3960
aaaacctttg aagaactttt accgaatgcc acctccatgt ttgatgacta ccagggcgac   4020
agcagcactc tgttggcctc tcccatgctg aagcgcttca cctggactga cagcaaaccc   4080
aaggcctcgc tcaagattga cttgagagta accagtaaaa gtaaggagtc ggggctgtct   4140
gatgtcagca ggcccagttt ctgccattcc agctgtgggc acgtcagcga aggcaagcgc   4200
aggttcacct acgaccacgc tgagctggaa aggaaaatcg cgtgctgctc cccgccccca   4260
gactacaact cggtggtcct gtactccacc ccacccatct agagtttgac acgaagcctt   4320
atttctagaa gcacatgtgt atttataccc ccaggaaact agcttttgcc agtattatgc   4380
atatataagt ttacaccttt atctttccat gggagccagc tgctttttgt gattttttta   4440
atagtgcttt tttttttttg actaacaaga atgtaactcc agatagagaa atagtgacaa   4500
gtgaagaaca ctactgctaa atcctcatgt tactcagtgt tagagaaatc cttcctaaac   4560
ccaatgactt ccctgctcca acccccgcca cctcagggca cgcaggacca gtttgattga   4620
ggagctgcac tgatcaccca atgcatcacg taccccactg ggccagccct gcagcccaaa   4680
acccagggca acaagcccgt tagccccagg gatcactggc tggcctgagc aacatctcgg   4740
gagtcctcta gcaggcctaa gacatgtgag gaggaaaagg aaaaaaagca aaaagcaagg   4800
gagaaaagag aaaccgggag aaggcatgag aaagaatttg agacgcacca tgtgggcacg   4860
gagggggacg gggctcagca atgccatttc agtggcttcc cagctctgac ccttctacat   4920
ttgagggccc agccaggagc agatggacag cgatgagggg acattttctg gattctggga   4980
ggcaagaaaa ggacaaatat ctttttttgga actaaagcaa attttagaac tttacctatg   5040
gaagtggttc tatgtccatt ctcattcgtg gcatgttttg atttgtagca ctgagggtgg   5100
cactcaactc tgagcccata cttttggctc ctctagtaag atgcactgaa aacttagcca   5160
gagttaggtt gtctccaggc catgatggcc ttacactgaa aatgtcacat tctattttgg   5220
gtattaatat atagtccaga cacttaactc aatttcttgg tattattctg ttttgcacag   5280
ttagttgtga aagaaagctg agaagaatga aaatgcagtc ctgaggagag gagttttctc   5340
```

```
catatcaaaa cgagggctga tggaggaaaa aggtcaataa ggtcaaggga aaaccccgtc   5400
tctataccaa ccaaaccaat tcaccaacac agttgggacc caaaacacag gaagtcagtc   5460
acgtttcctt ttcatttaat ggggattcca ctatctcaca ctaatctgaa aggatgtgga   5520
agagcattag ctggcgcata ttaagcactt taagctcctt gagtaaaaag gtggtatgta   5580
atttatgcaa ggtatttctc cagttgggac tcaggatatt agttaatgag ccatcactag   5640
aagaaaagcc cattttcaac tgctttgaaa cttgcctggg gtctgagcat gatgggaata   5700
gggagacagg gtaggaaagg gcgcctactc ttcagggtct aaagatcaag tgggccttgg   5760
atcgctaagc tggctctgtt tgatgctatt tatgcaagtt agggtctatg tatttatgat   5820
gtctgcacct tctgcagcca gtcagaagct ggagaggcaa cagtggattg ctgcttcttg   5880
gggagaagag tatgcttcct tttatccatg taatttaact gtagaacctg agctctaagt   5940
aaccgaagaa tgtatgcctc tgttcttatg tgccacatcc ttgtttaaag gctctctgta   6000
tgaagagatg ggaccgtcat cagcacattc cctagtgagc ctactggctc ctggcagcgg   6060
cttttgtgga agactcacta gccagaagag aggagtggga cagtcctctc caccaagatc   6120
taaatccaaa caaaagcagg ctagagccag aagagaggac aaatctttgt tcttcctctt   6180
ctttacatac gcaaaccacc tgtgacagct ggcaatttta taaatcaggt aactggaagg   6240
aggttaaaca cagaaaaaag aagacctcag tcaattctct actttttttt tttttccaa   6300
atcagataat agcccagcaa atagtgataa caaataaaac cttagctatt catgtcttga   6360
tttcaataat taattcttaa tcattaagag accataataa atactccttt tcaagagaaa   6420
agcaaaacca ttagaattgt tactcagctc cttcaaactc aggtttgtag catacatgag   6480
tccatccatc agtcaaagaa tggttccatc tggagtctta atgtagaaag aaaaatggag   6540
acttgtaata atgagctagt tacaaagtgc ttgttcatta aaatagcact gaaaattgaa   6600
acatgaatta actgataata ttccaatcat ttgccattta tgacaaaaat ggttggcact   6660
aacaaagaac gagcacttcc tttcagagtt tctgagataa tgtacgtgga acagtctggg   6720
tggaatgggg ctgaaaccat gtgcaagtct gtgtcttgtc agtccaagaa gtgacaccga   6780
gatgttaatt ttagggaccc gtgccttgtt tcctagccca caagaatgca aacatcaaac   6840
agatactcgc tagcctcatt taaattgatt aaaggaggag tgcatctttg gccgacagtg   6900
gtgtaactgt atgtgtgtgt gtgtgtgtgt gtgtgtgtgt gtgtgtgggt gtatgtgtgt   6960
tttgtgcata actatttaag gaaactggaa ttttaaagtt acttttatac aaaccaagaa   7020
tatatgctac agatataaga cagacatggt ttggtcctat atttctagtc atgatgaatg   7080
tattttgtat accatcttca tataataaac ttccaaaaac aca                     7123
```

<210> SEQ ID NO 6
<211> LENGTH: 6055
<212> TYPE: DNA
<213> ORGANISM: Homo sapiens

<400> SEQUENCE: 6

```
actgagtccc gggaccccgg gagagcggtc aatgtgtggt cgctgcgttt cctctgcctg     60
cgccgggcat cacttgcgcg ccgcagaaag tccgtctggc agcctggata tcctctccta    120
ccggcacccg cagacgcccc tgcagccgcg gtcggcgccc gggctcccta gccctgtgcg    180
ctcaactgtc ctgcgctgcg gggtgccgcg agttccacct ccgcgcctcc ttctctagac    240
aggcgctggg agaaagaacc ggctcccgag ttctgggcat ttcgcccggc tcgaggtgca    300
```

-continued

```
ggatgcagag caaggtgctg ctggccgtcg ccctgtggct ctgcgtggag acccgggccg    360
cctctgtggg tttgcctagt gtttctcttg atctgcccag gctcagcata caaaaagaca    420
tacttacaat taaggctaat acaactcttc aaattacttg caggggacag agggacttgg    480
actggctttg gcccaataat cagagtggca gtgagcaaag ggtggaggtg actgagtgca    540
gcgatggcct cttctgtaag acactcacaa ttccaaaagt gatcggaaat gacactggag    600
cctacaagtg cttctaccgg gaaactgact tggcctcggt catttatgtc tatgttcaag    660
attacagatc tccatttatt gcttctgtta gtgaccaaca tggagtcgtg tacattactg    720
agaacaaaaa caaaactgtg gtgattccat gtctcgggtc catttcaaat ctcaacgtgt    780
cactttgtgc aagataccca gaaaagagat ttgttcctga tggtaacaga atttcctggg    840
acagcaagaa gggctttact attcccagct acatgatcag ctatgctggc atggtcttct    900
gtgaagcaaa aattaatgat gaaagttacc agtctattat gtacatagtt gtcgttgtag    960
ggtataggat ttatgatgtg gttctgagtc cgtctcatgg aattgaacta tctgttggag   1020
aaaagcttgt cttaaattgt acagcaagaa ctgaactaaa tgtggggatt gacttcaact   1080
gggaataccc ttcttcgaag catcagcata agaaacttgt aaaccgagac ctaaaaaccc   1140
agtctgggag tgagatgaag aaatttttga gcaccttaac tatagatggt gtaacccgga   1200
gtgaccaagg attgtacacc tgtgcagcat ccagtgggct gatgaccaag aagaacagca   1260
catttgtcag ggtccatgaa aaaccttttg ttgcttttgg aagtggcatg gaatctctgg   1320
tggaagccac ggtgggggag cgtgtcagaa tccctgcgaa gtaccttggt tacccacccc   1380
cagaaataaa atggtataaa aatggaatac cccttgagtc caatcacaca attaaagcgg   1440
ggcatgtact gacgattatg gaagtgagtg aaagagacac aggaaattac actgtcatcc   1500
ttaccaatcc catttcaaag gagaagcaga gccatgtggt ctctctggtt gtgtatgtcc   1560
caccccagat tggtgagaaa tctctaatct ctcctgtgga ttcctaccag tacggcacca   1620
ctcaaacgct gacatgtacg gtctatgcca ttcctccccc gcatcacatc cactggtatt   1680
ggcagttgga ggaagagtgc gccaacgagc ccagccaagc tgtctcagtg acaaacccat   1740
acccttgtga agaatggaga agtgtggagg acttccaggg aggaaataaa attgaagtta   1800
ataaaaatca atttgctcta attgaaggaa aaaacaaaac tgtaagtacc cttgttatcc   1860
aagcggcaaa tgtgtcagct ttgtacaaat gtgaagcggt caacaaagtc gggagaggag   1920
agagggtgat ctccttccac gtgaccaggg gtcctgaaat tactttgcaa cctgacatgc   1980
agcccactga gcaggagagc gtgtctttgt ggtgcactgc agacagatct acgtttgaga   2040
acctcacatg gtacaagctt ggcccacagc ctctgccaat ccatgtggga gagttgccca   2100
cacctgtttg caagaacttg gatactcttt ggaaattgaa tgccaccatg ttctctaata   2160
gcacaaatga cattttgatc atggagctta agaatgcatc cttgcaggac caaggagact   2220
atgtctgcct tgctcaagac aggaagacca agaaaagaca ttgcgtggtc aggcagctca   2280
cagtcctaga gcgtgtggca cccacgatca caggaaacct ggagaatcag acgacaagta   2340
ttggggaaag catcgaagtc tcatgcacgg catctgggaa tccccctcca cagatcatgt   2400
ggtttaaaga taatgagacc cttgtagaag actcaggcat tgtattgaag gatgggaacc   2460
ggaacctcac tatccgcaga gtgaggaagg aggacgaagg cctctacacc tgccaggcat   2520
gcagtgttct tggctgtgca aaagtggagg catttttcat aatagaaggt gcccaggaaa   2580
agacgaactt ggaaatcatt attctagtag gcacggcggt gattgccatg ttcttctggc   2640
tacttcttgt catcatccta cggaccgtta agcgggccaa tggaggggaa ctgaagacag   2700
```

```
gctacttgtc catcgtcatg gatccagatg aactcccatt ggatgaacat tgtgaacgac   2760
tgccttatga tgccagcaaa tgggaattcc ccagagaccg gctgaagcta ggtaagcctc   2820
ttggccgtgg tgcctttggc caagtgattg aagcagatgc ctttggaatt gacaagacag   2880
caacttgcag gacagtagca gtcaaaatgt tgaaagaagg agcaacacac agtgagcatc   2940
gagctctcat gtctgaactc aagatcctca ttcatattgg tcaccatctc aatgtggtca   3000
accttctagg tgcctgtacc aagccaggag ggccactcat ggtgattgtg gaattctgca   3060
aatttggaaa cctgtccact tacctgagga gcaagagaaa tgaatttgtc ccctacaaga   3120
ccaaaggggc acgattccgt caagggaaag actacgttgg agcaatccct gtggatctga   3180
aacggcgctt ggacagcatc accagtagcc agagctcagc cagctctgga tttgtggagg   3240
agaagtccct cagtgatgta gaagaagagg aagctcctga agatctgtat aaggacttcc   3300
tgaccttgga gcatctcatc tgttacagct tccaagtggc taagggcatg gagttcttgg   3360
catcgcgaaa gtgtatccac agggacctgg cggcacgaaa tatcctctta tcggagaaga   3420
acgtggttaa aatctgtgac tttggcttgg cccgggatat ttataaagat ccagattatg   3480
tcagaaaagg agatgctcgc ctccctttga aatggatggc cccagaaaca atttttgaca   3540
gagtgtacac aatccagagt gacgtctggt cttttggtgt tttgctgtgg gaaatatttt   3600
ccttaggtgc ttctccatat cctggggtaa agattgatga agaattttgt aggcgattga   3660
aagaaggaac tagaatgagg gcccctgatt atactacacc agaaatgtac cagaccatgc   3720
tggactgctg gcacggggag cccagtcaga gacccacgtt ttcagagttg gtggaacatt   3780
tgggaaatct cttgcaagct aatgctcagc aggatggcaa agactacatt gttcttccga   3840
tatcagagac tttgagcatg gaagaggatt ctggactctc tctgcctacc tcacctgttt   3900
cctgtatgga ggaggaggaa gtatgtgacc ccaaattcca ttatgacaac acagcaggaa   3960
tcagtcagta tctgcagaac agtaagcgaa agagccggcc tgtgagtgta aaaacatttg   4020
aagatatccc gttagaagaa ccagaagtaa aagtaatccc agatgacaac cagacggaca   4080
gtggtatggt tcttgcctca gaagagctga aaactttgga agacagaacc aaattatctc   4140
catcttttgg tggaatggtg cccagcaaaa gcagggagtc tgtggcatct gaaggctcaa   4200
accagacaag cggctaccag tccggatatc actccgatga cacagacacc accgtgtact   4260
ccagtgagga agcagaactt ttaaagctga tagagattgg agtgcaaacc ggtagcacag   4320
cccagattct ccagcctgac tcggggacca cactgagctc tcctcctgtt taaaaggaag   4380
catccacacc cccaactcct ggacatcaca tgagaggtgc tgctcagatt ttcaagtgtt   4440
gttctttcca ccagcaggaa gtagccgcat ttgattttca tttcgacaac agaaaaagga   4500
cctcggactg cagggagcca gtcttctagg catatcctgg aagaggcttg tgacccaaga   4560
atgtgtctgt gtcttctccc agtgttgacc tgatcctctt tttcattcat ttaaaaagca   4620
tttatcatgc cccctgctgc gggtctcacc atgggtttag aacaaagacg ttcaagaaat   4680
ggccccatcc tcaaagaagt agcagtacct ggggagctga cacttctgta aaactagaag   4740
ataaaccagg caatgtaagt gttcgaggtg ttgaagatgg gaaggatttg cagggctgag   4800
tctatccaag aggctttgtt taggacgtgg gtcccaagcc aagccttaag tgtggaattc   4860
ggattgatag aaaggaagac taacgttacc ttgctttgga gagtactgga gcctgcaaat   4920
gcattgtgtt tgctctggtg gaggtgggca tggggtctgt tctgaaatgt aaagggttca   4980
gacggggttt ctggttttag aaggttgcgt gttcttcgag ttgggctaaa gtagagttcg   5040
```

-continued

```
ttgtgctgtt tctgactcct aatgagagtt ccttccagac cgttacgtgt ctcctggcca   5100

agccccagga aggaaatgat gcagctctgg ctccttgtct cccaggctga tcctttattc   5160

agaataccac aaagaaagga cattcagctc aaggctccct gccgtgttga agagttctga   5220

ctgcacaaac cagcttctgg tttcttctgg aatgaatacc ctcatatctg tcctgatgtg   5280

atatgtctga gactgaatgc gggaggttca atgtgaagct gtgtgtggtg tcaaagtttc   5340

aggaaggatt ttaccctttt gttcttcccc ctgtccccaa cccactctca ccccgcaacc   5400

catcagtatt ttagttattt ggcctctact ccagtaaacc tgattgggtt tgttcactct   5460

ctgaatgatt attagccaga cttcaaaatt attttatagc ccaaattata acatctattg   5520

tattatttag acttttaaca tatagagcta tttctactga tttttgccct tgttctgtcc   5580

ttttttttcaa aaaagaaaat gtgtttttttg tttggtacca tagtgtgaaa tgctgggaac   5640

aatgactata agacatgcta tggcacatat atttatagtc tgtttatgta gaaacaaatg   5700

taatatatta aagccttata tataatgaac tttgtactat tcacattttg tatcagtatt   5760

atgtagcata acaaaggtca taatgctttc agcaattgat gtcattttat taaagaacat   5820

tgaaaaactt gaaggaatcc ctttgcaagg ttgcattact gtacccatca tttctaaaat   5880

ggaagagggg gtggctgggc acagtggccg acacctaaaa acccagcact ttggggggcc   5940

aaggtgggag gatcgcttga gcccaggagt tcaagaccag tctggccaac atggtcagat   6000

tccatctcaa agaaaaaagg taaaaataaa ataaaatgga gaagaaggaa tcaga        6055
```

<210> SEQ ID NO 7
<211> LENGTH: 223
<212> TYPE: PRT
<213> ORGANISM: Homo sapiens

<400> SEQUENCE: 7

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Pro Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
```

```
        195                 200                 205

His Asn His Tyr Thr Gln Lys Ser Leu Ser Leu Ser Pro Gly Lys
    210                 215                 220


<210> SEQ ID NO 8
<211> LENGTH: 669
<212> TYPE: DNA
<213> ORGANISM: Homo sapiens

<400> SEQUENCE: 8

acatgcccac cgtgcccagc acctgaactc ctggggggac cgtcagtctt cctcttcccc      60

ccaaaaccca aggacaccct catgatctcc cggacccctg aggtcacatg cgtggtggtg     120

gacgtgagcc acgaagaccc tgaggtcaag ttcaactggt acgtggacgg cgtggaggtg     180

cataatgcca agacaaagcc gcgggaggag cagtacaaca gcacgtaccg tgtggtcagc     240

gtcctcaccg tcctgcacca ggactggctg aatggcaagg agtacaagtg caaggtctcc     300

aacaaagccc tcccagcccc catcgagaaa accatctcca aagccaaagg gcagccccga     360

gaaccacagg tgtacaccct gcccccatcc cgggatgagc tgaccaagaa ccaggtcagc     420

ctgacctgcc tggtcaaagg cttctatccc agcgacatcg ccgtggagtg ggagagcaat     480

gggcagccgg agaacaacta caagaccacg cctcccgtgc tggactccga cggctccttc     540

ttcctctaca gcaagctcac cgtggacaag agcaggtggc agcaggggaa cgtcttctca     600

tgctccgtga tgcatgaggc tctgcacaac cactacacgc agaagagcct ctccctgtct     660

ccgggtaaa                                                             669


<210> SEQ ID NO 9
<211> LENGTH: 666
<212> TYPE: PRT
<213> ORGANISM: Artificial
<220> FEATURE:
<223> OTHER INFORMATION: fused protein

<400> SEQUENCE: 9

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Gln Ile Ser Thr Pro Arg Pro Val Lys Leu Leu
            100                 105                 110

Arg Gly His Thr Leu Val Leu Asn Cys Thr Ala Thr Thr Pro Leu Asn
        115                 120                 125

Thr Arg Val Gln Met Thr Trp Ser Tyr Pro Asp Glu Lys Asn Arg Thr
    130                 135                 140

Arg Ile Thr Gly Glu Glu Val Glu Val Gln Asp Ser Val Pro Ala Asp
145                 150                 155                 160

Ser Gly Leu Tyr Ala Cys Val Thr Ser Ser Pro Ser Gly Ser Asp Thr
                165                 170                 175
```

-continued

```
Thr Tyr Phe Ser Val Asn Val Ser Asp Ala Leu Pro Ser Ser Glu Asp
            180                 185                 190

Asp Asp Asp Asp Asp Asp Ser Ser Ser Glu Glu Lys Glu Thr Asp Asn
        195                 200                 205

Thr Lys Pro Asn Pro Val Ala Pro Tyr Trp Thr Ser Pro Glu Lys Met
    210                 215                 220

Glu Lys Lys Leu His Ala Val Pro Ala Ala Lys Thr Val Lys Phe Lys
225                 230                 235                 240

Cys Pro Ser Ser Gly Thr Pro Asn Pro Thr Leu Arg Trp Leu Lys Asn
                245                 250                 255

Gly Lys Glu Phe Lys Pro Asp His Arg Ile Gly Gly Tyr Lys Val Arg
            260                 265                 270

Tyr Ala Thr Trp Ser Ile Ile Met Asp Ser Val Val Pro Ser Asp Lys
        275                 280                 285

Gly Asn Tyr Thr Cys Ile Val Glu Asn Glu Tyr Gly Ser Ile Asn His
    290                 295                 300

Thr Tyr Gln Leu Asp Val Val Glu Arg Ser Pro His Arg Pro Ile Leu
305                 310                 315                 320

Gln Ala Gly Leu Pro Ala Asn Lys Thr Val Ala Leu Gly Ser Asn Val
                325                 330                 335

Glu Phe Met Cys Lys Val Tyr Ser Asp Pro Gln Pro His Ile Gln Trp
            340                 345                 350

Leu Lys His Ile Glu Val Asn Gly Ser Lys Ile Gly Pro Asp Asn Leu
        355                 360                 365

Pro Tyr Val Gln Ile Leu Lys Thr Ala Gly Val Asn Thr Thr Asp Lys
    370                 375                 380

Glu Met Glu Val Leu His Leu Arg Asn Val Ser Phe Glu Asp Ala Gly
385                 390                 395                 400

Glu Tyr Thr Cys Leu Ala Gly Asn Ser Ile Gly Leu Ser His His Ser
                405                 410                 415

Ala Trp Leu Thr Val Leu Glu Ala Leu Glu Glu Arg Pro Ala Val Met
            420                 425                 430

Thr Ser Pro Leu Tyr Leu Glu Asp Lys Thr His Thr Cys Pro Pro Cys
        435                 440                 445

Pro Ala Pro Glu Leu Leu Gly Gly Pro Ser Val Phe Leu Phe Pro Pro
    450                 455                 460

Lys Pro Lys Asp Thr Leu Met Ile Ser Arg Thr Pro Glu Val Thr Cys
465                 470                 475                 480

Val Val Val Asp Val Ser His Glu Asp Pro Glu Val Lys Phe Asn Trp
                485                 490                 495

Tyr Val Asp Gly Val Glu Val His Asn Ala Lys Thr Lys Pro Arg Glu
            500                 505                 510

Glu Gln Tyr Asn Ser Thr Tyr Arg Val Val Ser Val Leu Thr Val Leu
        515                 520                 525

His Gln Asp Trp Leu Asn Gly Lys Glu Tyr Lys Cys Lys Val Ser Asn
    530                 535                 540

Lys Ala Leu Pro Ala Pro Ile Glu Lys Thr Ile Ser Lys Ala Lys Gly
545                 550                 555                 560

Gln Pro Arg Glu Pro Gln Val Tyr Thr Leu Pro Pro Ser Arg Asp Glu
                565                 570                 575

Leu Thr Lys Asn Gln Val Ser Leu Thr Cys Leu Val Lys Gly Phe Tyr
            580                 585                 590
```

```
Pro Ser Asp Ile Ala Val Glu Trp Glu Ser Asn Gly Gln Pro Glu Asn
        595                 600                 605

Asn Tyr Lys Thr Thr Pro Pro Val Leu Asp Ser Asp Gly Ser Phe Phe
    610                 615                 620

Leu Tyr Ser Lys Leu Thr Val Asp Lys Ser Arg Trp Gln Gln Gly Asn
625                 630                 635                 640

Val Phe Ser Cys Ser Val Met His Glu Ala Leu His Asn His Tyr Thr
                645                 650                 655

Gln Lys Ser Leu Ser Leu Ser Pro Gly Lys
            660                 665


<210> SEQ ID NO 10
<211> LENGTH: 587
<212> TYPE: PRT
<213> ORGANISM: Artificial
<220> FEATURE:
<223> OTHER INFORMATION: fused protein

<400> SEQUENCE: 10

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Gln Ile Ser Thr Pro Arg Pro Val Lys Leu Leu
            100                 105                 110

Arg Gly His Thr Leu Val Leu Asn Cys Thr Ala Thr Thr Pro Leu Asn
        115                 120                 125

Thr Arg Val Gln Met Thr Trp Ser Tyr Pro Asp Glu Lys Pro Glu Lys
    130                 135                 140

Met Glu Lys Lys Leu His Ala Val Pro Ala Ala Lys Thr Val Lys Phe
145                 150                 155                 160

Lys Cys Pro Ser Ser Gly Thr Pro Asn Pro Thr Leu Arg Trp Leu Lys
                165                 170                 175

Asn Gly Lys Glu Phe Lys Pro Asp His Arg Ile Gly Gly Tyr Lys Val
            180                 185                 190

Arg Tyr Ala Thr Trp Ser Ile Ile Met Asp Ser Val Val Pro Ser Asp
        195                 200                 205

Lys Gly Asn Tyr Thr Cys Ile Val Glu Asn Glu Tyr Gly Ser Ile Asn
    210                 215                 220

His Thr Tyr Gln Leu Asp Val Val Glu Arg Ser Pro His Arg Pro Ile
225                 230                 235                 240

Leu Gln Ala Gly Leu Pro Ala Asn Lys Thr Val Ala Leu Gly Ser Asn
                245                 250                 255

Val Glu Phe Met Cys Lys Val Tyr Ser Asp Pro Gln Pro His Ile Gln
            260                 265                 270

Trp Leu Lys His Ile Glu Val Asn Gly Ser Lys Ile Gly Pro Asp Asn
        275                 280                 285
```

```
Leu Pro Tyr Val Gln Ile Leu Lys Thr Ala Gly Val Asn Thr Thr Asp
    290                 295                 300

Lys Glu Met Glu Val Leu His Leu Arg Asn Val Ser Phe Glu Asp Ala
305                 310                 315                 320

Gly Glu Tyr Thr Cys Leu Ala Gly Asn Ser Ile Gly Leu Ser His His
                325                 330                 335

Ser Ala Trp Leu Thr Val Leu Glu Ala Leu Glu Glu Arg Pro Ala Val
            340                 345                 350

Met Thr Ser Pro Leu Tyr Leu Glu Asp Lys Thr His Thr Cys Pro Pro
        355                 360                 365

Cys Pro Ala Pro Glu Leu Leu Gly Gly Pro Ser Val Phe Leu Phe Pro
    370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415

Trp Tyr Val Asp Gly Val Glu Val His Asn Ala Lys Thr Lys Pro Arg
            420                 425                 430

Glu Glu Gln Tyr Asn Ser Thr Tyr Arg Val Val Ser Val Leu Thr Val
        435                 440                 445

Leu His Gln Asp Trp Leu Asn Gly Lys Glu Tyr Lys Cys Lys Val Ser
    450                 455                 460

Asn Lys Ala Leu Pro Ala Pro Ile Glu Lys Thr Ile Ser Lys Ala Lys
465                 470                 475                 480

Gly Gln Pro Arg Glu Pro Gln Val Tyr Thr Leu Pro Pro Ser Arg Asp
                485                 490                 495

Glu Leu Thr Lys Asn Gln Val Ser Leu Thr Cys Leu Val Lys Gly Phe
            500                 505                 510

Tyr Pro Ser Asp Ile Ala Val Glu Trp Glu Ser Asn Gly Gln Pro Glu
        515                 520                 525

Asn Asn Tyr Lys Thr Thr Pro Pro Val Leu Asp Ser Asp Gly Ser Phe
    530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                565                 570                 575

Thr Gln Lys Ser Leu Ser Leu Ser Pro Gly Lys
            580                 585
```

<210> SEQ ID NO 11
<211> LENGTH: 602
<212> TYPE: PRT
<213> ORGANISM: Artificial
<220> FEATURE:
<223> OTHER INFORMATION: fused protein

<400> SEQUENCE: 11

```
Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60
```

-continued

```
Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Gln Ile Ser Thr Pro Arg Pro Val Lys Leu Leu
            100                 105                 110

Arg Gly His Thr Leu Val Leu Asn Cys Thr Ala Thr Thr Pro Leu Asn
        115                 120                 125

Thr Arg Val Gln Met Thr Trp Ser Tyr Pro Asp Glu Lys Gly Gly Gly
    130                 135                 140

Gly Ser Gly Gly Gly Gly Ser Gly Gly Gly Gly Ser Pro Glu Lys Met
145                 150                 155                 160

Glu Lys Lys Leu His Ala Val Pro Ala Ala Lys Thr Val Lys Phe Lys
                165                 170                 175

Cys Pro Ser Ser Gly Thr Pro Asn Pro Thr Leu Arg Trp Leu Lys Asn
            180                 185                 190

Gly Lys Glu Phe Lys Pro Asp His Arg Ile Gly Gly Tyr Lys Val Arg
        195                 200                 205

Tyr Ala Thr Trp Ser Ile Ile Met Asp Ser Val Val Pro Ser Asp Lys
    210                 215                 220

Gly Asn Tyr Thr Cys Ile Val Glu Asn Glu Tyr Gly Ser Ile Asn His
225                 230                 235                 240

Thr Tyr Gln Leu Asp Val Val Glu Arg Ser Pro His Arg Pro Ile Leu
                245                 250                 255

Gln Ala Gly Leu Pro Ala Asn Lys Thr Val Ala Leu Gly Ser Asn Val
            260                 265                 270

Glu Phe Met Cys Lys Val Tyr Ser Asp Pro Gln Pro His Ile Gln Trp
        275                 280                 285

Leu Lys His Ile Glu Val Asn Gly Ser Lys Ile Gly Pro Asp Asn Leu
    290                 295                 300

Pro Tyr Val Gln Ile Leu Lys Thr Ala Gly Val Asn Thr Thr Asp Lys
305                 310                 315                 320

Glu Met Glu Val Leu His Leu Arg Asn Val Ser Phe Glu Asp Ala Gly
                325                 330                 335

Glu Tyr Thr Cys Leu Ala Gly Asn Ser Ile Gly Leu Ser His His Ser
            340                 345                 350

Ala Trp Leu Thr Val Leu Glu Ala Leu Glu Glu Arg Pro Ala Val Met
        355                 360                 365

Thr Ser Pro Leu Tyr Leu Glu Asp Lys Thr His Thr Cys Pro Pro Cys
    370                 375                 380

Pro Ala Pro Glu Leu Leu Gly Gly Pro Ser Val Phe Leu Phe Pro Pro
385                 390                 395                 400

Lys Pro Lys Asp Thr Leu Met Ile Ser Arg Thr Pro Glu Val Thr Cys
                405                 410                 415

Val Val Val Asp Val Ser His Glu Asp Pro Glu Val Lys Phe Asn Trp
            420                 425                 430

Tyr Val Asp Gly Val Glu Val His Asn Ala Lys Thr Lys Pro Arg Glu
        435                 440                 445

Glu Gln Tyr Asn Ser Thr Tyr Arg Val Val Ser Val Leu Thr Val Leu
    450                 455                 460

His Gln Asp Trp Leu Asn Gly Lys Glu Tyr Lys Cys Lys Val Ser Asn
465                 470                 475                 480

Lys Ala Leu Pro Ala Pro Ile Glu Lys Thr Ile Ser Lys Ala Lys Gly
```

```
                485                 490                 495

Gln Pro Arg Glu Pro Gln Val Tyr Thr Leu Pro Pro Ser Arg Asp Glu
            500                 505                 510

Leu Thr Lys Asn Gln Val Ser Leu Thr Cys Leu Val Lys Gly Phe Tyr
        515                 520                 525

Pro Ser Asp Ile Ala Val Glu Trp Glu Ser Asn Gly Gln Pro Glu Asn
    530                 535                 540

Asn Tyr Lys Thr Thr Pro Pro Val Leu Asp Ser Asp Gly Ser Phe Phe
545                 550                 555                 560

Leu Tyr Ser Lys Leu Thr Val Asp Lys Ser Arg Trp Gln Gln Gly Asn
                565                 570                 575

Val Phe Ser Cys Ser Val Met His Glu Ala Leu His Asn His Tyr Thr
            580                 585                 590

Gln Lys Ser Leu Ser Leu Ser Pro Gly Lys
        595                 600


<210> SEQ ID NO 12
<211> LENGTH: 754
<212> TYPE: PRT
<213> ORGANISM: artificial
<220> FEATURE:
<223> OTHER INFORMATION: fused protein

<400> SEQUENCE: 12

Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Val Leu
        195                 200                 205

Ser Pro Ser His Gly Ile Glu Leu Ser Val Gly Glu Lys Leu Val Leu
    210                 215                 220

Asn Cys Thr Ala Arg Thr Glu Leu Asn Val Gly Ile Asp Phe Asn Trp
225                 230                 235                 240

Glu Tyr Pro Ser Ser Lys His Gln His Lys Lys Leu Val Asn Arg Asp
```

```
                245                 250                 255

Leu Lys Thr Gln Ser Gly Ser Glu Met Lys Lys Phe Leu Ser Thr Leu
            260                 265                 270

Thr Ile Asp Gly Val Thr Arg Ser Asp Gln Gly Leu Tyr Thr Cys Ala
        275                 280                 285

Ala Ser Ser Gly Leu Met Thr Lys Lys Asn Ser Thr Phe Val Arg Val
    290                 295                 300

His Glu Lys Pro Pro Glu Lys Met Glu Lys Lys Leu His Ala Val Pro
305                 310                 315                 320

Ala Ala Lys Thr Val Lys Phe Lys Cys Pro Ser Ser Gly Thr Pro Asn
                325                 330                 335

Pro Thr Leu Arg Trp Leu Lys Asn Gly Lys Glu Phe Lys Pro Asp His
            340                 345                 350

Arg Ile Gly Gly Tyr Lys Val Arg Tyr Ala Thr Trp Ser Ile Ile Met
        355                 360                 365

Asp Ser Val Val Pro Ser Asp Lys Gly Asn Tyr Thr Cys Ile Val Glu
    370                 375                 380

Asn Glu Tyr Gly Ser Ile Asn His Thr Tyr Gln Leu Asp Val Val Glu
385                 390                 395                 400

Arg Ser Pro His Arg Pro Ile Leu Gln Ala Gly Leu Pro Ala Asn Lys
                405                 410                 415

Thr Val Ala Leu Gly Ser Asn Val Glu Phe Met Cys Lys Val Tyr Ser
            420                 425                 430

Asp Pro Gln Pro His Ile Gln Trp Leu Lys His Ile Glu Val Asn Gly
        435                 440                 445

Ser Lys Ile Gly Pro Asp Asn Leu Pro Tyr Val Gln Ile Leu Lys Thr
    450                 455                 460

Ala Gly Val Asn Thr Thr Asp Lys Glu Met Glu Val Leu His Leu Arg
465                 470                 475                 480

Asn Val Ser Phe Glu Asp Ala Gly Glu Tyr Thr Cys Leu Ala Gly Asn
                485                 490                 495

Ser Ile Gly Leu Ser His His Ser Ala Trp Leu Thr Val Leu Glu Ala
            500                 505                 510

Leu Glu Glu Arg Pro Ala Val Met Thr Ser Pro Leu Tyr Leu Glu Asp
        515                 520                 525

Lys Thr His Thr Cys Pro Pro Cys Pro Ala Pro Glu Leu Leu Gly Gly
    530                 535                 540

Pro Ser Val Phe Leu Phe Pro Pro Lys Pro Lys Asp Thr Leu Met Ile
545                 550                 555                 560

Ser Arg Thr Pro Glu Val Thr Cys Val Val Val Asp Val Ser His Glu
                565                 570                 575

Asp Pro Glu Val Lys Phe Asn Trp Tyr Val Asp Gly Val Glu Val His
            580                 585                 590

Asn Ala Lys Thr Lys Pro Arg Glu Glu Gln Tyr Asn Ser Thr Tyr Arg
        595                 600                 605

Val Val Ser Val Leu Thr Val Leu His Gln Asp Trp Leu Asn Gly Lys
    610                 615                 620

Glu Tyr Lys Cys Lys Val Ser Asn Lys Ala Leu Pro Ala Pro Ile Glu
625                 630                 635                 640

Lys Thr Ile Ser Lys Ala Lys Gly Gln Pro Arg Glu Pro Gln Val Tyr
                645                 650                 655

Thr Leu Pro Pro Ser Arg Asp Glu Leu Thr Lys Asn Gln Val Ser Leu
            660                 665                 670
```

-continued

```
Thr Cys Leu Val Lys Gly Phe Tyr Pro Ser Asp Ile Ala Val Glu Trp
        675                 680                 685

Glu Ser Asn Gly Gln Pro Glu Asn Asn Tyr Lys Thr Thr Pro Pro Val
    690                 695                 700

Leu Asp Ser Asp Gly Ser Phe Phe Leu Tyr Ser Lys Leu Thr Val Asp
705                 710                 715                 720

Lys Ser Arg Trp Gln Gln Gly Asn Val Phe Ser Cys Ser Val Met His
                725                 730                 735

Glu Ala Leu His Asn His Tyr Thr Gln Lys Ser Leu Ser Leu Ser Pro
            740                 745                 750

Gly Lys


<210> SEQ ID NO 13
<211> LENGTH: 834
<212> TYPE: PRT
<213> ORGANISM: artificial
<220> FEATURE:
<223> OTHER INFORMATION: fused protein

<400> SEQUENCE: 13

Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Val Leu
        195                 200                 205

Ser Pro Ser His Gly Ile Glu Leu Ser Val Gly Glu Lys Leu Val Leu
    210                 215                 220

Asn Cys Thr Ala Arg Thr Glu Leu Asn Val Gly Ile Asp Phe Asn Trp
225                 230                 235                 240

Glu Tyr Pro Ser Ser Lys His Gln His Lys Lys Leu Val Asn Arg Asp
                245                 250                 255

Leu Lys Thr Gln Ser Gly Ser Glu Met Lys Lys Phe Leu Ser Thr Leu
            260                 265                 270
```

-continued

```
Thr Ile Asp Gly Val Thr Arg Ser Asp Gln Gly Leu Tyr Thr Cys Ala
        275                 280                 285

Ala Ser Ser Gly Leu Met Thr Lys Lys Asn Ser Thr Phe Val Arg Val
    290                 295                 300

His Glu Lys Pro Lys Asn Arg Thr Arg Ile Thr Gly Glu Glu Val Glu
305                 310                 315                 320

Val Gln Asp Ser Val Pro Ala Asp Ser Gly Leu Tyr Ala Cys Val Thr
                325                 330                 335

Ser Ser Pro Ser Gly Ser Asp Thr Thr Tyr Phe Ser Val Asn Val Ser
            340                 345                 350

Asp Ala Leu Pro Ser Ser Glu Asp Asp Asp Asp Asp Asp Asp Ser Ser
        355                 360                 365

Ser Glu Glu Lys Glu Thr Asp Asn Thr Lys Pro Asn Pro Val Ala Pro
    370                 375                 380

Tyr Trp Thr Ser Pro Glu Lys Met Glu Lys Lys Leu His Ala Val Pro
385                 390                 395                 400

Ala Ala Lys Thr Val Lys Phe Lys Cys Pro Ser Ser Gly Thr Pro Asn
                405                 410                 415

Pro Thr Leu Arg Trp Leu Lys Asn Gly Lys Glu Phe Lys Pro Asp His
            420                 425                 430

Arg Ile Gly Gly Tyr Lys Val Arg Tyr Ala Thr Trp Ser Ile Ile Met
        435                 440                 445

Asp Ser Val Val Pro Ser Asp Lys Gly Asn Tyr Thr Cys Ile Val Glu
    450                 455                 460

Asn Glu Tyr Gly Ser Ile Asn His Thr Tyr Gln Leu Asp Val Val Glu
465                 470                 475                 480

Arg Ser Pro His Arg Pro Ile Leu Gln Ala Gly Leu Pro Ala Asn Lys
                485                 490                 495

Thr Val Ala Leu Gly Ser Asn Val Glu Phe Met Cys Lys Val Tyr Ser
            500                 505                 510

Asp Pro Gln Pro His Ile Gln Trp Leu Lys His Ile Glu Val Asn Gly
        515                 520                 525

Ser Lys Ile Gly Pro Asp Asn Leu Pro Tyr Val Gln Ile Leu Lys Thr
    530                 535                 540

Ala Gly Val Asn Thr Thr Asp Lys Glu Met Glu Val Leu His Leu Arg
545                 550                 555                 560

Asn Val Ser Phe Glu Asp Ala Gly Glu Tyr Thr Cys Leu Ala Gly Asn
                565                 570                 575

Ser Ile Gly Leu Ser His His Ser Ala Trp Leu Thr Val Leu Glu Ala
            580                 585                 590

Leu Glu Glu Arg Pro Ala Val Met Thr Ser Pro Leu Tyr Leu Glu Asp
        595                 600                 605

Lys Thr His Thr Cys Pro Pro Cys Pro Ala Pro Glu Leu Leu Gly Gly
    610                 615                 620

Pro Ser Val Phe Leu Phe Pro Pro Lys Pro Lys Asp Thr Leu Met Ile
625                 630                 635                 640

Ser Arg Thr Pro Glu Val Thr Cys Val Val Val Asp Val Ser His Glu
                645                 650                 655

Asp Pro Glu Val Lys Phe Asn Trp Tyr Val Asp Gly Val Glu Val His
            660                 665                 670

Asn Ala Lys Thr Lys Pro Arg Glu Glu Gln Tyr Asn Ser Thr Tyr Arg
        675                 680                 685

Val Val Ser Val Leu Thr Val Leu His Gln Asp Trp Leu Asn Gly Lys
```

```
    690                 695                 700

Glu Tyr Lys Cys Lys Val Ser Asn Lys Ala Leu Pro Ala Pro Ile Glu
705                 710                 715                 720

Lys Thr Ile Ser Lys Ala Lys Gly Gln Pro Arg Glu Pro Gln Val Tyr
                725                 730                 735

Thr Leu Pro Pro Ser Arg Asp Glu Leu Thr Lys Asn Gln Val Ser Leu
            740                 745                 750

Thr Cys Leu Val Lys Gly Phe Tyr Pro Ser Asp Ile Ala Val Glu Trp
        755                 760                 765

Glu Ser Asn Gly Gln Pro Glu Asn Asn Tyr Lys Thr Thr Pro Pro Val
    770                 775                 780

Leu Asp Ser Asp Gly Ser Phe Phe Leu Tyr Ser Lys Leu Thr Val Asp
785                 790                 795                 800

Lys Ser Arg Trp Gln Gln Gly Asn Val Phe Ser Cys Ser Val Met His
                805                 810                 815

Glu Ala Leu His Asn His Tyr Thr Gln Lys Ser Leu Ser Leu Ser Pro
            820                 825                 830

Gly Lys


<210> SEQ ID NO 14
<211> LENGTH: 754
<212> TYPE: PRT
<213> ORGANISM: artificial
<220> FEATURE:
<223> OTHER INFORMATION: fused protein

<400> SEQUENCE: 14

Pro Glu Lys Met Glu Lys Lys Leu His Ala Val Pro Ala Ala Lys Thr
1               5                   10                  15

Val Lys Phe Lys Cys Pro Ser Ser Gly Thr Pro Asn Pro Thr Leu Arg
            20                  25                  30

Trp Leu Lys Asn Gly Lys Glu Phe Lys Pro Asp His Arg Ile Gly Gly
        35                  40                  45

Tyr Lys Val Arg Tyr Ala Thr Trp Ser Ile Ile Met Asp Ser Val Val
    50                  55                  60

Pro Ser Asp Lys Gly Asn Tyr Thr Cys Ile Val Glu Asn Glu Tyr Gly
65                  70                  75                  80

Ser Ile Asn His Thr Tyr Gln Leu Asp Val Val Glu Arg Ser Pro His
                85                  90                  95

Arg Pro Ile Leu Gln Ala Gly Leu Pro Ala Asn Lys Thr Val Ala Leu
            100                 105                 110

Gly Ser Asn Val Glu Phe Met Cys Lys Val Tyr Ser Asp Pro Gln Pro
        115                 120                 125

His Ile Gln Trp Leu Lys His Ile Glu Val Asn Gly Ser Lys Ile Gly
    130                 135                 140

Pro Asp Asn Leu Pro Tyr Val Gln Ile Leu Lys Thr Ala Gly Val Asn
145                 150                 155                 160

Thr Thr Asp Lys Glu Met Glu Val Leu His Leu Arg Asn Val Ser Phe
                165                 170                 175

Glu Asp Ala Gly Glu Tyr Thr Cys Leu Ala Gly Asn Ser Ile Gly Leu
            180                 185                 190

Ser His His Ser Ala Trp Leu Thr Val Leu Glu Ala Leu Glu Glu Arg
        195                 200                 205

Pro Ala Val Met Thr Ser Pro Leu Tyr Leu Glu Ser Lys Leu Lys Asp
    210                 215                 220
```

-continued

```
Pro Glu Leu Ser Leu Lys Gly Thr Gln His Ile Met Gln Ala Gly Gln
225                 230                 235                 240

Thr Leu His Leu Gln Cys Arg Gly Glu Ala Ala His Lys Trp Ser Leu
                245                 250                 255

Pro Glu Met Val Ser Lys Glu Ser Glu Arg Leu Ser Ile Thr Lys Ser
            260                 265                 270

Ala Cys Gly Arg Asn Gly Lys Gln Phe Cys Ser Thr Leu Thr Leu Asn
        275                 280                 285

Thr Ala Gln Ala Asn His Thr Gly Phe Tyr Ser Cys Lys Tyr Leu Ala
    290                 295                 300

Val Pro Thr Ser Lys Lys Lys Glu Thr Glu Ser Ala Ile Tyr Ile Phe
305                 310                 315                 320

Ile Ser Asp Thr Gly Arg Pro Phe Val Glu Met Tyr Ser Glu Ile Pro
                325                 330                 335

Glu Ile Ile His Met Thr Glu Gly Arg Glu Leu Val Ile Pro Cys Arg
            340                 345                 350

Val Thr Ser Pro Asn Ile Thr Val Thr Leu Lys Lys Phe Pro Leu Asp
        355                 360                 365

Thr Leu Ile Pro Asp Gly Lys Arg Ile Ile Trp Asp Ser Arg Lys Gly
    370                 375                 380

Phe Ile Ile Ser Asn Ala Thr Tyr Lys Glu Ile Gly Leu Leu Thr Cys
385                 390                 395                 400

Glu Ala Thr Val Asn Gly His Leu Tyr Lys Thr Asn Tyr Leu Thr His
                405                 410                 415

Arg Gln Thr Asn Thr Ile Ile Asp Val Val Leu Ser Pro Ser His Gly
            420                 425                 430

Ile Glu Leu Ser Val Gly Glu Lys Leu Val Leu Asn Cys Thr Ala Arg
        435                 440                 445

Thr Glu Leu Asn Val Gly Ile Asp Phe Asn Trp Glu Tyr Pro Ser Ser
    450                 455                 460

Lys His Gln His Lys Lys Leu Val Asn Arg Asp Leu Lys Thr Gln Ser
465                 470                 475                 480

Gly Ser Glu Met Lys Lys Phe Leu Ser Thr Leu Thr Ile Asp Gly Val
                485                 490                 495

Thr Arg Ser Asp Gln Gly Leu Tyr Thr Cys Ala Ala Ser Ser Gly Leu
            500                 505                 510

Met Thr Lys Lys Asn Ser Thr Phe Val Arg Val His Glu Lys Pro Asp
        515                 520                 525

Lys Thr His Thr Cys Pro Pro Cys Pro Ala Pro Glu Leu Leu Gly Gly
    530                 535                 540

Pro Ser Val Phe Leu Phe Pro Pro Lys Pro Lys Asp Thr Leu Met Ile
545                 550                 555                 560

Ser Arg Thr Pro Glu Val Thr Cys Val Val Val Asp Val Ser His Glu
                565                 570                 575

Asp Pro Glu Val Lys Phe Asn Trp Tyr Val Asp Gly Val Glu Val His
            580                 585                 590

Asn Ala Lys Thr Lys Pro Arg Glu Glu Gln Tyr Asn Ser Thr Tyr Arg
        595                 600                 605

Val Val Ser Val Leu Thr Val Leu His Gln Asp Trp Leu Asn Gly Lys
    610                 615                 620

Glu Tyr Lys Cys Lys Val Ser Asn Lys Ala Leu Pro Ala Pro Ile Glu
625                 630                 635                 640
```

```
Lys Thr Ile Ser Lys Ala Lys Gly Gln Pro Arg Glu Pro Gln Val Tyr
                645                 650                 655

Thr Leu Pro Pro Ser Arg Asp Glu Leu Thr Lys Asn Gln Val Ser Leu
            660                 665                 670

Thr Cys Leu Val Lys Gly Phe Tyr Pro Ser Asp Ile Ala Val Glu Trp
        675                 680                 685

Glu Ser Asn Gly Gln Pro Glu Asn Asn Tyr Lys Thr Thr Pro Pro Val
    690                 695                 700

Leu Asp Ser Asp Gly Ser Phe Phe Leu Tyr Ser Lys Leu Thr Val Asp
705                 710                 715                 720

Lys Ser Arg Trp Gln Gln Gly Asn Val Phe Ser Cys Ser Val Met His
                725                 730                 735

Glu Ala Leu His Asn His Tyr Thr Gln Lys Ser Leu Ser Leu Ser Pro
            740                 745                 750

Gly Lys


<210> SEQ ID NO 15
<211> LENGTH: 535
<212> TYPE: PRT
<213> ORGANISM: artificial
<220> FEATURE:
<223> OTHER INFORMATION: fused protein

<400> SEQUENCE: 15

Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Val Leu
        195                 200                 205

Ser Pro Ser His Gly Ile Glu Leu Ser Val Gly Glu Lys Leu Val Leu
    210                 215                 220

Asn Cys Thr Ala Arg Thr Glu Leu Asn Val Gly Ile Asp Phe Asn Trp
225                 230                 235                 240

Glu Tyr Pro Ser Ser Lys His Gln His Lys Lys Leu Val Asn Arg Asp
```

```
                245                 250                 255

Leu Lys Thr Gln Ser Gly Ser Glu Met Lys Lys Phe Leu Ser Thr Leu
            260                 265                 270

Thr Ile Asp Gly Val Thr Arg Ser Asp Gln Gly Leu Tyr Thr Cys Ala
        275                 280                 285

Ala Ser Ser Gly Leu Met Thr Lys Lys Asn Ser Thr Phe Val Arg Val
    290                 295                 300

His Glu Lys Pro Asp Lys Thr His Thr Cys Pro Pro Cys Pro Ala Pro
305                 310                 315                 320

Glu Leu Leu Gly Gly Pro Ser Val Phe Leu Phe Pro Pro Lys Pro Lys
                325                 330                 335

Asp Thr Leu Met Ile Ser Arg Thr Pro Glu Val Thr Cys Val Val Val
            340                 345                 350

Asp Val Ser His Glu Asp Pro Glu Val Lys Phe Asn Trp Tyr Val Asp
        355                 360                 365

Gly Val Glu Val His Asn Ala Lys Thr Lys Pro Arg Glu Glu Gln Tyr
    370                 375                 380

Asn Ser Thr Tyr Arg Val Val Ser Val Leu Thr Val Leu His Gln Asp
385                 390                 395                 400

Trp Leu Asn Gly Lys Glu Tyr Lys Cys Lys Val Ser Asn Lys Ala Leu
                405                 410                 415

Pro Ala Pro Ile Glu Lys Thr Ile Ser Lys Ala Lys Gly Gln Pro Arg
            420                 425                 430

Glu Pro Gln Val Tyr Thr Leu Pro Pro Ser Arg Asp Glu Leu Thr Lys
        435                 440                 445

Asn Gln Val Ser Leu Thr Cys Leu Val Lys Gly Phe Tyr Pro Ser Asp
    450                 455                 460

Ile Ala Val Glu Trp Glu Ser Asn Gly Gln Pro Glu Asn Asn Tyr Lys
465                 470                 475                 480

Thr Thr Pro Pro Val Leu Asp Ser Asp Gly Ser Phe Phe Leu Tyr Ser
                485                 490                 495

Lys Leu Thr Val Asp Lys Ser Arg Trp Gln Gln Gly Asn Val Phe Ser
            500                 505                 510

Cys Ser Val Met His Glu Ala Leu His Asn His Tyr Thr Gln Lys Ser
        515                 520                 525

Leu Ser Leu Ser Pro Gly Lys
    530                 535


<210> SEQ ID NO 16
<211> LENGTH: 834
<212> TYPE: PRT
<213> ORGANISM: artificial
<220> FEATURE:
<223> OTHER INFORMATION: fused protein

<400> SEQUENCE: 16

Lys Asn Arg Thr Arg Ile Thr Gly Glu Glu Val Glu Val Gln Asp Ser
1               5                   10                  15

Val Pro Ala Asp Ser Gly Leu Tyr Ala Cys Val Thr Ser Ser Pro Ser
            20                  25                  30

Gly Ser Asp Thr Thr Tyr Phe Ser Val Asn Val Ser Asp Ala Leu Pro
        35                  40                  45

Ser Ser Glu Asp Asp Asp Asp Asp Asp Asp Ser Ser Ser Glu Glu Lys
    50                  55                  60

Glu Thr Asp Asn Thr Lys Pro Asn Pro Val Ala Pro Tyr Trp Thr Ser
```

-continued

```
65                  70                  75                  80

Pro Glu Lys Met Glu Lys Lys Leu His Ala Val Pro Ala Ala Lys Thr
                85                  90                  95

Val Lys Phe Lys Cys Pro Ser Ser Gly Thr Pro Asn Pro Thr Leu Arg
            100                 105                 110

Trp Leu Lys Asn Gly Lys Glu Phe Lys Pro Asp His Arg Ile Gly Gly
        115                 120                 125

Tyr Lys Val Arg Tyr Ala Thr Trp Ser Ile Ile Met Asp Ser Val Val
    130                 135                 140

Pro Ser Asp Lys Gly Asn Tyr Thr Cys Ile Val Glu Asn Glu Tyr Gly
145                 150                 155                 160

Ser Ile Asn His Thr Tyr Gln Leu Asp Val Val Glu Arg Ser Pro His
                165                 170                 175

Arg Pro Ile Leu Gln Ala Gly Leu Pro Ala Asn Lys Thr Val Ala Leu
            180                 185                 190

Gly Ser Asn Val Glu Phe Met Cys Lys Val Tyr Ser Asp Pro Gln Pro
        195                 200                 205

His Ile Gln Trp Leu Lys His Ile Glu Val Asn Gly Ser Lys Ile Gly
    210                 215                 220

Pro Asp Asn Leu Pro Tyr Val Gln Ile Leu Lys Thr Ala Gly Val Asn
225                 230                 235                 240

Thr Thr Asp Lys Glu Met Glu Val Leu His Leu Arg Asn Val Ser Phe
                245                 250                 255

Glu Asp Ala Gly Glu Tyr Thr Cys Leu Ala Gly Asn Ser Ile Gly Leu
            260                 265                 270

Ser His His Ser Ala Trp Leu Thr Val Leu Glu Ala Leu Glu Glu Arg
        275                 280                 285

Pro Ala Val Met Thr Ser Pro Leu Tyr Leu Glu Ser Lys Leu Lys Asp
    290                 295                 300

Pro Glu Leu Ser Leu Lys Gly Thr Gln His Ile Met Gln Ala Gly Gln
305                 310                 315                 320

Thr Leu His Leu Gln Cys Arg Gly Glu Ala Ala His Lys Trp Ser Leu
                325                 330                 335

Pro Glu Met Val Ser Lys Glu Ser Glu Arg Leu Ser Ile Thr Lys Ser
            340                 345                 350

Ala Cys Gly Arg Asn Gly Lys Gln Phe Cys Ser Thr Leu Thr Leu Asn
        355                 360                 365

Thr Ala Gln Ala Asn His Thr Gly Phe Tyr Ser Cys Lys Tyr Leu Ala
    370                 375                 380

Val Pro Thr Ser Lys Lys Lys Glu Thr Glu Ser Ala Ile Tyr Ile Phe
385                 390                 395                 400

Ile Ser Asp Thr Gly Arg Pro Phe Val Glu Met Tyr Ser Glu Ile Pro
                405                 410                 415

Glu Ile Ile His Met Thr Glu Gly Arg Glu Leu Val Ile Pro Cys Arg
            420                 425                 430

Val Thr Ser Pro Asn Ile Thr Val Thr Leu Lys Lys Phe Pro Leu Asp
        435                 440                 445

Thr Leu Ile Pro Asp Gly Lys Arg Ile Ile Trp Asp Ser Arg Lys Gly
    450                 455                 460

Phe Ile Ile Ser Asn Ala Thr Tyr Lys Glu Ile Gly Leu Leu Thr Cys
465                 470                 475                 480

Glu Ala Thr Val Asn Gly His Leu Tyr Lys Thr Asn Tyr Leu Thr His
                485                 490                 495
```

```
Arg Gln Thr Asn Thr Ile Ile Asp Val Val Leu Ser Pro Ser His Gly
            500                 505                 510

Ile Glu Leu Ser Val Gly Glu Lys Leu Val Leu Asn Cys Thr Ala Arg
        515                 520                 525

Thr Glu Leu Asn Val Gly Ile Asp Phe Asn Trp Glu Tyr Pro Ser Ser
    530                 535                 540

Lys His Gln His Lys Lys Leu Val Asn Arg Asp Leu Lys Thr Gln Ser
545                 550                 555                 560

Gly Ser Glu Met Lys Lys Phe Leu Ser Thr Leu Thr Ile Asp Gly Val
                565                 570                 575

Thr Arg Ser Asp Gln Gly Leu Tyr Thr Cys Ala Ala Ser Ser Gly Leu
            580                 585                 590

Met Thr Lys Lys Asn Ser Thr Phe Val Arg Val His Glu Lys Pro Asp
        595                 600                 605

Lys Thr His Thr Cys Pro Pro Cys Pro Ala Pro Glu Leu Leu Gly Gly
    610                 615                 620

Pro Ser Val Phe Leu Phe Pro Pro Lys Pro Lys Asp Thr Leu Met Ile
625                 630                 635                 640

Ser Arg Thr Pro Glu Val Thr Cys Val Val Val Asp Val Ser His Glu
                645                 650                 655

Asp Pro Glu Val Lys Phe Asn Trp Tyr Val Asp Gly Val Glu Val His
            660                 665                 670

Asn Ala Lys Thr Lys Pro Arg Glu Glu Gln Tyr Asn Ser Thr Tyr Arg
        675                 680                 685

Val Val Ser Val Leu Thr Val Leu His Gln Asp Trp Leu Asn Gly Lys
    690                 695                 700

Glu Tyr Lys Cys Lys Val Ser Asn Lys Ala Leu Pro Ala Pro Ile Glu
705                 710                 715                 720

Lys Thr Ile Ser Lys Ala Lys Gly Gln Pro Arg Glu Pro Gln Val Tyr
                725                 730                 735

Thr Leu Pro Pro Ser Arg Asp Glu Leu Thr Lys Asn Gln Val Ser Leu
            740                 745                 750

Thr Cys Leu Val Lys Gly Phe Tyr Pro Ser Asp Ile Ala Val Glu Trp
        755                 760                 765

Glu Ser Asn Gly Gln Pro Glu Asn Asn Tyr Lys Thr Thr Pro Pro Val
    770                 775                 780

Leu Asp Ser Asp Gly Ser Phe Phe Leu Tyr Ser Lys Leu Thr Val Asp
785                 790                 795                 800

Lys Ser Arg Trp Gln Gln Gly Asn Val Phe Ser Cys Ser Val Met His
                805                 810                 815

Glu Ala Leu His Asn His Tyr Thr Gln Lys Ser Leu Ser Leu Ser Pro
            820                 825                 830

Gly Lys


<210> SEQ ID NO 17
<211> LENGTH: 430
<212> TYPE: PRT
<213> ORGANISM: artificial
<220> FEATURE:
<223> OTHER INFORMATION: fused protein

<400> SEQUENCE: 17

Gly Arg Pro Phe Val Glu Met Tyr Ser Glu Ile Pro Glu Ile Ile His
1               5                   10                  15
```

-continued

```
Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Pro Asp Lys Thr His Thr
        195                 200                 205

Cys Pro Pro Cys Pro Ala Pro Glu Leu Leu Gly Gly Pro Ser Val Phe
    210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser His Glu Asp Pro Glu Val
                245                 250                 255

Lys Phe Asn Trp Tyr Val Asp Gly Val Glu Val His Asn Ala Lys Thr
            260                 265                 270

Lys Pro Arg Glu Glu Gln Tyr Asn Ser Thr Tyr Arg Val Val Ser Val
        275                 280                 285

Leu Thr Val Leu His Gln Asp Trp Leu Asn Gly Lys Glu Tyr Lys Cys
    290                 295                 300

Lys Val Ser Asn Lys Ala Leu Pro Ala Pro Ile Glu Lys Thr Ile Ser
305                 310                 315                 320

Lys Ala Lys Gly Gln Pro Arg Glu Pro Gln Val Tyr Thr Leu Pro Pro
                325                 330                 335

Ser Arg Asp Glu Leu Thr Lys Asn Gln Val Ser Leu Thr Cys Leu Val
            340                 345                 350

Lys Gly Phe Tyr Pro Ser Asp Ile Ala Val Glu Trp Glu Ser Asn Gly
        355                 360                 365

Gln Pro Glu Asn Asn Tyr Lys Thr Thr Pro Pro Val Leu Asp Ser Asp
    370                 375                 380

Gly Ser Phe Phe Leu Tyr Ser Lys Leu Thr Val Asp Lys Ser Arg Trp
385                 390                 395                 400

Gln Gln Gly Asn Val Phe Ser Cys Ser Val Met His Glu Ala Leu His
                405                 410                 415

Asn His Tyr Thr Gln Lys Ser Leu Ser Leu Ser Pro Gly Lys
            420                 425                 430
```

<210> SEQ ID NO 18
<211> LENGTH: 888
<212> TYPE: PRT
<213> ORGANISM: artificial
<220> FEATURE:
<223> OTHER INFORMATION: fused protein

<400> SEQUENCE: 18

```
Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Val Leu
        195                 200                 205

Ser Pro Ser His Gly Ile Glu Leu Ser Val Gly Glu Lys Leu Val Leu
    210                 215                 220

Asn Cys Thr Ala Arg Thr Glu Leu Asn Val Gly Ile Asp Phe Asn Trp
225                 230                 235                 240

Glu Tyr Pro Ser Ser Lys His Gln His Lys Lys Leu Val Asn Arg Asp
                245                 250                 255

Leu Lys Thr Gln Ser Gly Ser Glu Met Lys Lys Phe Leu Ser Thr Leu
            260                 265                 270

Thr Ile Asp Gly Val Thr Arg Ser Asp Gln Gly Leu Tyr Thr Cys Ala
        275                 280                 285

Ala Ser Ser Gly Leu Met Thr Lys Lys Asn Ser Thr Phe Val Arg Val
    290                 295                 300

His Glu Lys Pro Arg Pro Ser Pro Thr Leu Pro Glu Gln Ala Gln Pro
305                 310                 315                 320

Trp Gly Ala Pro Val Glu Val Glu Ser Phe Leu Val His Pro Gly Asp
                325                 330                 335

Leu Leu Gln Leu Arg Cys Arg Leu Arg Asp Asp Val Gln Ser Ile Asn
            340                 345                 350

Trp Leu Arg Asp Gly Val Gln Leu Ala Glu Ser Asn Arg Thr Arg Ile
        355                 360                 365

Thr Gly Glu Glu Val Glu Val Gln Asp Ser Val Pro Ala Asp Ser Gly
```

```
    370                 375                 380

Leu Tyr Ala Cys Val Thr Ser Ser Pro Ser Gly Ser Asp Thr Thr Tyr
385                 390                 395                 400

Phe Ser Val Asn Val Ser Asp Ala Leu Pro Ser Ser Glu Asp Asp Asp
                405                 410                 415

Asp Asp Asp Asp Ser Ser Ser Glu Glu Lys Glu Thr Asp Asn Thr Lys
            420                 425                 430

Pro Asn Pro Val Ala Pro Tyr Trp Thr Ser Pro Glu Lys Met Glu Lys
        435                 440                 445

Lys Leu His Ala Val Pro Ala Ala Lys Thr Val Lys Phe Lys Cys Pro
    450                 455                 460

Ser Ser Gly Thr Pro Asn Pro Thr Leu Arg Trp Leu Lys Asn Gly Lys
465                 470                 475                 480

Glu Phe Lys Pro Asp His Arg Ile Gly Gly Tyr Lys Val Arg Tyr Ala
                485                 490                 495

Thr Trp Ser Ile Ile Met Asp Ser Val Val Pro Ser Asp Lys Gly Asn
            500                 505                 510

Tyr Thr Cys Ile Val Glu Asn Glu Tyr Gly Ser Ile Asn His Thr Tyr
        515                 520                 525

Gln Leu Asp Val Val Glu Arg Ser Pro His Arg Pro Ile Leu Gln Ala
    530                 535                 540

Gly Leu Pro Ala Asn Lys Thr Val Ala Leu Gly Ser Asn Val Glu Phe
545                 550                 555                 560

Met Cys Lys Val Tyr Ser Asp Pro Gln Pro His Ile Gln Trp Leu Lys
                565                 570                 575

His Ile Glu Val Asn Gly Ser Lys Ile Gly Pro Asp Asn Leu Pro Tyr
            580                 585                 590

Val Gln Ile Leu Lys Thr Ala Gly Val Asn Thr Thr Asp Lys Glu Met
        595                 600                 605

Glu Val Leu His Leu Arg Asn Val Ser Phe Glu Asp Ala Gly Glu Tyr
    610                 615                 620

Thr Cys Leu Ala Gly Asn Ser Ile Gly Leu Ser His His Ser Ala Trp
625                 630                 635                 640

Leu Thr Val Leu Glu Ala Leu Glu Glu Arg Pro Ala Val Met Thr Ser
                645                 650                 655

Pro Leu Tyr Leu Glu Asp Lys Thr His Thr Cys Pro Pro Cys Pro Ala
            660                 665                 670

Pro Glu Leu Leu Gly Gly Pro Ser Val Phe Leu Phe Pro Pro Lys Pro
        675                 680                 685

Lys Asp Thr Leu Met Ile Ser Arg Thr Pro Glu Val Thr Cys Val Val
    690                 695                 700

Val Asp Val Ser His Glu Asp Pro Glu Val Lys Phe Asn Trp Tyr Val
705                 710                 715                 720

Asp Gly Val Glu Val His Asn Ala Lys Thr Lys Pro Arg Glu Glu Gln
                725                 730                 735

Tyr Asn Ser Thr Tyr Arg Val Val Ser Val Leu Thr Val Leu His Gln
            740                 745                 750

Asp Trp Leu Asn Gly Lys Glu Tyr Lys Cys Lys Val Ser Asn Lys Ala
        755                 760                 765

Leu Pro Ala Pro Ile Glu Lys Thr Ile Ser Lys Ala Lys Gly Gln Pro
    770                 775                 780

Arg Glu Pro Gln Val Tyr Thr Leu Pro Pro Ser Arg Asp Glu Leu Thr
785                 790                 795                 800
```

```
Lys Asn Gln Val Ser Leu Thr Cys Leu Val Lys Gly Phe Tyr Pro Ser
                805                 810                 815

Asp Ile Ala Val Glu Trp Glu Ser Asn Gly Gln Pro Glu Asn Asn Tyr
            820                 825                 830

Lys Thr Thr Pro Pro Val Leu Asp Ser Asp Gly Ser Phe Phe Leu Tyr
        835                 840                 845

Ser Lys Leu Thr Val Asp Lys Ser Arg Trp Gln Gln Gly Asn Val Phe
    850                 855                 860

Ser Cys Ser Val Met His Glu Ala Leu His Asn His Tyr Thr Gln Lys
865                 870                 875                 880

Ser Leu Ser Leu Ser Pro Gly Lys
                885


<210> SEQ ID NO 19
<211> LENGTH: 833
<212> TYPE: PRT
<213> ORGANISM: artificial
<220> FEATURE:
<223> OTHER INFORMATION: fused protein

<400> SEQUENCE: 19

Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Val Leu
        195                 200                 205

Ser Pro Ser His Gly Ile Glu Leu Ser Val Gly Glu Lys Leu Val Leu
    210                 215                 220

Asn Cys Thr Ala Arg Thr Glu Leu Asn Val Gly Ile Asp Phe Asn Trp
225                 230                 235                 240

Glu Tyr Pro Ser Ser Lys His Gln His Lys Lys Leu Val Asn Arg Asp
                245                 250                 255

Leu Lys Thr Gln Ser Gly Ser Glu Met Lys Lys Phe Leu Ser Thr Leu
            260                 265                 270
```

-continued

```
Thr Ile Asp Gly Val Thr Arg Ser Asp Gln Gly Leu Tyr Thr Cys Ala
        275                 280                 285

Ala Ser Ser Gly Leu Met Thr Lys Lys Asn Ser Thr Phe Val Arg Val
    290                 295                 300

His Glu Lys Pro Asn Arg Thr Arg Ile Thr Gly Glu Glu Val Glu Val
305                 310                 315                 320

Gln Asp Ser Val Pro Ala Asp Ser Gly Leu Tyr Ala Cys Val Thr Ser
                325                 330                 335

Ser Pro Ser Gly Ser Asp Thr Thr Tyr Phe Ser Val Asn Val Ser Asp
            340                 345                 350

Ala Leu Pro Ser Ser Glu Asp Asp Asp Asp Asp Asp Asp Ser Ser Ser
        355                 360                 365

Glu Glu Lys Glu Thr Asp Asn Thr Lys Pro Asn Pro Val Ala Pro Tyr
    370                 375                 380

Trp Thr Ser Pro Glu Lys Met Glu Lys Lys Leu His Ala Val Pro Ala
385                 390                 395                 400

Ala Lys Thr Val Lys Phe Lys Cys Pro Ser Ser Gly Thr Pro Asn Pro
                405                 410                 415

Thr Leu Arg Trp Leu Lys Asn Gly Lys Glu Phe Lys Pro Asp His Arg
            420                 425                 430

Ile Gly Gly Tyr Lys Val Arg Tyr Ala Thr Trp Ser Ile Ile Met Asp
        435                 440                 445

Ser Val Val Pro Ser Asp Lys Gly Asn Tyr Thr Cys Ile Val Glu Asn
    450                 455                 460

Glu Tyr Gly Ser Ile Asn His Thr Tyr Gln Leu Asp Val Val Glu Arg
465                 470                 475                 480

Ser Pro His Arg Pro Ile Leu Gln Ala Gly Leu Pro Ala Asn Lys Thr
                485                 490                 495

Val Ala Leu Gly Ser Asn Val Glu Phe Met Cys Lys Val Tyr Ser Asp
            500                 505                 510

Pro Gln Pro His Ile Gln Trp Leu Lys His Ile Glu Val Asn Gly Ser
        515                 520                 525

Lys Ile Gly Pro Asp Asn Leu Pro Tyr Val Gln Ile Leu Lys Thr Ala
    530                 535                 540

Gly Val Asn Thr Thr Asp Lys Glu Met Glu Val Leu His Leu Arg Asn
545                 550                 555                 560

Val Ser Phe Glu Asp Ala Gly Glu Tyr Thr Cys Leu Ala Gly Asn Ser
                565                 570                 575

Ile Gly Leu Ser His His Ser Ala Trp Leu Thr Val Leu Glu Ala Leu
            580                 585                 590

Glu Glu Arg Pro Ala Val Met Thr Ser Pro Leu Tyr Leu Glu Asp Lys
        595                 600                 605

Thr His Thr Cys Pro Pro Cys Pro Ala Pro Glu Leu Leu Gly Gly Pro
    610                 615                 620

Ser Val Phe Leu Phe Pro Pro Lys Pro Lys Asp Thr Leu Met Ile Ser
625                 630                 635                 640

Arg Thr Pro Glu Val Thr Cys Val Val Val Asp Val Ser His Glu Asp
                645                 650                 655

Pro Glu Val Lys Phe Asn Trp Tyr Val Asp Gly Val Glu Val His Asn
            660                 665                 670

Ala Lys Thr Lys Pro Arg Glu Glu Gln Tyr Asn Ser Thr Tyr Arg Val
        675                 680                 685
```

Val Ser Val Leu Thr Val Leu His Gln Asp Trp Leu Asn Gly Lys Glu
690 695 700

Tyr Lys Cys Lys Val Ser Asn Lys Ala Leu Pro Ala Pro Ile Glu Lys
705 710 715 720

Thr Ile Ser Lys Ala Lys Gly Gln Pro Arg Glu Pro Gln Val Tyr Thr
725 730 735

Leu Pro Pro Ser Arg Asp Glu Leu Thr Lys Asn Gln Val Ser Leu Thr
740 745 750

Cys Leu Val Lys Gly Phe Tyr Pro Ser Asp Ile Ala Val Glu Trp Glu
755 760 765

Ser Asn Gly Gln Pro Glu Asn Asn Tyr Lys Thr Thr Pro Pro Val Leu
770 775 780

Asp Ser Asp Gly Ser Phe Phe Leu Tyr Ser Lys Leu Thr Val Asp Lys
785 790 795 800

Ser Arg Trp Gln Gln Gly Asn Val Phe Ser Cys Ser Val Met His Glu
805 810 815

Ala Leu His Asn His Tyr Thr Gln Lys Ser Leu Ser Leu Ser Pro Gly
820 825 830

Lys

<210> SEQ ID NO 20
<211> LENGTH: 834
<212> TYPE: PRT
<213> ORGANISM: artificial
<220> FEATURE:
<223> OTHER INFORMATION: fused protein

<400> SEQUENCE: 20

Ser Lys Leu Lys Asp Pro Glu Leu Ser Leu Lys Gly Thr Gln His Ile
1 5 10 15

Met Gln Ala Gly Gln Thr Leu His Leu Gln Cys Arg Gly Glu Ala Ala
20 25 30

His Lys Trp Ser Leu Pro Glu Met Val Ser Lys Glu Ser Glu Arg Leu
35 40 45

Ser Ile Thr Lys Ser Ala Cys Gly Arg Asn Gly Lys Gln Phe Cys Ser
50 55 60

Thr Leu Thr Leu Asn Thr Ala Gln Ala Asn His Thr Gly Phe Tyr Ser
65 70 75 80

Cys Lys Tyr Leu Ala Val Pro Thr Ser Lys Lys Lys Glu Thr Glu Ser
85 90 95

Ala Ile Tyr Ile Phe Ile Ser Asp Thr Gly Arg Pro Phe Val Glu Met
100 105 110

Tyr Ser Glu Ile Pro Glu Ile Ile His Met Thr Glu Gly Arg Glu Leu
115 120 125

Val Ile Pro Cys Arg Val Thr Ser Pro Asn Ile Thr Val Thr Leu Lys
130 135 140

Lys Phe Pro Leu Asp Thr Leu Ile Pro Asp Gly Lys Arg Ile Ile Trp
145 150 155 160

Asp Ser Arg Lys Gly Phe Ile Ile Ser Asn Ala Thr Tyr Lys Glu Ile
165 170 175

Gly Leu Leu Thr Cys Glu Ala Thr Val Asn Gly His Leu Tyr Lys Thr
180 185 190

Asn Tyr Leu Thr His Arg Gln Thr Asn Thr Ile Ile Asp Val Val Leu
195 200 205

Ser Pro Ser His Gly Ile Glu Leu Ser Val Gly Glu Lys Leu Val Leu

```
    210                 215                 220

Asn Cys Thr Ala Arg Thr Glu Leu Asn Val Gly Ile Asp Phe Asn Trp
225                 230                 235                 240

Glu Tyr Pro Ser Ser Lys His Gln His Lys Lys Leu Val Asn Arg Asp
                245                 250                 255

Leu Lys Thr Gln Ser Gly Ser Glu Met Lys Lys Phe Leu Ser Thr Leu
            260                 265                 270

Thr Ile Asp Gly Val Thr Arg Ser Asp Gln Gly Leu Tyr Thr Cys Ala
        275                 280                 285

Ala Ser Ser Gly Leu Met Thr Lys Lys Asn Ser Thr Phe Val Arg Val
    290                 295                 300

His Glu Lys Pro Lys Asn Arg Thr Arg Ile Thr Gly Glu Glu Val Glu
305                 310                 315                 320

Val Gln Asp Ser Val Pro Ala Asp Ser Gly Leu Tyr Ala Ser Val Thr
                325                 330                 335

Ser Ser Pro Ser Gly Ser Asp Thr Thr Tyr Phe Ser Val Asn Val Ser
            340                 345                 350

Asp Ala Leu Pro Ser Ser Glu Asp Asp Asp Asp Asp Asp Asp Ser Ser
        355                 360                 365

Ser Glu Glu Lys Glu Thr Asp Asn Thr Lys Pro Asn Pro Val Ala Pro
    370                 375                 380

Tyr Trp Thr Ser Pro Glu Lys Met Glu Lys Lys Leu His Ala Val Pro
385                 390                 395                 400

Ala Ala Lys Thr Val Lys Phe Lys Cys Pro Ser Ser Gly Thr Pro Asn
                405                 410                 415

Pro Thr Leu Arg Trp Leu Lys Asn Gly Lys Glu Phe Lys Pro Asp His
            420                 425                 430

Arg Ile Gly Gly Tyr Lys Val Arg Tyr Ala Thr Trp Ser Ile Ile Met
        435                 440                 445

Asp Ser Val Val Pro Ser Asp Lys Gly Asn Tyr Thr Cys Ile Val Glu
    450                 455                 460

Asn Glu Tyr Gly Ser Ile Asn His Thr Tyr Gln Leu Asp Val Val Glu
465                 470                 475                 480

Arg Ser Pro His Arg Pro Ile Leu Gln Ala Gly Leu Pro Ala Asn Lys
                485                 490                 495

Thr Val Ala Leu Gly Ser Asn Val Glu Phe Met Cys Lys Val Tyr Ser
            500                 505                 510

Asp Pro Gln Pro His Ile Gln Trp Leu Lys His Ile Glu Val Asn Gly
        515                 520                 525

Ser Lys Ile Gly Pro Asp Asn Leu Pro Tyr Val Gln Ile Leu Lys Thr
    530                 535                 540

Ala Gly Val Asn Thr Thr Asp Lys Glu Met Glu Val Leu His Leu Arg
545                 550                 555                 560

Asn Val Ser Phe Glu Asp Ala Gly Glu Tyr Thr Cys Leu Ala Gly Asn
                565                 570                 575

Ser Ile Gly Leu Ser His His Ser Ala Trp Leu Thr Val Leu Glu Ala
            580                 585                 590

Leu Glu Glu Arg Pro Ala Val Met Thr Ser Pro Leu Tyr Leu Glu Asp
        595                 600                 605

Lys Thr His Thr Cys Pro Pro Cys Pro Ala Pro Glu Leu Leu Gly Gly
    610                 615                 620

Pro Ser Val Phe Leu Phe Pro Pro Lys Pro Lys Asp Thr Leu Met Ile
625                 630                 635                 640
```

```
Ser Arg Thr Pro Glu Val Thr Cys Val Val Val Asp Val Ser His Glu
                645                 650                 655

Asp Pro Glu Val Lys Phe Asn Trp Tyr Val Asp Gly Val Glu Val His
            660                 665                 670

Asn Ala Lys Thr Lys Pro Arg Glu Glu Gln Tyr Asn Ser Thr Tyr Arg
        675                 680                 685

Val Val Ser Val Leu Thr Val Leu His Gln Asp Trp Leu Asn Gly Lys
    690                 695                 700

Glu Tyr Lys Cys Lys Val Ser Asn Lys Ala Leu Pro Ala Pro Ile Glu
705                 710                 715                 720

Lys Thr Ile Ser Lys Ala Lys Gly Gln Pro Arg Glu Pro Gln Val Tyr
                725                 730                 735

Thr Leu Pro Pro Ser Arg Asp Glu Leu Thr Lys Asn Gln Val Ser Leu
            740                 745                 750

Thr Cys Leu Val Lys Gly Phe Tyr Pro Ser Asp Ile Ala Val Glu Trp
        755                 760                 765

Glu Ser Asn Gly Gln Pro Glu Asn Asn Tyr Lys Thr Thr Pro Pro Val
    770                 775                 780

Leu Asp Ser Asp Gly Ser Phe Phe Leu Tyr Ser Lys Leu Thr Val Asp
785                 790                 795                 800

Lys Ser Arg Trp Gln Gln Gly Asn Val Phe Ser Cys Ser Val Met His
                805                 810                 815

Glu Ala Leu His Asn His Tyr Thr Gln Lys Ser Leu Ser Leu Ser Pro
            820                 825                 830

Gly Lys


<210> SEQ ID NO 21
<211> LENGTH: 803
<212> TYPE: PRT
<213> ORGANISM: artificial
<220> FEATURE:
<223> OTHER INFORMATION: fused protein

<400> SEQUENCE: 21

Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160
```

-continued

```
Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Val Leu
        195                 200                 205

Ser Pro Ser His Gly Ile Glu Leu Ser Val Gly Glu Lys Leu Val Leu
    210                 215                 220

Asn Cys Thr Ala Arg Thr Glu Leu Asn Val Gly Ile Asp Phe Asn Trp
225                 230                 235                 240

Glu Tyr Pro Ser Ser Lys His Gln His Lys Lys Leu Val Asn Arg Asp
                245                 250                 255

Leu Lys Thr Gln Ser Gly Ser Glu Met Lys Lys Phe Leu Ser Thr Leu
            260                 265                 270

Thr Ile Asp Gly Val Thr Arg Ser Asp Gln Gly Leu Tyr Thr Cys Ala
        275                 280                 285

Ala Ser Ser Gly Leu Met Thr Lys Lys Asn Ser Thr Phe Val Arg Val
    290                 295                 300

His Glu Lys Pro Ser Gly Ser Asp Thr Thr Tyr Phe Ser Val Asn Val
305                 310                 315                 320

Ser Asp Ala Leu Pro Ser Ser Glu Asp Asp Asp Asp Asp Asp Asp Ser
                325                 330                 335

Ser Ser Glu Glu Lys Glu Thr Asp Asn Thr Lys Pro Asn Pro Val Ala
            340                 345                 350

Pro Tyr Trp Thr Ser Pro Glu Lys Met Glu Lys Lys Leu His Ala Val
        355                 360                 365

Pro Ala Ala Lys Thr Val Lys Phe Lys Cys Pro Ser Ser Gly Thr Pro
    370                 375                 380

Asn Pro Thr Leu Arg Trp Leu Lys Asn Gly Lys Glu Phe Lys Pro Asp
385                 390                 395                 400

His Arg Ile Gly Gly Tyr Lys Val Arg Tyr Ala Thr Trp Ser Ile Ile
                405                 410                 415

Met Asp Ser Val Val Pro Ser Asp Lys Gly Asn Tyr Thr Cys Ile Val
            420                 425                 430

Glu Asn Glu Tyr Gly Ser Ile Asn His Thr Tyr Gln Leu Asp Val Val
        435                 440                 445

Glu Arg Ser Pro His Arg Pro Ile Leu Gln Ala Gly Leu Pro Ala Asn
    450                 455                 460

Lys Thr Val Ala Leu Gly Ser Asn Val Glu Phe Met Cys Lys Val Tyr
465                 470                 475                 480

Ser Asp Pro Gln Pro His Ile Gln Trp Leu Lys His Ile Glu Val Asn
                485                 490                 495

Gly Ser Lys Ile Gly Pro Asp Asn Leu Pro Tyr Val Gln Ile Leu Lys
            500                 505                 510

Thr Ala Gly Val Asn Thr Thr Asp Lys Glu Met Glu Val Leu His Leu
        515                 520                 525

Arg Asn Val Ser Phe Glu Asp Ala Gly Glu Tyr Thr Cys Leu Ala Gly
    530                 535                 540

Asn Ser Ile Gly Leu Ser His His Ser Ala Trp Leu Thr Val Leu Glu
545                 550                 555                 560

Ala Leu Glu Glu Arg Pro Ala Val Met Thr Ser Pro Leu Tyr Leu Glu
                565                 570                 575

Asp Lys Thr His Thr Cys Pro Pro Cys Pro Ala Pro Glu Leu Leu Gly
```

```
            580                 585                 590

Gly Pro Ser Val Phe Leu Phe Pro Pro Lys Pro Lys Asp Thr Leu Met
        595                 600                 605

Ile Ser Arg Thr Pro Glu Val Thr Cys Val Val Val Asp Val Ser His
    610                 615                 620

Glu Asp Pro Glu Val Lys Phe Asn Trp Tyr Val Asp Gly Val Glu Val
625                 630                 635                 640

His Asn Ala Lys Thr Lys Pro Arg Glu Glu Gln Tyr Asn Ser Thr Tyr
                645                 650                 655

Arg Val Val Ser Val Leu Thr Val Leu His Gln Asp Trp Leu Asn Gly
            660                 665                 670

Lys Glu Tyr Lys Cys Lys Val Ser Asn Lys Ala Leu Pro Ala Pro Ile
        675                 680                 685

Glu Lys Thr Ile Ser Lys Ala Lys Gly Gln Pro Arg Glu Pro Gln Val
    690                 695                 700

Tyr Thr Leu Pro Pro Ser Arg Asp Glu Leu Thr Lys Asn Gln Val Ser
705                 710                 715                 720

Leu Thr Cys Leu Val Lys Gly Phe Tyr Pro Ser Asp Ile Ala Val Glu
                725                 730                 735

Trp Glu Ser Asn Gly Gln Pro Glu Asn Asn Tyr Lys Thr Thr Pro Pro
            740                 745                 750

Val Leu Asp Ser Asp Gly Ser Phe Phe Leu Tyr Ser Lys Leu Thr Val
        755                 760                 765

Asp Lys Ser Arg Trp Gln Gln Gly Asn Val Phe Ser Cys Ser Val Met
    770                 775                 780

His Glu Ala Leu His Asn His Tyr Thr Gln Lys Ser Leu Ser Leu Ser
785                 790                 795                 800

Pro Gly Lys


<210> SEQ ID NO 22
<211> LENGTH: 763
<212> TYPE: PRT
<213> ORGANISM: artificial
<220> FEATURE:
<223> OTHER INFORMATION: fused protein

<400> SEQUENCE: 22

Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140
```

-continued

```
Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Val Leu
        195                 200                 205

Ser Pro Ser His Gly Ile Glu Leu Ser Val Gly Glu Lys Leu Val Leu
    210                 215                 220

Asn Cys Thr Ala Arg Thr Glu Leu Asn Val Gly Ile Asp Phe Asn Trp
225                 230                 235                 240

Glu Tyr Pro Ser Ser Lys His Gln His Lys Lys Leu Val Asn Arg Asp
                245                 250                 255

Leu Lys Thr Gln Ser Gly Ser Glu Met Lys Lys Phe Leu Ser Thr Leu
            260                 265                 270

Thr Ile Asp Gly Val Thr Arg Ser Asp Gln Gly Leu Tyr Thr Cys Ala
        275                 280                 285

Ala Ser Ser Gly Leu Met Thr Lys Lys Asn Ser Thr Phe Val Arg Val
    290                 295                 300

His Glu Lys Pro Asn Pro Val Ala Pro Tyr Trp Thr Ser Pro Glu Lys
305                 310                 315                 320

Met Glu Lys Lys Leu His Ala Val Pro Ala Ala Lys Thr Val Lys Phe
                325                 330                 335

Lys Cys Pro Ser Ser Gly Thr Pro Asn Pro Thr Leu Arg Trp Leu Lys
            340                 345                 350

Asn Gly Lys Glu Phe Lys Pro Asp His Arg Ile Gly Gly Tyr Lys Val
        355                 360                 365

Arg Tyr Ala Thr Trp Ser Ile Ile Met Asp Ser Val Val Pro Ser Asp
    370                 375                 380

Lys Gly Asn Tyr Thr Cys Ile Val Glu Asn Glu Tyr Gly Ser Ile Asn
385                 390                 395                 400

His Thr Tyr Gln Leu Asp Val Val Glu Arg Ser Pro His Arg Pro Ile
                405                 410                 415

Leu Gln Ala Gly Leu Pro Ala Asn Lys Thr Val Ala Leu Gly Ser Asn
            420                 425                 430

Val Glu Phe Met Cys Lys Val Tyr Ser Asp Pro Gln Pro His Ile Gln
        435                 440                 445

Trp Leu Lys His Ile Glu Val Asn Gly Ser Lys Ile Gly Pro Asp Asn
    450                 455                 460

Leu Pro Tyr Val Gln Ile Leu Lys Thr Ala Gly Val Asn Thr Thr Asp
465                 470                 475                 480

Lys Glu Met Glu Val Leu His Leu Arg Asn Val Ser Phe Glu Asp Ala
                485                 490                 495

Gly Glu Tyr Thr Cys Leu Ala Gly Asn Ser Ile Gly Leu Ser His His
            500                 505                 510

Ser Ala Trp Leu Thr Val Leu Glu Ala Leu Glu Glu Arg Pro Ala Val
        515                 520                 525

Met Thr Ser Pro Leu Tyr Leu Glu Asp Lys Thr His Thr Cys Pro Pro
    530                 535                 540

Cys Pro Ala Pro Glu Leu Leu Gly Gly Pro Ser Val Phe Leu Phe Pro
545                 550                 555                 560
```

```
Pro Lys Pro Lys Asp Thr Leu Met Ile Ser Arg Thr Pro Glu Val Thr
                565                 570                 575

Cys Val Val Val Asp Val Ser His Glu Asp Pro Glu Val Lys Phe Asn
            580                 585                 590

Trp Tyr Val Asp Gly Val Glu Val His Asn Ala Lys Thr Lys Pro Arg
        595                 600                 605

Glu Glu Gln Tyr Asn Ser Thr Tyr Arg Val Val Ser Val Leu Thr Val
    610                 615                 620

Leu His Gln Asp Trp Leu Asn Gly Lys Glu Tyr Lys Cys Lys Val Ser
625                 630                 635                 640

Asn Lys Ala Leu Pro Ala Pro Ile Glu Lys Thr Ile Ser Lys Ala Lys
                645                 650                 655

Gly Gln Pro Arg Glu Pro Gln Val Tyr Thr Leu Pro Pro Ser Arg Asp
            660                 665                 670

Glu Leu Thr Lys Asn Gln Val Ser Leu Thr Cys Leu Val Lys Gly Phe
        675                 680                 685

Tyr Pro Ser Asp Ile Ala Val Glu Trp Glu Ser Asn Gly Gln Pro Glu
    690                 695                 700

Asn Asn Tyr Lys Thr Thr Pro Pro Val Leu Asp Ser Asp Gly Ser Phe
705                 710                 715                 720

Phe Leu Tyr Ser Lys Leu Thr Val Asp Lys Ser Arg Trp Gln Gln Gly
                725                 730                 735

Asn Val Phe Ser Cys Ser Val Met His Glu Ala Leu His Asn His Tyr
            740                 745                 750

Thr Gln Lys Ser Leu Ser Leu Ser Pro Gly Lys
        755                 760
```

<210> SEQ ID NO 23
<211> LENGTH: 765
<212> TYPE: PRT
<213> ORGANISM: artificial
<220> FEATURE:
<223> OTHER INFORMATION: fused protein

<400> SEQUENCE: 23

```
Lys Pro Asn Pro Val Ala Pro Tyr Trp Thr Ser Pro Glu Lys Met Glu
1               5                   10                  15

Lys Lys Leu His Ala Val Pro Ala Ala Lys Thr Val Lys Phe Lys Cys
            20                  25                  30

Pro Ser Ser Gly Thr Pro Asn Pro Thr Leu Arg Trp Leu Lys Asn Gly
        35                  40                  45

Lys Glu Phe Lys Pro Asp His Arg Ile Gly Gly Tyr Lys Val Arg Tyr
    50                  55                  60

Ala Thr Trp Ser Ile Ile Met Asp Ser Val Val Pro Ser Asp Lys Gly
65                  70                  75                  80

Asn Tyr Thr Cys Ile Val Glu Asn Glu Tyr Gly Ser Ile Asn His Thr
                85                  90                  95

Tyr Gln Leu Asp Val Val Glu Arg Ser Pro His Arg Pro Ile Leu Gln
            100                 105                 110

Ala Gly Leu Pro Ala Asn Lys Thr Val Ala Leu Gly Ser Asn Val Glu
        115                 120                 125

Phe Met Cys Lys Val Tyr Ser Asp Pro Gln Pro His Ile Gln Trp Leu
    130                 135                 140

Lys His Ile Glu Val Asn Gly Ser Lys Ile Gly Pro Asp Asn Leu Pro
145                 150                 155                 160
```

-continued

```
Tyr Val Gln Ile Leu Lys Thr Ala Gly Val Asn Thr Thr Asp Lys Glu
                165                 170                 175

Met Glu Val Leu His Leu Arg Asn Val Ser Phe Glu Asp Ala Gly Glu
            180                 185                 190

Tyr Thr Cys Leu Ala Gly Asn Ser Ile Gly Leu Ser His His Ser Ala
        195                 200                 205

Trp Leu Thr Val Leu Glu Ala Leu Glu Glu Arg Pro Ala Val Met Thr
    210                 215                 220

Ser Pro Leu Tyr Leu Glu Ser Lys Leu Lys Asp Pro Glu Leu Ser Leu
225                 230                 235                 240

Lys Gly Thr Gln His Ile Met Gln Ala Gly Gln Thr Leu His Leu Gln
                245                 250                 255

Cys Arg Gly Glu Ala Ala His Lys Trp Ser Leu Pro Glu Met Val Ser
            260                 265                 270

Lys Glu Ser Glu Arg Leu Ser Ile Thr Lys Ser Ala Cys Gly Arg Asn
        275                 280                 285

Gly Lys Gln Phe Cys Ser Thr Leu Thr Leu Asn Thr Ala Gln Ala Asn
    290                 295                 300

His Thr Gly Phe Tyr Ser Cys Lys Tyr Leu Ala Val Pro Thr Ser Lys
305                 310                 315                 320

Lys Lys Glu Thr Glu Ser Ala Ile Tyr Ile Phe Ile Ser Asp Thr Gly
                325                 330                 335

Arg Pro Phe Val Glu Met Tyr Ser Glu Ile Pro Glu Ile Ile His Met
            340                 345                 350

Thr Glu Gly Arg Glu Leu Val Ile Pro Cys Arg Val Thr Ser Pro Asn
        355                 360                 365

Ile Thr Val Thr Leu Lys Lys Phe Pro Leu Asp Thr Leu Ile Pro Asp
    370                 375                 380

Gly Lys Arg Ile Ile Trp Asp Ser Arg Lys Gly Phe Ile Ile Ser Asn
385                 390                 395                 400

Ala Thr Tyr Lys Glu Ile Gly Leu Leu Thr Cys Glu Ala Thr Val Asn
                405                 410                 415

Gly His Leu Tyr Lys Thr Asn Tyr Leu Thr His Arg Gln Thr Asn Thr
            420                 425                 430

Ile Ile Asp Val Val Leu Ser Pro Ser His Gly Ile Glu Leu Ser Val
        435                 440                 445

Gly Glu Lys Leu Val Leu Asn Cys Thr Ala Arg Thr Glu Leu Asn Val
    450                 455                 460

Gly Ile Asp Phe Asn Trp Glu Tyr Pro Ser Ser Lys His Gln His Lys
465                 470                 475                 480

Lys Leu Val Asn Arg Asp Leu Lys Thr Gln Ser Gly Ser Glu Met Lys
                485                 490                 495

Lys Phe Leu Ser Thr Leu Thr Ile Asp Gly Val Thr Arg Ser Asp Gln
            500                 505                 510

Gly Leu Tyr Thr Cys Ala Ala Ser Ser Gly Leu Met Thr Lys Lys Asn
        515                 520                 525

Ser Thr Phe Val Arg Val His Glu Lys Pro Asp Lys Thr His Thr Cys
    530                 535                 540

Pro Pro Cys Pro Ala Pro Glu Leu Leu Gly Gly Pro Ser Val Phe Leu
545                 550                 555                 560

Phe Pro Pro Lys Pro Lys Asp Thr Leu Met Ile Ser Arg Thr Pro Glu
                565                 570                 575

Val Thr Cys Val Val Val Asp Val Ser His Glu Asp Pro Glu Val Lys
```

-continued

```
            580                 585                 590

Phe Asn Trp Tyr Val Asp Gly Val Glu Val His Asn Ala Lys Thr Lys
        595                 600                 605

Pro Arg Glu Glu Gln Tyr Asn Ser Thr Tyr Arg Val Val Ser Val Leu
    610                 615                 620

Thr Val Leu His Gln Asp Trp Leu Asn Gly Lys Glu Tyr Lys Cys Lys
625                 630                 635                 640

Val Ser Asn Lys Ala Leu Pro Ala Pro Ile Glu Lys Thr Ile Ser Lys
                645                 650                 655

Ala Lys Gly Gln Pro Arg Glu Pro Gln Val Tyr Thr Leu Pro Pro Ser
            660                 665                 670

Arg Asp Glu Leu Thr Lys Asn Gln Val Ser Leu Thr Cys Leu Val Lys
        675                 680                 685

Gly Phe Tyr Pro Ser Asp Ile Ala Val Glu Trp Glu Ser Asn Gly Gln
    690                 695                 700

Pro Glu Asn Asn Tyr Lys Thr Thr Pro Pro Val Leu Asp Ser Asp Gly
705                 710                 715                 720

Ser Phe Phe Leu Tyr Ser Lys Leu Thr Val Asp Lys Ser Arg Trp Gln
                725                 730                 735

Gln Gly Asn Val Phe Ser Cys Ser Val Met His Glu Ala Leu His Asn
            740                 745                 750

His Tyr Thr Gln Lys Ser Leu Ser Leu Ser Pro Gly Lys
        755                 760                 765


<210> SEQ ID NO 24
<211> LENGTH: 658
<212> TYPE: PRT
<213> ORGANISM: artificial
<220> FEATURE:
<223> OTHER INFORMATION: fused protein

<400> SEQUENCE: 24

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
```

-continued

```
            180                 185                 190

Asn Ser Thr Phe Val Arg Val His Glu Lys Pro Asn Pro Val Ala Pro
        195                 200                 205

Tyr Trp Thr Ser Pro Glu Lys Met Glu Lys Lys Leu His Ala Val Pro
    210                 215                 220

Ala Ala Lys Thr Val Lys Phe Lys Cys Pro Ser Ser Gly Thr Pro Asn
225                 230                 235                 240

Pro Thr Leu Arg Trp Leu Lys Asn Gly Lys Glu Phe Lys Pro Asp His
                245                 250                 255

Arg Ile Gly Gly Tyr Lys Val Arg Tyr Ala Thr Trp Ser Ile Ile Met
            260                 265                 270

Asp Ser Val Val Pro Ser Asp Lys Gly Asn Tyr Thr Cys Ile Val Glu
        275                 280                 285

Asn Glu Tyr Gly Ser Ile Asn His Thr Tyr Gln Leu Asp Val Val Glu
    290                 295                 300

Arg Ser Pro His Arg Pro Ile Leu Gln Ala Gly Leu Pro Ala Asn Lys
305                 310                 315                 320

Thr Val Ala Leu Gly Ser Asn Val Glu Phe Met Cys Lys Val Tyr Ser
                325                 330                 335

Asp Pro Gln Pro His Ile Gln Trp Leu Lys His Ile Glu Val Asn Gly
            340                 345                 350

Ser Lys Ile Gly Pro Asp Asn Leu Pro Tyr Val Gln Ile Leu Lys Thr
        355                 360                 365

Ala Gly Val Asn Thr Thr Asp Lys Glu Met Glu Val Leu His Leu Arg
    370                 375                 380

Asn Val Ser Phe Glu Asp Ala Gly Glu Tyr Thr Cys Leu Ala Gly Asn
385                 390                 395                 400

Ser Ile Gly Leu Ser His His Ser Ala Trp Leu Thr Val Leu Glu Ala
                405                 410                 415

Leu Glu Glu Arg Pro Ala Val Met Thr Ser Pro Leu Tyr Leu Glu Asp
            420                 425                 430

Lys Thr His Thr Cys Pro Pro Cys Pro Ala Pro Glu Leu Leu Gly Gly
        435                 440                 445

Pro Ser Val Phe Leu Phe Pro Pro Lys Pro Lys Asp Thr Leu Met Ile
    450                 455                 460

Ser Arg Thr Pro Glu Val Thr Cys Val Val Val Asp Val Ser His Glu
465                 470                 475                 480

Asp Pro Glu Val Lys Phe Asn Trp Tyr Val Asp Gly Val Glu Val His
                485                 490                 495

Asn Ala Lys Thr Lys Pro Arg Glu Glu Gln Tyr Asn Ser Thr Tyr Arg
            500                 505                 510

Val Val Ser Val Leu Thr Val Leu His Gln Asp Trp Leu Asn Gly Lys
        515                 520                 525

Glu Tyr Lys Cys Lys Val Ser Asn Lys Ala Leu Pro Ala Pro Ile Glu
    530                 535                 540

Lys Thr Ile Ser Lys Ala Lys Gly Gln Pro Arg Glu Pro Gln Val Tyr
545                 550                 555                 560

Thr Leu Pro Pro Ser Arg Asp Glu Leu Thr Lys Asn Gln Val Ser Leu
                565                 570                 575

Thr Cys Leu Val Lys Gly Phe Tyr Pro Ser Asp Ile Ala Val Glu Trp
            580                 585                 590

Glu Ser Asn Gly Gln Pro Glu Asn Asn Tyr Lys Thr Thr Pro Pro Val
        595                 600                 605
```

-continued

```
Leu Asp Ser Asp Gly Ser Phe Phe Leu Tyr Ser Lys Leu Thr Val Asp
    610                 615                 620

Lys Ser Arg Trp Gln Gln Gly Asn Val Phe Ser Cys Ser Val Met His
625                 630                 635                 640

Glu Ala Leu His Asn His Tyr Thr Gln Lys Ser Leu Ser Leu Ser Pro
                645                 650                 655

Gly Lys


<210> SEQ ID NO 25
<211> LENGTH: 78
<212> TYPE: DNA
<213> ORGANISM: Homo sapiens

<400> SEQUENCE: 25

atggtcagct actgggacac cggggtcctg ctgtgcgcgc tgctcagctg tctgcttctc      60

acaggatcta gttccgga                                                    78


<210> SEQ ID NO 26
<211> LENGTH: 2001
<212> TYPE: DNA
<213> ORGANISM: Artificial
<220> FEATURE:
<223> OTHER INFORMATION: Nucleotide sequence of fused protein

<400> SEQUENCE: 26

ggtagacctt tcgtagagat gtacagtgaa atccccgaaa ttatacacat gactgaagga      60

agggagctcg tcattccctg ccgggttacg tcacctaaca tcactgttac tttaaaaaag     120

tttccacttg acactttgat ccctgatgga aaacgcataa tctgggacag tagaaagggc     180

ttcatcatat caaatgcaac gtacaaagaa atagggcttc tgacctgtga agcaacagtc     240

aatgggcatt tgtataagac aaactatctc acacatcgac aaaccaatac aatcatagat     300

gtccaaataa gcacaccacg cccagtcaaa ttacttagag gccatactct tgtcctcaat     360

tgtactgcta ccactccctt gaacacgaga gttcaaatga cctggagtta ccctgatgaa     420

aaaaatcgca cccgcatcac aggggaggag gtggaggtgc aggactccgt gcccgcagac     480

tccggcctct atgcttgcgt aaccagcagc ccctcgggca gtgacaccac ctacttctcc     540

gtcaatgttt cagatgctct cccctcctcg gaggatgatg atgatgatga tgactcctct     600

tcagaggaga aagaaacaga taacaccaaa ccaaaccccg tagctccata ttggacatcc     660

ccagaaaaga tggaaaagaa attgcatgca gtgccggctg ccaagacagt gaagttcaaa     720

tgcccttcca gtgggacccc aaaccccaca ctgcgctggt tgaaaaatgg caaagaattc     780

aaacctgacc acagaattgg aggctacaag gtccgttatg ccacctggag catcataatg     840

gactctgtgg tgccctctga caagggcaac tacacctgca ttgtggagaa tgagtacggc     900

agcatcaacc acacatacca gctggatgtc gtggagcggt cccctcaccg gcccatcctg     960

caagcagggt tgcccgccaa caaaacagtg gccctgggta gcaacgtgga gttcatgtgt    1020

aaggtgtaca gtgacccgca gccgcacatc cagtggctaa agcacatcga ggtgaatggg    1080

agcaagattg gcccagacaa cctgccttat gtccagatct tgaagactgc tggagttaat    1140

accaccgaca aagagatgga ggtgcttcac ttaagaaatg tctcctttga ggacgcaggg    1200

gagtatacgt gcttggcggg taactctatc ggactctccc atcactctgc atggttgacc    1260

gttctggaag ccctggaaga gaggccggca gtgatgacct cgcccctgta cctggaggac    1320

aaaactcaca catgcccacc gtgcccagca cctgaactcc tgggggggacc gtcagtcttc    1380
```

-continued

```
ctcttccccc caaaacccaa ggacaccctc atgatctccc ggacccctga ggtcacatgc   1440

gtggtggtgg acgtgagcca cgaagaccct gaggtcaagt tcaactggta cgtggacggc   1500

gtggaggtgc ataatgccaa gacaaagccg cgggaggagc agtacaacag cacgtaccgt   1560

gtggtcagcg tcctcaccgt cctgcaccag gactggctga atggcaagga gtacaagtgc   1620

aaggtctcca acaaagccct cccagccccc atcgagaaaa ccatctccaa agccaaaggg   1680

cagccccgag aaccacaggt gtacaccctg cccccatccc gggatgagct gaccaagaac   1740

caggtcagcc tgacctgcct ggtcaaaggc ttctatccca gcgacatcgc cgtggagtgg   1800

gagagcaatg ggcagccgga gaacaactac aagaccacgc ctcccgtgct ggactccgac   1860

ggctccttct tcctctacag caagctcacc gtggacaaga gcaggtggca gcaggggaac   1920

gtcttctcat gctccgtgat gcatgaggct ctgcacaacc actacacgca gaagagcctc   1980

tccctgtctc cgggtaaatg a                                             2001
```

```
<210> SEQ ID NO 27
<211> LENGTH: 1764
<212> TYPE: DNA
<213> ORGANISM: Artificial
<220> FEATURE:
<223> OTHER INFORMATION: Nucleotide sequence of fused protein

<400> SEQUENCE: 27
```

```
ggtagacctt tcgtagagat gtacagtgaa atccccgaaa ttatacacat gactgaagga     60

agggagctcg tcattccctg ccgggttacg tcacctaaca tcactgttac tttaaaaaag    120

tttccacttg acactttgat ccctgatgga aaacgcataa tctgggacag tagaaagggc    180

ttcatcatat caaatgcaac gtacaaagaa atagggcttc tgacctgtga agcaacagtc    240

aatgggcatt tgtataagac aaactatctc acacatcgac aaaccaatac aatcatagat    300

gtccaaataa gcacaccacg cccagtcaaa ttacttagag gccatactct tgtcctcaat    360

tgtactgcta ccactccctt gaacacgaga gttcaaatga cctggagtta ccctgatgaa    420

aaaccagaaa agatggaaaa gaaattgcat gcagtgccgg ctgccaagac agtgaagttc    480

aaatgccctt ccagtgggac cccaaacccc acactgcgct ggttgaaaaa tggcaaagaa    540

ttcaaacctg accacagaat tggaggctac aaggtccgtt atgccacctg gagcatcata    600

atggactctg tggtgccctc tgacaagggc aactacacct gcattgtgga gaatgagtac    660

ggcagcatca accacacata ccagctggat gtcgtggagc ggtcccctca ccggcccatc    720

ctgcaagcag ggttgcccgc caacaaaaca gtggccctgg gtagcaacgt ggagttcatg    780

tgtaaggtgt acagtgaccc gcagccgcac atccagtggc taaagcacat cgaggtgaat    840

gggagcaaga ttggcccaga caacctgcct tatgtccaga tcttgaagac tgctggagtt    900

aataccaccg acaaagagat ggaggtgctt cacttaagaa atgtctcctt tgaggacgca    960

ggggagtata cgtgcttggc gggtaactct atcggactct cccatcactc tgcatggttg   1020

accgttctgg aagccctgga agagaggccg gcagtgatga cctcgcccct gtacctggag   1080

gacaaaactc acacatgccc accgtgccca gcacctgaac tcctgggggg accgtcagtc   1140

ttcctcttcc ccccaaaacc caaggacacc ctcatgatct cccggacccc tgaggtcaca   1200

tgcgtggtgg tggacgtgag ccacgaagac cctgaggtca agttcaactg gtacgtggac   1260

ggcgtggagg tgcataatgc caagacaaag ccgcgggagg agcagtacaa cagcacgtac   1320

cgtgtggtca gcgtcctcac cgtcctgcac caggactggc tgaatggcaa ggagtacaag   1380
```

-continued

```
tgcaaggtct ccaacaaagc cctcccagcc cccatcgaga aaaccatctc caaagccaaa   1440

gggcagcccc gagaaccaca ggtgtacacc ctgcccccat cccgggatga gctgaccaag   1500

aaccaggtca gcctgacctg cctggtcaaa ggcttctatc ccagcgacat cgccgtggag   1560

tgggagagca atgggcagcc ggagaacaac tacaagacca cgcctcccgt gctggactcc   1620

gacggctcct tcttcctcta cagcaagctc accgtggaca agagcaggtg gcagcagggg   1680

aacgtcttct catgctccgt gatgcatgag gctctgcaca accactacac gcagaagagc   1740

ctctccctgt ctccgggtaa atga                                          1764
```

```
<210> SEQ ID NO 28
<211> LENGTH: 1809
<212> TYPE: DNA
<213> ORGANISM: Artificial
<220> FEATURE:
<223> OTHER INFORMATION: Nucleotide sequence of fused protein

<400> SEQUENCE: 28

ggtagacctt tcgtagagat gtacagtgaa atccccgaaa ttatacacat gactgaagga     60

agggagctcg tcattccctg ccgggttacg tcacctaaca tcactgttac tttaaaaaag    120

tttccacttg acactttgat ccctgatgga aaacgcataa tctgggacag tagaaagggc    180

ttcatcatat caaatgcaac gtacaaagaa atagggcttc tgacctgtga agcaacagtc    240

aatgggcatt tgtataagac aaactatctc acacatcgac aaaccaatac aatcatagat    300

gtccaaataa gcacaccacg cccagtcaaa ttacttagag gccatactct tgtcctcaat    360

tgtactgcta ccactccctt gaacacgaga gttcaaatga cctggagtta ccctgatgaa    420

aaaggtggtg gcggttcagg cggaggtggc tctggcggtg gcggatcccc agaaaagatg    480

gaaaagaaat tgcatgcagt gccggctgcc aagacagtga agttcaaatg cccttccagt    540

gggaccccaa accccacact gcgctggttg aaaaatggca aagaattcaa acctgaccac    600

agaattggag gctacaaggt ccgttatgcc acctggagca tcataatgga ctctgtggtg    660

ccctctgaca agggcaacta cacctgcatt gtggagaatg agtacggcag catcaaccac    720

acataccagc tggatgtcgt ggagcggtcc cctcaccggc ccatcctgca agcagggttg    780

cccgccaaca aaacagtggc cctgggtagc aacgtggagt tcatgtgtaa ggtgtacagt    840

gacccgcagc cgcacatcca gtggctaaag cacatcgagg tgaatgggag caagattggc    900

ccagacaacc tgccttatgt ccagatcttg aagactgctg gagttaatac caccgacaaa    960

gagatggagg tgcttcactt aagaaatgtc tcctttgagg acgcagggga gtatacgtgc   1020

ttggcgggta actctatcgg actctcccat cactctgcat ggttgaccgt tctggaagcc   1080

ctggaagaga ggccggcagt gatgacctcg cccctgtacc tggaggacaa aactcacaca   1140

tgcccaccgt gcccagcacc tgaactcctg gggggaccgt cagtcttcct cttcccccca   1200

aaacccaagg acaccctcat gatctcccgg acccctgagg tcacatgcgt ggtggtggac   1260

gtgagccacg aagaccctga ggtcaagttc aactggtacg tggacggcgt ggaggtgcat   1320

aatgccaaga caaagccgcg ggaggagcag tacaacagca cgtaccgtgt ggtcagcgtc   1380

ctcaccgtcc tgcaccagga ctggctgaat ggcaaggagt acaagtgcaa ggtctccaac   1440

aaagccctcc cagcccccat cgagaaaacc atctccaaag ccaaagggca gccccgagaa   1500

ccacaggtgt acaccctgcc cccatcccgg gatgagctga ccaagaacca ggtcagcctg   1560

acctgcctgg tcaaaggctt ctatcccagc gacatcgccg tggagtggga gagcaatggg   1620

cagccggaga acaactacaa gaccacgcct cccgtgctgg actccgacgg ctccttcttc   1680
```

```
ctctacagca agctcaccgt ggacaagagc aggtggcagc aggggaacgt cttctcatgc   1740

tccgtgatgc atgaggctct gcacaaccac tacacgcaga agagcctctc cctgtctccg   1800

ggtaaatga                                                           1809
```

<210> SEQ ID NO 29
<211> LENGTH: 2265
<212> TYPE: DNA
<213> ORGANISM: Artificial
<220> FEATURE:
<223> OTHER INFORMATION: Nucleotide sequence of fused protein

<400> SEQUENCE: 29

```
tcaaaattaa aagatcctga actgagttta aaaggcaccc agcacatcat gcaagcaggc     60

cagacactgc atctccaatg caggggggaa gcagcccata aatggtcttt gcctgaaatg    120

gtgagtaagg aaagcgaaag gctgagcata actaaatctg cctgtggaag aaatggcaaa    180

caattctgta gtactttaac cttgaacaca gctcaagcaa accacactgg cttctacagc    240

tgcaaatatc tagctgtacc tacttcaaag aagaaggaaa cagaatctgc aatctatata    300

tttattagtg atacaggtag acctttcgta gagatgtaca gtgaaatccc cgaaattata    360

cacatgactg aaggaaggga gctcgtcatt ccctgccggg ttacgtcacc taacatcact    420

gttactttaa aaaagtttcc acttgacact ttgatccctg atggaaaacg cataatctgg    480

gacagtagaa agggcttcat catatcaaat gcaacgtaca aagaaatagg gcttctgacc    540

tgtgaagcaa cagtcaatgg gcatttgtat aagacaaact atctcacaca tcgacaaacc    600

aatacaatca tagatgtggt tctgagtccg tctcatggaa ttgaactatc tgttggagaa    660

aagcttgtct taaattgtac agcaagaact gaactaaatg tggggattga cttcaactgg    720

gaataccctt cttcgaagca tcagcataag aaacttgtaa accgagacct aaaaacccag    780

tctgggagtg agatgaagaa atttttgagc accttaacta tagatggtgt aacccggagt    840

gaccaaggat tgtacacctg tgcagcatcc agtgggctga tgaccaagaa gaacagcaca    900

tttgtcaggg tccatgaaaa acctccagaa aagatggaaa agaaattgca tgcagtgccg    960

gctgccaaga cagtgaagtt caaatgccct tccagtggga ccccaaaccc cacactgcgc   1020

tggttgaaaa atggcaaaga attcaaacct gaccacagaa ttggaggcta caaggtccgt   1080

tatgccacct ggagcatcat aatggactct gtggtgccct ctgacaaggg caactacacc   1140

tgcattgtgg agaatgagta cggcagcatc aaccacacat accagctgga tgtcgtggag   1200

cggtcccctc accggcccat cctgcaagca gggttgcccg ccaacaaaac agtggccctg   1260

ggtagcaacg tggagttcat gtgtaaggtg tacagtgacc cgcagccgca catccagtgg   1320

ctaaagcaca tcgaggtgaa tgggagcaag attggcccag acaacctgcc ttatgtccag   1380

atcttgaaga ctgctggagt taataccacc gacaaagaga tggaggtgct tcacttaaga   1440

aatgtctcct ttgaggacgc aggggagtat acgtgcttgg cgggtaactc tatcggactc   1500

tcccatcact ctgcatggtt gaccgttctg gaagccctgg aagagaggcc ggcagtgatg   1560

acctcgcccc tgtacctgga ggacaaaact cacacatgcc caccgtgccc agcacctgaa   1620

ctcctggggg gaccgtcagt cttcctcttc cccccaaaac ccaaggacac cctcatgatc   1680

tcccggaccc ctgaggtcac atgcgtggtg gtggacgtga gccacgaaga ccctgaggtc   1740

aagttcaact ggtacgtgga cggcgtggag gtgcataatg ccaagacaaa gccgcgggag   1800

gagcagtaca acagcacgta ccgtgtggtc agcgtcctca ccgtcctgca ccaggactgg   1860
```

```
ctgaatggca aggagtacaa gtgcaaggtc tccaacaaag ccctcccagc ccccatcgag   1920

aaaaccatct ccaaagccaa agggcagccc cgagaaccac aggtgtacac cctgccccca   1980

tcccgggatg agctgaccaa gaaccaggtc agcctgacct gcctggtcaa aggcttctat   2040

cccagcgaca tcgccgtgga gtgggagagc aatgggcagc cggagaacaa ctacaagacc   2100

acgcctcccg tgctggactc cgacggctcc ttcttcctct acagcaagct caccgtggac   2160

aagagcaggt ggcagcaggg gaacgtcttc tcatgctccg tgatgcatga ggctctgcac   2220

aaccactaca cgcagaagag cctctccctg tctccgggta aatga                    2265
```

<210> SEQ ID NO 30
<211> LENGTH: 2505
<212> TYPE: DNA
<213> ORGANISM: Artificial
<220> FEATURE:
<223> OTHER INFORMATION: Nucleotide sequence of fused protein

<400> SEQUENCE: 30

```
tcaaaattaa aagatcctga actgagttta aaaggcaccc agcacatcat gcaagcaggc     60

cagacactgc atctccaatg caggggggaa gcagcccata aatggtcttt gcctgaaatg    120

gtgagtaagg aaagcgaaag gctgagcata actaaatctg cctgtggaag aaatggcaaa    180

caattctgca gtactttaac cttgaacaca gctcaagcaa accacactgg cttctacagc    240

tgcaaatatc tagctgtacc tacttcaaag aagaaggaaa cagaatctgc aatctatata    300

tttattagtg atacaggtag acctttcgta gagatgtaca gtgaaatccc cgaaattata    360

cacatgactg aaggaaggga gctcgtcatt ccctgccggg ttacgtcacc taacatcact    420

gttactttaa aaaagtttcc acttgacact ttgatccctg atggaaaacg cataatctgg    480

gacagtagaa agggcttcat catatcaaat gcaacgtaca aagaaatagg gcttctgacc    540

tgtgaagcaa cagtcaatgg gcatttgtat aagacaaact atctcacaca tcgacaaacc    600

aatacaatca tagatgtggt tctgagtccg tctcatggaa ttgaactatc tgttggagaa    660

aagcttgtct taaattgtac agcaagaact gaactaaatg tggggattga cttcaactgg    720

gaataccctt cttcgaagca tcagcataag aaacttgtaa accgagacct aaaaacccag    780

tctgggagtg agatgaagaa atttttgagc accttaacta tagatggtgt aacccggagt    840

gaccaaggat tgtacacctg tgcagcatcc agtgggctga tgaccaagaa gaacagcaca    900

tttgtcaggg tccatgaaaa acctaaaaat cgcacccgca tcacagggga ggaggtggag    960

gtgcaggact ccgtgcccgc agactccggc ctctatgctt gcgtaaccag cagcccctcg   1020

ggcagtgaca ccacctactt ctccgtcaat gtttcagatg ctctcccctc ctcggaggat   1080

gatgatgatg atgatgactc ctcttcagag gagaaagaaa cagataacac caaaccaaac   1140

cccgtagctc catattggac atccccagaa aagatggaaa agaaattgca tgcagtgccg   1200

gctgccaaga cagtgaagtt caaatgccct tccagtggga ccccaaaccc cacactgcgc   1260

tggttgaaaa atggcaaaga attcaaacct gaccacagaa ttggaggcta caaggtccgt   1320

tatgccacct ggagcatcat aatggactct gtggtgccct ctgacaaggg caactacacc   1380

tgcattgtgg agaatgagta cggcagcatc aaccacacat accagctgga tgtcgtggag   1440

cggtcccctc accggcccat cctgcaagca gggttgcccg ccaacaaaac agtggccctg   1500

ggtagcaacg tggagttcat gtgtaaggtg tacagtgacc cgcagccgca catccagtgg   1560

ctaaagcaca tcgaggtgaa tgggagcaag attggcccag acaacctgcc ttatgtccag   1620

atcttgaaga ctgctggagt taataccacc gacaaagaga tggaggtgct tcacttaaga   1680
```

```
aatgtctcct ttgaggacgc aggggagtat acgtgcttgg cgggtaactc tatcggactc   1740

tcccatcact ctgcatggtt gaccgttctg gaagccctgg aagagaggcc ggcagtgatg   1800

acctcgcccc tgtacctgga ggacaaaact cacacatgcc caccgtgccc agcacctgaa   1860

ctcctggggg gaccgtcagt cttcctcttc cccccaaaac ccaaggacac cctcatgatc   1920

tcccggaccc ctgaggtcac atgcgtggtg gtggacgtga gccacgaaga ccctgaggtc   1980

aagttcaact ggtacgtgga cggcgtggag gtgcataatg ccaagacaaa gccgcgggag   2040

gagcagtaca acagcacgta ccgtgtggtc agcgtcctca ccgtcctgca ccaggactgg   2100

ctgaatggca aggagtacaa gtgcaaggtc tccaacaaag ccctcccagc ccccatcgag   2160

aaaaccatct ccaaagccaa agggcagccc cgagaaccac aggtgtacac cctgccccca   2220

tcccgggatg agctgaccaa gaaccaggtc agcctgacct gcctggtcaa aggcttctat   2280

cccagcgaca tcgccgtgga gtgggagagc aatgggcagc cggagaacaa ctacaagacc   2340

acgcctcccg tgctggactc cgacggctcc ttcttcctct acagcaagct caccgtggac   2400

aagagcaggt ggcagcaggg gaacgtcttc tcatgctccg tgatgcatga ggctctgcac   2460

aaccactaca cgcagaagag cctctccctg tctccgggta aatga                   2505
```

<210> SEQ ID NO 31
<211> LENGTH: 2265
<212> TYPE: DNA
<213> ORGANISM: Artificial
<220> FEATURE:
<223> OTHER INFORMATION: Nucleotide sequence of fused protein

<400> SEQUENCE: 31

```
ccagaaaaga tggaaaagaa attgcatgca gtgccggctg ccaagacagt gaagttcaaa     60

tgcccttcca gtgggacccc aaaccccaca ctgcgctggt tgaaaaatgg caaagaattc    120

aaacctgacc acagaattgg aggctacaag gtccgttatg ccacctggag catcataatg    180

gactctgtgg tgccctctga caagggcaac tacacctgca ttgtggagaa tgagtacggc    240

agcatcaacc acacatacca gctggatgtc gtggagcggt cccctcaccg gcccatcctg    300

caagcagggt tgcccgccaa caaaacagtg gccctgggta gcaacgtgga gttcatgtgt    360

aaggtgtaca gtgacccgca gccgcacatc cagtggctaa agcacatcga ggtgaatggg    420

agcaagattg gcccagacaa cctgccttat gtccagatct tgaagactgc tggagttaat    480

accaccgaca aagagatgga ggtgcttcac ttaagaaatg tctcctttga ggacgcaggg    540

gagtatacgt gcttggcggg taactctatc ggactctccc atcactctgc atggttgacc    600

gttctggaag ccctggaaga gaggccggca gtgatgacct cgcccctgta cctggagtca    660

aaattaaaag atcctgaact gagtttaaaa ggcacccagc acatcatgca agcaggccag    720

acactgcatc tccaatgcag gggggaagca gcccataaat ggtctttgcc tgaaatggtg    780

agtaaggaaa gcgaaaggct gagcataact aaatctgcct gtggaagaaa tggcaaacaa    840

ttctgcagta ctttaacctt gaacacagct caagcaaacc acactggctt ctacagctgc    900

aaatatctag ctgtacctac ttcaaagaag aaggaaacag aatctgcaat ctatatattt    960

attagtgata caggtagacc tttcgtagag atgtacagtg aaatccccga aattatacac   1020

atgactgaag gaagggagct cgtcattccc tgccgggtta cgtcacctaa catcactgtt   1080

actttaaaaa agtttccact tgacactttg atccctgatg gaaaacgcat aatctgggac   1140

agtagaaagg gcttcatcat atcaaatgca acgtacaaag aaatagggct tctgacctgt   1200
```

```
gaagcaacag tcaatgggca tttgtataag acaaactatc tcacacatcg acaaaccaat   1260
acaatcatag atgtggttct gagtccgtct catggaattg aactatctgt tggagaaaag   1320
cttgtcttaa attgtacagc aagaactgaa ctaaatgtgg ggattgactt caactgggaa   1380
tacccttctt cgaagcatca gcataagaaa cttgtaaacc gagacctaaa aacccagtct   1440
gggagtgaga tgaagaaatt tttgagcacc ttaactatag atggtgtaac ccggagtgac   1500
caaggattgt acacctgtgc agcatccagt gggctgatga ccaagaagaa cagcacattt   1560
gtcagggtcc atgaaaaacc tgacaaaact cacacatgcc caccgtgccc agcacctgaa   1620
ctcctggggg gaccgtcagt cttcctcttc cccccaaaac ccaaggacac cctcatgatc   1680
tcccggaccc ctgaggtcac atgcgtggtg gtggacgtga gccacgaaga ccctgaggtc   1740
aagttcaact ggtacgtgga cggcgtggag gtgcataatg ccaagacaaa gccgcgggag   1800
gagcagtaca acagcacgta ccgtgtggtc agcgtcctca ccgtcctgca ccaggactgg   1860
ctgaatggca aggagtacaa gtgcaaggtc tccaacaaag ccctcccagc ccccatcgag   1920
aaaaccatct ccaaagccaa agggcagccc cgagaaccac aggtgtacac cctgccccca   1980
tcccgggatg agctgaccaa gaaccaggtc agcctgacct gcctggtcaa aggcttctat   2040
cccagcgaca tcgccgtgga gtgggagagc aatgggcagc cggagaacaa ctacaagacc   2100
acgcctcccg tgctggactc cgacggctcc ttcttcctct acagcaagct caccgtggac   2160
aagagcaggt ggcagcaggg gaacgtcttc tcatgctccg tgatgcatga ggctctgcac   2220
aaccactaca cgcagaagag cctctccctg tctccgggta aatga                   2265
```

<210> SEQ ID NO 32
<211> LENGTH: 1608
<212> TYPE: DNA
<213> ORGANISM: Artificial
<220> FEATURE:
<223> OTHER INFORMATION: Nucleotide sequence of fused protein

<400> SEQUENCE: 32

```
tcaaaattaa aagatcctga actgagttta aaaggcaccc agcacatcat gcaagcaggc     60
cagacactgc atctccaatg caggggggaa gcagcccata aatggtcttt gcctgaaatg    120
gtgagtaagg aaagcgaaag gctgagcata actaaatctg cctgtggaag aaatggcaaa    180
caattctgta gtactttaac cttgaacaca gctcaagcaa accacactgg cttctacagc    240
tgcaaatatc tagctgtacc tacttcaaag aagaaggaaa cagaatctgc aatctatata    300
tttattagtg atacaggtag acctttcgta gagatgtaca gtgaaatccc cgaaattata    360
cacatgactg aaggaaggga gctcgtcatt ccctgccggg ttacgtcacc taacatcact    420
gttactttaa aaaagtttcc acttgacact ttgatccctg atggaaaacg cataatctgg    480
gacagtagaa agggcttcat catatcaaat gcaacgtaca aagaaatagg gcttctgacc    540
tgtgaagcaa cagtcaatgg gcatttgtat aagacaaact atctcacaca tcgacaaacc    600
aatacaatca tagatgtggt tctgagtccg tctcatggaa ttgaactatc tgttggagaa    660
aagcttgtct taaattgtac agcaagaact gaactaaatg tggggattga cttcaactgg    720
gaataccctt cttcgaagca tcagcataag aaacttgtaa accgagacct aaaaacccag    780
tctgggagtg agatgaagaa atttttgagc accttaacta tagatggtgt aacccggagt    840
gaccaaggat tgtacacctg tgcagcatcc agtgggctga tgaccaagaa gaacagcaca    900
tttgtcaggg tccatgaaaa acctgacaaa actcacacat gcccaccgtg cccagcacct    960
gaactcctgg ggggaccgtc agtcttcctc ttccccccaa aacccaagga caccctcatg   1020
```

```
atctcccgga cccctgaggt cacatgcgtg gtggtggacg tgagccacga agaccctgag   1080
gtcaagttca actggtacgt ggacggcgtg gaggtgcata atgccaagac aaagccgcgg   1140
gaggagcagt acaacagcac gtaccgtgtg gtcagcgtcc tcaccgtcct gcaccaggac   1200
tggctgaatg gcaaggagta caagtgcaag gtctccaaca aagccctccc agcccccatc   1260
gagaaaacca tctccaaagc caaagggcag ccccgagaac cacaggtgta caccctgccc   1320
ccatcccggg atgagctgac caagaaccag gtcagcctga cctgcctggt caaaggcttc   1380
tatcccagcg acatcgccgt ggagtgggag agcaatgggc agccggagaa caactacaag   1440
accacgcctc ccgtgctgga ctccgacggc tccttcttcc tctacagcaa gctcaccgtg   1500
gacaagagca ggtggcagca ggggaacgtc ttctcatgct ccgtgatgca tgaggctctg   1560
cacaaccact acacgcagaa gagcctctcc ctgtctccgg gtaaatga                1608
```

<210> SEQ ID NO 33
<211> LENGTH: 2505
<212> TYPE: DNA
<213> ORGANISM: Artificial
<220> FEATURE:
<223> OTHER INFORMATION: Nucleotide sequence of fused protein

<400> SEQUENCE: 33

```
aaaaatcgca cccgcatcac aggggaggag gtggaggtgc aggactccgt gcccgcagac     60
tccggcctct atgcttgcgt aaccagcagc ccctcgggca gtgacaccac ctacttctcc    120
gtcaatgttt cagatgctct cccctcctcg gaggatgatg atgatgatga tgactcctct    180
tcagaggaga aagaaacaga taacaccaaa ccaaaccccg tagctccata ttggacatcc    240
ccagaaaaga tggaaaagaa attgcatgca gtgccggctg ccaagacagt gaagttcaaa    300
tgcccttcca gtgggacccc aaaccccaca ctgcgctggt tgaaaaatgg caaagaattc    360
aaacctgacc acagaattgg aggctacaag gtccgttatg ccacctggag catcataatg    420
gactctgtgg tgccctctga caagggcaac tacacctgca ttgtggagaa tgagtacggc    480
agcatcaacc acacatacca gctggatgtc gtggagcggt cccctcaccg gcccatcctg    540
caagcagggt tgcccgccaa caaaacagtg gccctgggta gcaacgtgga gttcatgtgt    600
aaggtgtaca gtgacccgca gccgcacatc cagtggctaa agcacatcga ggtgaatggg    660
agcaagattg gcccagacaa cctgccttat gtccagatct tgaagactgc tggagttaat    720
accaccgaca aagagatgga ggtgcttcac ttaagaaatg tctcctttga ggacgcaggg    780
gagtatacgt gcttggcggg taactctatc ggactctccc atcactctgc atggttgacc    840
gttctggaag ccctggaaga gaggccggca gtgatgacct cgcccctgta cctggagtca    900
aaattaaaag atcctgaact gagtttaaaa ggcacccagc acatcatgca agcaggccag    960
acactgcatc tccaatgcag gggggaagca gcccataaat ggtctttgcc tgaaatggtg   1020
agtaaggaaa gcgaaaggct gagcataact aaatctgcct gtggaagaaa tggcaaacaa   1080
ttctgcagta ctttaacctt gaacacagct caagcaaacc acactggctt ctacagctgc   1140
aaatatctag ctgtacctac ttcaaagaag aaggaaacag aatctgcaat ctatatattt   1200
attagtgata caggtagacc tttcgtagag atgtacagtg aaatccccga aattatacac   1260
atgactgaag gaagggagct cgtcattccc tgccgggtta cgtcacctaa catcactgtt   1320
actttaaaaa agtttccact tgacactttg atccctgatg gaaaacgcat aatctgggac   1380
agtagaaagg gcttcatcat atcaaatgca acgtacaaag aaatagggct tctgacctgt   1440
```

-continued

```
gaagcaacag tcaatgggca tttgtataag acaaactatc tcacacatcg acaaaccaat   1500
acaatcatag atgtggttct gagtccgtct catggaattg aactatctgt tggagaaaag   1560
cttgtcttaa attgtacagc aagaactgaa ctaaatgtgg ggattgactt caactgggaa   1620
tacccttctt cgaagcatca gcataagaaa cttgtaaacc gagacctaaa aacccagtct   1680
gggagtgaga tgaagaaatt tttgagcacc ttaactatag atggtgtaac ccggagtgac   1740
caaggattgt acacctgtgc agcatccagt gggctgatga ccaagaagaa cagcacattt   1800
gtcagggtcc atgaaaaacc tgacaaaact cacacatgcc caccgtgccc agcacctgaa   1860
ctcctggggg gaccgtcagt cttcctcttc cccccaaaac ccaaggacac cctcatgatc   1920
tcccggaccc ctgaggtcac atgcgtggtg gtggacgtga gccacgaaga ccctgaggtc   1980
aagttcaact ggtacgtgga cggcgtggag gtgcataatg ccaagacaaa gccgcgggag   2040
gagcagtaca acagcacgta ccgtgtggtc agcgtcctca ccgtcctgca ccaggactgg   2100
ctgaatggca aggagtacaa gtgcaaggtc tccaacaaag ccctcccagc ccccatcgag   2160
aaaaccatct ccaaagccaa agggcagccc cgagaaccac aggtgtacac cctgccccca   2220
tcccgggatg agctgaccaa gaaccaggtc agcctgacct gcctggtcaa aggcttctat   2280
cccagcgaca tcgccgtgga gtgggagagc aatgggcagc cggagaacaa ctacaagacc   2340
acgcctcccg tgctggactc cgacggctcc ttcttcctct acagcaagct caccgtggac   2400
aagagcaggt ggcagcaggg gaacgtcttc tcatgctccg tgatgcatga ggctctgcac   2460
aaccactaca cgcagaagag cctctccctg tctccgggta aatga                     2505
```

```
<210> SEQ ID NO 34
<211> LENGTH: 1293
<212> TYPE: DNA
<213> ORGANISM: Artificial
<220> FEATURE:
<223> OTHER INFORMATION: Nucleotide sequence of fused protein

<400> SEQUENCE: 34
```

```
ggtagacctt tcgtagagat gtacagtgaa atccccgaaa ttatacacat gactgaagga     60
agggagctcg tcattccctg ccgggttacg tcacctaaca tcactgttac tttaaaaaag    120
tttccacttg acactttgat ccctgatgga aaacgcataa tctgggacag tagaaagggc    180
ttcatcatat caaatgcaac gtacaaagaa atagggcttc tgacctgtga agcaacagtc    240
aatgggcatt tgtataagac aaactatctc acacatcgac aaaccaatac aatcatagat    300
gtggttctga gtccgtctca tggaattgaa ctatctgttg gagaaaagct tgtcttaaat    360
tgtacagcaa gaactgaact aaatgtgggg attgacttca actgggaata cccttcttcg    420
aagcatcagc ataagaaact tgtaaaccga gacctaaaaa cccagtctgg gagtgagatg    480
aagaaatttt tgagcacctt aactatagat ggtgtaaccc ggagtgacca aggattgtac    540
acctgtgcag catccagtgg gctgatgacc aagaagaaca gcacatttgt cagggtccat    600
gaaaaacctg acaaaactca cacatgccca ccgtgcccag cacctgaact cctgggggga    660
ccgtcagtct tcctcttccc cccaaaaccc aaggacaccc tcatgatctc ccggacccct    720
gaggtcacat gcgtggtggt ggacgtgagc cacgaagacc ctgaggtcaa gttcaactgg    780
tacgtggacg gcgtggaggt gcataatgcc aagacaaagc cgcgggagga gcagtacaac    840
agcacgtacc gtgtggtcag cgtcctcacc gtcctgcacc aggactggct gaatggcaag    900
gagtacaagt gcaaggtctc caacaaagcc ctcccagccc ccatcgagaa aaccatctcc    960
aaagccaaag ggcagccccg agaaccacag gtgtacaccc tgcccccatc ccgggatgag   1020
```

-continued

```
ctgaccaaga accaggtcag cctgacctgc ctggtcaaag gcttctatcc cagcgacatc   1080

gccgtggagt gggagagcaa tgggcagccg gagaacaact acaagaccac gcctcccgtg   1140

ctggactccg acggctcctt cttcctctac agcaagctca ccgtggacaa gagcaggtgg   1200

cagcagggga acgtcttctc atgctccgtg atgcatgagg ctctgcacaa ccactacacg   1260

cagaagagcc tctccctgtc tccgggtaaa tga                                1293
```

<210> SEQ ID NO 35
<211> LENGTH: 2667
<212> TYPE: DNA
<213> ORGANISM: Artificial
<220> FEATURE:
<223> OTHER INFORMATION: Nucleotide sequence of fused protein

<400> SEQUENCE: 35

```
tcaaaattaa aagatcctga actgagttta aaaggcaccc agcacatcat gcaagcaggc     60

cagacactgc atctccaatg caggggggaa gcagcccata aatggtcttt gcctgaaatg    120

gtgagtaagg aaagcgaaag gctgagcata actaaatctg cctgtggaag aaatggcaaa    180

caattctgca gtactttaac cttgaacaca gctcaagcaa accacactgg cttctacagc    240

tgcaaatatc tagctgtacc tacttcaaag aagaaggaaa cagaatctgc aatctatata    300

tttattagtg atacaggtag acctttcgta gagatgtaca gtgaaatccc cgaaattata    360

cacatgactg aaggaaggga gctcgtcatt ccctgccggg ttacgtcacc taacatcact    420

gttactttaa aaaagtttcc acttgacact ttgatccctg atggaaaacg cataatctgg    480

gacagtagaa agggcttcat catatcaaat gcaacgtaca aagaaatagg gcttctgacc    540

tgtgaagcaa cagtcaatgg gcatttgtat aagacaaact atctcacaca tcgacaaacc    600

aatacaatca tagatgtggt tctgagtccg tctcatggaa ttgaactatc tgttggagaa    660

aagcttgtct taaattgtac agcaagaact gaactaaatg tggggattga cttcaactgg    720

gaataccctt cttcgaagca tcagcataag aaacttgtaa accgagacct aaaaacccag    780

tctgggagtg agatgaagaa atttttgagc accttaacta tagatggtgt aacccggagt    840

gaccaaggat tgtacacctg tgcagcatcc agtgggctga tgaccaagaa gaacagcaca    900

tttgtcaggg tccatgaaaa acctaggccg tccccgacct tgcctgaaca agcccagccc    960

tggggagccc ctgtggaagt ggagtccttc ctggtccacc ccggtgacct gctgcagctt   1020

cgctgtcggc tgcgggacga tgtgcagagc atcaactggc tgcgggacgg ggtgcagctg   1080

gcggaaagca accgcacccg catcacaggg gaggaggtgg aggtgcagga ctccgtgccc   1140

gcagactccg gcctctatgc ttgcgtaacc agcagcccct cgggcagtga caccacctac   1200

ttctccgtca atgtttcaga tgctctcccc tcctcggagg atgatgatga tgatgatgac   1260

tcctcttcag aggagaaaga aacagataac accaaaccaa accccgtagc tccatattgg   1320

acatccccag aaaagatgga aaagaaattg catgcagtgc cggctgccaa gacagtgaag   1380

ttcaaatgcc cttccagtgg gaccccaaac cccacactgc gctggttgaa aaatggcaaa   1440

gaattcaaac ctgaccacag aattggaggc tacaaggtcc gttatgccac ctggagcatc   1500

ataatggact ctgtggtgcc ctctgacaag ggcaactaca cctgcattgt ggagaatgag   1560

tacggcagca tcaaccacac ataccagctg gatgtcgtgg agcggtcccc tcaccggccc   1620

atcctgcaag cagggttgcc cgccaacaaa acagtggccc tgggtagcaa cgtggagttc   1680

atgtgtaagg tgtacagtga cccgcagccg cacatccagt ggctaaagca catcgaggtg   1740
```

-continued

```
aatgggagca agattggccc agacaacctg ccttatgtcc agatcttgaa gactgctgga   1800

gttaatacca ccgacaaaga gatggaggtg cttcacttaa gaaatgtctc ctttgaggac   1860

gcaggggagt atacgtgctt ggcgggtaac tctatcggac tctcccatca ctctgcatgg   1920

ttgaccgttc tggaagccct ggaagagagg ccggcagtga tgacctcgcc cctgtacctg   1980

gaggacaaaa ctcacacatg cccaccgtgc ccagcacctg aactcctggg gggaccgtca   2040

gtcttcctct tccccccaaa acccaaggac accctcatga tctcccggac ccctgaggtc   2100

acatgcgtgg tggtggacgt gagccacgaa gaccctgagg tcaagttcaa ctggtacgtg   2160

gacggcgtgg aggtgcataa tgccaagaca aagccgcggg aggagcagta caacagcacg   2220

taccgtgtgg tcagcgtcct caccgtcctg caccaggact ggctgaatgg caaggagtac   2280

aagtgcaagg tctccaacaa agccctccca gcccccatcg agaaaaccat ctccaaagcc   2340

aaagggcagc cccgagaacc acaggtgtac accctgcccc catcccggga tgagctgacc   2400

aagaaccagg tcagcctgac ctgcctggtc aaaggcttct atcccagcga catcgccgtg   2460

gagtgggaga gcaatgggca gccggagaac aactacaaga ccacgcctcc cgtgctggac   2520

tccgacggct ccttcttcct ctacagcaag ctcaccgtgg acaagagcag gtggcagcag   2580

gggaacgtct tctcatgctc cgtgatgcat gaggctctgc acaaccacta cacgcagaag   2640

agcctctccc tgtctccggg taaatga                                       2667
```

```
<210> SEQ ID NO 36
<211> LENGTH: 2502
<212> TYPE: DNA
<213> ORGANISM: Artificial
<220> FEATURE:
<223> OTHER INFORMATION: Nucleotide sequence of fused protein

<400> SEQUENCE: 36

tcaaaattaa aagatcctga actgagttta aaaggcaccc agcacatcat gcaagcaggc     60

cagacactgc atctccaatg caggggggaa gcagcccata aatggtcttt gcctgaaatg    120

gtgagtaagg aaagcgaaag gctgagcata actaaatctg cctgtggaag aaatggcaaa    180

caattctgca gtactttaac cttgaacaca gctcaagcaa accacactgg cttctacagc    240

tgcaaatatc tagctgtacc tacttcaaag aagaaggaaa cagaatctgc aatctatata    300

tttattagtg atacaggtag acctttcgta gagatgtaca gtgaaatccc cgaaattata    360

cacatgactg aaggaaggga gctcgtcatt ccctgccggg ttacgtcacc taacatcact    420

gttactttaa aaaagtttcc acttgacact ttgatccctg atggaaaacg cataatctgg    480

gacagtagaa agggcttcat catatcaaat gcaacgtaca aagaaatagg gcttctgacc    540

tgtgaagcaa cagtcaatgg gcatttgtat aagacaaact atctcacaca tcgacaaacc    600

aatacaatca tagatgtggt tctgagtccg tctcatggaa ttgaactatc tgttggagaa    660

aagcttgtct taaattgtac agcaagaact gaactaaatg tggggattga cttcaactgg    720

gaatacccct cttcgaagca tcagcataag aaacttgtaa accgagacct aaaaacccag    780

tctgggagtg agatgaagaa atttttgagc accttaacta tagatggtgt aacccggagt    840

gaccaaggat tgtacacctg tgcagcatcc agtgggctga tgaccaagaa gaacagcaca    900

tttgtcaggg tccatgaaaa acctaatcgc acccgcatca caggggagga ggtggaggtg    960

caggactccg tgcccgcaga ctccggcctc tatgcttgcg taaccagcag cccctcgggc   1020

agtgacacca cctacttctc cgtcaatgtt tcagatgctc tcccctcctc ggaggatgat   1080

gatgatgatg atgactcctc ttcagaggag aaagaaacag ataacaccaa accaaacccc   1140
```

```
gtagctccat attggacatc cccagaaaag atggaaaaga aattgcatgc agtgccggct   1200
gccaagacag tgaagttcaa atgcccttcc agtgggaccc caaaccccac actgcgctgg   1260
ttgaaaaatg gcaaagaatt caaacctgac cacagaattg gaggctacaa ggtccgttat   1320
gccacctgga gcatcataat ggactctgtg gtgccctctg acaagggcaa ctacacctgc   1380
attgtggaga atgagtacgg cagcatcaac cacacatacc agctggatgt cgtggagcgg   1440
tcccctcacc ggcccatcct gcaagcaggg ttgcccgcca acaaaacagt ggccctgggt   1500
agcaacgtgg agttcatgtg taaggtgtac agtgacccgc agccgcacat ccagtggcta   1560
aagcacatcg aggtgaatgg gagcaagatt ggcccagaca acctgcctta tgtccagatc   1620
ttgaagactg ctggagttaa taccaccgac aaagagatgg aggtgcttca cttaagaaat   1680
gtctcctttg aggacgcagg ggagtatacg tgcttggcgg gtaactctat cggactctcc   1740
catcactctg catggttgac cgttctggaa gccctggaag agaggccggc agtgatgacc   1800
tcgcccctgt acctggagga caaaactcac acatgcccac cgtgcccagc acctgaactc   1860
ctggggggac cgtcagtctt cctcttcccc ccaaaaccca aggacaccct catgatctcc   1920
cggacccctg aggtcacatg cgtggtggtg gacgtgagcc acgaagaccc tgaggtcaag   1980
ttcaactggt acgtggacgg cgtggaggtg cataatgcca agacaaagcc gcgggaggag   2040
cagtacaaca gcacgtaccg tgtggtcagc gtcctcaccg tcctgcacca ggactggctg   2100
aatggcaagg agtacaagtg caaggtctcc aacaaagccc tcccagcccc catcgagaaa   2160
accatctcca aagccaaagg gcagccccga gaaccacagg tgtacaccct gcccccatcc   2220
cgggatgagc tgaccaagaa ccaggtcagc ctgacctgcc tggtcaaagg cttctatccc   2280
agcgacatcg ccgtggagtg ggagagcaat gggcagccgg agaacaacta caagaccacg   2340
cctcccgtgc tggactccga cggctccttc ttcctctaca gcaagctcac cgtggacaag   2400
agcaggtggc agcaggggaa cgtcttctca tgctccgtga tgcatgaggc tctgcacaac   2460
cactacacgc agaagagcct ctccctgtct ccgggtaaat ga                       2502
```

<210> SEQ ID NO 37
<211> LENGTH: 2505
<212> TYPE: DNA
<213> ORGANISM: Artificial
<220> FEATURE:
<223> OTHER INFORMATION: Nucleotide sequence of fused protein

<400> SEQUENCE: 37

```
agcaaattaa aagatcctga actgagttta aaaggcaccc agcacatcat gcaagcaggc     60
cagacactgc atctccaatg caggggggaa gcagcccata aatggtcttt gcctgaaatg    120
gtgagtaagg aaagcgaaag gctgagcata actaaatctg cctgtggaag aaatggcaaa    180
caattctgta gtactttaac cttgaacaca gctcaagcaa accacactgg cttctacagc    240
tgcaaatatc tagctgtacc tacttcaaag aagaaggaaa cagaatctgc aatctatata    300
tttattagtg atacaggtag acctttcgta gagatgtaca gtgaaatccc cgaaattata    360
cacatgactg aaggaaggga gctcgtcatt ccctgccggg ttacgtcacc taacatcact    420
gttactttaa aaaagtttcc acttgacact ttgatccctg atggaaaacg cataatctgg    480
gacagtagaa agggcttcat catatcaaat gcaacgtaca aagaaatagg gcttctgacc    540
tgtgaagcaa cagtcaatgg gcatttgtat aagacaaact atctcacaca tcgacaaacc    600
aatacaatca tagatgtggt tctgagtccg tctcatggaa ttgaactatc tgttggagaa    660
```

```
aagcttgtct taaattgtac agcaagaact gaactaaatg tggggattga cttcaactgg    720

gaataccctt cttcgaagca tcagcataag aaacttgtaa accgagacct aaaaacccag    780

tctgggagtg agatgaagaa atttttgagc accttaacta tagatggtgt aacccggagt    840

gaccaaggat tgtacacctg tgcagcatcc agtgggctga tgaccaagaa gaacagcaca    900

tttgtcaggg tccatgaaaa acctaaaaat cgcacccgca tcacagggga ggaggtggag    960

gtgcaggact ccgtgcccgc agactccggc ctctatgctt ccgtaaccag cagcccctcg   1020

ggcagtgaca ccacctactt ctccgtcaat gtttcagatg ctctcccctc ctcggaggat   1080

gatgatgatg atgatgactc ctcttcagag gagaaagaaa cagataacac caaaccaaac   1140

cccgtagctc catattggac atccccagaa aagatggaaa agaaattgca tgcagtgccg   1200

gctgccaaga cagtgaagtt caaatgccct tccagtggga ccccaaaccc cacactgcgc   1260

tggttgaaaa atggcaaaga attcaaacct gaccacagaa ttggaggcta caaggtccgt   1320

tatgccacct ggagcatcat aatggactct gtggtgccct ctgacaaggg caactacacc   1380

tgcattgtgg agaatgagta cggcagcatc aaccacacat accagctgga tgtcgtggag   1440

cggtcccctc accggcccat cctgcaagca gggttgcccg ccaacaaaac agtggccctg   1500

ggtagcaacg tggagttcat gtgtaaggtg tacagtgacc cgcagccgca catccagtgg   1560

ctaaagcaca tcgaggtgaa tgggagcaag attggcccag acaacctgcc ttatgtccag   1620

atcttgaaga ctgctggagt taataccacc gacaaagaga tggaggtgct tcacttaaga   1680

aatgtctcct ttgaggacgc aggggagtat acgtgcttgg cgggtaactc tatcggactc   1740

tcccatcact ctgcatggtt gaccgttctg gaagccctgg aagagaggcc ggcagtgatg   1800

acctcgcccc tgtacctgga ggacaaaact cacacatgcc caccgtgccc agcacctgaa   1860

ctcctggggg gaccgtcagt cttcctcttc cccccaaaac ccaaggacac cctcatgatc   1920

tcccggaccc ctgaggtcac atgcgtggtg gtggacgtga gccacgaaga ccctgaggtc   1980

aagttcaact ggtacgtgga cggcgtggag gtgcataatg ccaagacaaa gccgcgggag   2040

gagcagtaca acagcacgta ccgtgtggtc agcgtcctca ccgtcctgca ccaggactgg   2100

ctgaatggca aggagtacaa gtgcaaggtc tccaacaaag ccctcccagc ccccatcgag   2160

aaaaccatct ccaaagccaa agggcagccc cgagaaccac aggtgtacac cctgccccca   2220

tcccgggatg agctgaccaa gaaccaggtc agcctgacct gcctggtcaa aggcttctat   2280

cccagcgaca tcgccgtgga gtgggagagc aatgggcagc cggagaacaa ctacaagacc   2340

acgcctcccg tgctggactc cgacggctcc ttcttcctct acagcaagct caccgtggac   2400

aagagcaggt ggcagcaggg gaacgtcttc tcatgctccg tgatgcatga ggctctgcac   2460

aaccactaca cgcagaagag cctctccctg tctccgggta aatga                   2505
```

<210> SEQ ID NO 38
<211> LENGTH: 2412
<212> TYPE: DNA
<213> ORGANISM: Artificial
<220> FEATURE:
<223> OTHER INFORMATION: Nucleotide sequence of fused protein

<400> SEQUENCE: 38

```
agcaaattaa aagatcctga actgagttta aaaggcaccc agcacatcat gcaagcaggc     60

cagacactgc atctccaatg caggggggaa gcagcccata aatggtcttt gcctgaaatg    120

gtgagtaagg aaagcgaaag gctgagcata actaaatctg cctgtggaag aaatggcaaa    180

caattctgca gtactttaac cttgaacaca gctcaagcaa accacactgg cttctacagc    240
```

-continued

```
tgcaaatatc tagctgtacc tacttcaaag aagaaggaaa cagaatctgc aatctatata    300
tttattagtg atacaggtag acctttcgta gagatgtaca gtgaaatccc cgaaattata    360
cacatgactg aaggaaggga gctcgtcatt ccctgccggg ttacgtcacc taacatcact    420
gttactttaa aaaagtttcc acttgacact ttgatccctg atggaaaacg cataatctgg    480
gacagtagaa agggcttcat catatcaaat gcaacgtaca aagaaatagg gcttctgacc    540
tgtgaagcaa cagtcaatgg gcatttgtat aagacaaact atctcacaca tcgacaaacc    600
aatacaatca tagatgtggt tctgagtccg tctcatggaa ttgaactatc tgttggagaa    660
aagcttgtct taaattgtac agcaagaact gaactaaatg tggggattga cttcaactgg    720
gaatacccctt cttcgaagca tcagcataag aaacttgtaa accgagacct aaaaacccag    780
tctgggagtg agatgaagaa atttttgagc accttaacta tagatggtgt aacccggagt    840
gaccaaggat tgtacacctg tgcagcatcc agtgggctga tgaccaagaa gaacagcaca    900
tttgtcaggg tccatgaaaa accttcgggc agtgacacca cctacttctc cgtcaatgtt    960
tcagatgctc tcccctcctc ggaggatgat gatgatgatg atgactcctc ttcagaggag   1020
aaagaaacag ataacaccaa accaaacccc gtagctccat attggacatc ccagaaaaag   1080
atggaaaaga aattgcatgc agtgccggct gccaagacag tgaagttcaa atgcccttcc   1140
agtgggaccc caaaccccac actgcgctgg ttgaaaaatg gcaaagaatt caaacctgac   1200
cacagaattg gaggctacaa ggtccgttat gccacctgga gcatcataat ggactctgtg   1260
gtgccctctg acaagggcaa ctacacctgc attgtggaga atgagtacgg cagcatcaac   1320
cacacatacc agctggatgt cgtggagcgg tcccctcacc ggcccatcct gcaagcaggg   1380
ttgcccgcca acaaaacagt ggccctgggt agcaacgtgg agttcatgtg taaggtgtac   1440
agtgacccgc agccgcacat ccagtggcta aagcacatcg aggtgaatgg gagcaagatt   1500
ggcccagaca acctgcctta tgtccagatc ttgaagactg ctggagttaa taccaccgac   1560
aaagagatgg aggtgcttca cttaagaaat gtctcctttg aggacgcagg ggagtatacg   1620
tgcttggcgg gtaactctat cggactctcc catcactctg catggttgac cgttctggaa   1680
gccctggaag agaggccggc agtgatgacc tcgcccctgt acctggagga caaaactcac   1740
acatgcccac cgtgcccagc acctgaactc ctggggggac cgtcagtctt cctcttcccc   1800
ccaaaaccca aggacaccct catgatctcc cggacccctg aggtcacatg cgtggtggtg   1860
gacgtgagcc acgaagaccc tgaggtcaag ttcaactggt acgtggacgg cgtggaggtg   1920
cataatgcca agacaaagcc gcgggaggag cagtacaaca gcacgtaccg tgtggtcagc   1980
gtcctcaccg tcctgcacca ggactggctg aatggcaagg agtacaagtg caaggtctcc   2040
aacaaagccc tcccagcccc catcgagaaa accatctcca aagccaaagg gcagccccga   2100
gaaccacagg tgtacaccct gcccccatcc cgggatgagc tgaccaagaa ccaggtcagc   2160
ctgacctgcc tggtcaaagg cttctatccc agcgacatcg ccgtggagtg ggagagcaat   2220
gggcagccgg agaacaacta caagaccacg cctcccgtgc tggactccga cggctccttc   2280
ttcctctaca gcaagctcac cgtggacaag agcaggtggc agcaggggaa cgtcttctca   2340
tgctccgtga tgcatgaggc tctgcacaac cactacacgc agaagagcct ctccctgtct   2400
ccgggtaaat ga                                                       2412
```

<210> SEQ ID NO 39
<211> LENGTH: 2292
<212> TYPE: DNA

-continued

<213> ORGANISM: Artificial
<220> FEATURE:
<223> OTHER INFORMATION: Nucleotide sequence of fused protein

<400> SEQUENCE: 39

```
agcaaattaa aagatcctga actgagttta aaaggcaccc agcacatcat gcaagcaggc     60
cagacactgc atctccaatg caggggggaa gcagcccata aatggtcttt gcctgaaatg    120
gtgagtaagg aaagcgaaag gctgagcata actaaatctg cctgtggaag aaatggcaaa    180
caattctgca gtactttaac cttgaacaca gctcaagcaa accacactgg cttctacagc    240
tgcaaatatc tagctgtacc tacttcaaag aagaaggaaa cagaatctgc aatctatata    300
tttattagtg atacaggtag acctttcgta gagatgtaca gtgaaatccc cgaaattata    360
cacatgactg aaggaaggga gctcgtcatt ccctgccggg ttacgtcacc taacatcact    420
gttactttaa aaaagtttcc acttgacact ttgatccctg atggaaaacg cataatctgg    480
gacagtagaa agggcttcat catatcaaat gcaacgtaca aagaaatagg gcttctgacc    540
tgtgaagcaa cagtcaatgg gcatttgtat aagacaaact atctcacaca tcgacaaacc    600
aatacaatca tagatgtggt tctgagtccg tctcatggaa ttgaactatc tgttggagaa    660
aagcttgtct taaattgtac agcaagaact gaactaaatg tggggattga cttcaactgg    720
gaataccctt cttcgaagca tcagcataag aaacttgtaa accgagacct aaaaacccag    780
tctgggagtg agatgaagaa atttttgagc accttaacta tagatggtgt aacccggagt    840
gaccaaggat tgtacacctg tgcagcatcc agtgggctga tgaccaagaa gaacagcaca    900
tttgtcaggg tccatgaaaa acctaacccc gtagctccat attggacatc cccagaaaag    960
atggaaaaga aattgcatgc agtgccggct gccaagacag tgaagttcaa atgcccttcc   1020
agtgggaccc caaaccccac actgcgctgg ttgaaaaatg gcaaagaatt caaacctgac   1080
cacagaattg gaggctacaa ggtccgttat gccacctgga gcatcataat ggactctgtg   1140
gtgccctctg acaagggcaa ctacacctgc attgtggaga atgagtacgg cagcatcaac   1200
cacacatacc agctggatgt cgtggagcgg tcccctcacc ggcccatcct gcaagcaggg   1260
ttgcccgcca acaaaacagt ggccctgggt agcaacgtgg agttcatgtg taaggtgtac   1320
agtgacccgc agccgcacat ccagtggcta aagcacatcg aggtgaatgg gagcaagatt   1380
ggcccagaca acctgcctta tgtccagatc ttgaagactg ctggagttaa taccaccgac   1440
aaagagatgg aggtgcttca cttaagaaat gtctcctttg aggacgcagg ggagtatacg   1500
tgcttggcgg gtaactctat cggactctcc catcactctg catggttgac cgttctggaa   1560
gccctggaag agaggccggc agtgatgacc tcgcccctgt acctggagga caaaactcac   1620
acatgcccac cgtgcccagc acctgaactc ctggggggac cgtcagtctt cctcttcccc   1680
ccaaaaccca aggacaccct catgatctcc cggacccctg aggtcacatg cgtggtggtg   1740
gacgtgagcc acgaagaccc tgaggtcaag ttcaactggt acgtggacgg cgtggaggtg   1800
cataatgcca agacaaagcc gcgggaggag cagtacaaca gcacgtaccg tgtggtcagc   1860
gtcctcaccg tcctgcacca ggactggctg aatggcaagg agtacaagtg caaggtctcc   1920
aacaaagccc tcccagcccc catcgagaaa accatctcca aagccaaagg gcagccccga   1980
gaaccacagg tgtacaccct gcccccatcc cgggatgagc tgaccaagaa ccaggtcagc   2040
ctgacctgcc tggtcaaagg cttctatccc agcgacatcg ccgtggagtg ggagagcaat   2100
gggcagccgg agaacaacta caagaccacg cctcccgtgc tggactccga cggctccttc   2160
ttcctctaca gcaagctcac cgtggacaag agcaggtggc agcaggggaa cgtcttctca   2220
```

-continued tgctccgtga tgcatgaggc tctgcacaac cactacacgc agaagagcct ctccctgtct 2280
ccgggtaaat ga 2292

<210> SEQ ID NO 40
<211> LENGTH: 2298
<212> TYPE: DNA
<213> ORGANISM: Artificial
<220> FEATURE:
<223> OTHER INFORMATION: Nucleotide sequence of fused protein

<400> SEQUENCE: 40
aaacctaacc ccgtagctcc atattggaca tccccagaaa agatggaaaa gaaattgcat 60
gcagtgccgg ctgccaagac agtgaagttc aaatgccctt ccagtgggac cccaaacccc 120
acactgcgct ggttgaaaaa tggcaaagaa ttcaaacctg accacagaat tggaggctac 180
aaggtccgtt atgccacctg gagcatcata atggactctg tggtgccctc tgacaagggc 240
aactacacct gcattgtgga gaatgagtac ggcagcatca accacacata ccagctggat 300
gtcgtggagc ggtcccctca ccggcccatc ctgcaagcag ggttgcccgc caacaaaaca 360
gtggccctgg gtagcaacgt ggagttcatg tgtaaggtgt acagtgaccc gcagccgcac 420
atccagtggc taaagcacat cgaggtgaat gggagcaaga ttggcccaga caacctgcct 480
tatgtccaga tcttgaagac tgctggagtt aataccaccg acaaagagat ggaggtgctt 540
cacttaagaa atgtctcctt tgaggacgca ggggagtata cgtgcttggc gggtaactct 600
atcggactct cccatcactc tgcatggttg accgttctgg aagccctgga agagaggccg 660
gcagtgatga cctcgcccct gtacctggag tcaaaattaa aagatcctga actgagttta 720
aaaggcaccc agcacatcat gcaagcaggc cagacactgc atctccaatg cagggggga 780 gcagcccata aatggtcttt gcctgaaatg gtgagtaagg aaagcgaaag gctgagcata 840
actaaatctg cctgtggaag aaatggcaaa caattctgta gtactttaac cttgaacaca 900
gctcaagcaa accacactgg cttctacagc tgcaaatatc tagctgtacc tacttcaaag 960
aagaaggaaa cagaatctgc aatctatata tttattagtg atacaggtag acctttcgta 1020
gagatgtaca gtgaaatccc cgaaattata cacatgactg aaggaaggga gctcgtcatt 1080
ccctgccggg ttacgtcacc taacatcact gttactttaa aaaagtttcc acttgacact 1140
ttgatccctg atggaaaacg cataatctgg gacagtagaa agggcttcat catatcaaat 1200
gcaacgtaca aagaaatagg gcttctgacc tgtgaagcaa cagtcaatgg gcatttgtat 1260
aagacaaact atctcacaca tcgacaaacc aatacaatca tagatgtggt tctgagtccg 1320
tctcatggaa ttgaactatc tgttggagaa aagcttgtct taaattgtac agcaagaact 1380
gaactaaatg tggggattga cttcaactgg gaataccctt cttcgaagca tcagcataag 1440
aaacttgtaa accgagacct aaaaacccag tctgggagtg agatgaagaa atttttgagc 1500
accttaacta tagatggtgt aacccggagt gaccaaggat tgtacacctg tgcagcatcc 1560
agtgggctga tgaccaagaa gaacagcaca tttgtcaggg tccatgaaaa acctgacaaa 1620
actcacacat gcccaccgtg cccagcacct gaactcctgg ggggaccgtc agtcttcctc 1680
ttccccccaa aacccaagga caccctcatg atctcccgga cccctgaggt cacatgcgtg 1740
gtggtggacg tgagccacga agaccctgag gtcaagttca actggtacgt ggacggcgtg 1800
gaggtgcata atgccaagac aaagccgcgg gaggagcagt acaacagcac gtaccgtgtg 1860
gtcagcgtcc tcaccgtcct gcaccaggac tggctgaatg gcaaggagta caagtgcaag 1920

-continued

```
gtctccaaca aagccctccc agcccccatc gagaaaacca tctccaaagc caaagggcag   1980

ccccgagaac cacaggtgta caccctgccc ccatcccggg atgagctgac caagaaccag   2040

gtcagcctga cctgcctggt caaaggcttc tatcccagcg acatcgccgt ggagtgggag   2100

agcaatgggc agccggagaa caactacaag accacgcctc ccgtgctgga ctccgacggc   2160

tccttcttcc tctacagcaa gctcaccgtg gacaagagca ggtggcagca ggggaacgtc   2220

ttctcatgct ccgtgatgca tgaggctctg cacaaccact acacgcagaa gagcctctcc   2280

ctgtctccgg gtaaatga                                                 2298
```

<210> SEQ ID NO 41
<211> LENGTH: 1977
<212> TYPE: DNA
<213> ORGANISM: Artificial
<220> FEATURE:
<223> OTHER INFORMATION: Nucleotide sequence of fused protein

<400> SEQUENCE: 41

```
ggtagaccat tcgtagagat gtacagtgaa atccccgaaa ttatacacat gactgaagga     60

agggagctcg tcattccctg ccgggttacg tcacctaaca tcactgttac tttaaaaaag    120

tttccacttg acactttgat ccctgatgga aaacgcataa tctgggacag tagaaagggc    180

ttcatcatat caaatgcaac gtacaaagaa atagggcttc tgacctgtga agcaacagtc    240

aatgggcatt tgtataagac aaactatctc acacatcgac aaaccaatac aatcatagat    300

gtggttctga gtccgtctca tggaattgaa ctatctgttg gagaaaagct tgtcttaaat    360

tgtacagcaa gaactgaact aaatgtgggg attgacttca actgggaata cccttcttcg    420

aagcatcagc ataagaaact tgtaaaccga gacctaaaaa cccagtctgg gagtgagatg    480

aagaaatttt tgagcacctt aactatagat ggtgtaaccc ggagtgacca aggattgtac    540

acctgtgcag catccagtgg gctgatgacc aagaagaaca gcacatttgt cagggtccat    600

gaaaaaccta accccgtagc tccatattgg acatccccag aaaagatgga aaagaaattg    660

catgcagtgc cggctgccaa gacagtgaag ttcaaatgcc cttccagtgg gaccccaaac    720

cccacactgc gctggttgaa aaatggcaaa gaattcaaac ctgaccacag aattggaggc    780

tacaaggtcc gttatgccac ctggagcatc ataatggact ctgtggtgcc ctctgacaag    840

ggcaactaca cctgcattgt ggagaatgag tacggcagca tcaaccacac ataccagctg    900

gatgtcgtgg agcggtcccc tcaccggccc atcctgcaag cagggttgcc cgccaacaaa    960

acagtggccc tgggtagcaa cgtggagttc atgtgtaagg tgtacagtga cccgcagccg   1020

cacatccagt ggctaaagca catcgaggtg aatgggagca agattggccc agacaacctg   1080

ccttatgtcc agatcttgaa gactgctgga gttaatacca ccgacaaaga gatggaggtg   1140

cttcacttaa gaaatgtctc ctttgaggac gcaggggagt atacgtgctt ggcgggtaac   1200

tctatcggac tctcccatca ctctgcatgg ttgaccgttc tggaagccct ggaagagagg   1260

ccggcagtga tgacctcgcc cctgtacctg gaggacaaaa ctcacacatg cccaccgtgc   1320

ccagcacctg aactcctggg gggaccgtca gtcttcctct tccccccaaa acccaaggac   1380

accctcatga tctcccggac ccctgaggtc acatgcgtgg tggtggacgt gagccacgaa   1440

gaccctgagg tcaagttcaa ctggtacgtg gacggcgtgg aggtgcataa tgccaagaca   1500

aagccgcggg aggagcagta caacagcacg taccgtgtgg tcagcgtcct caccgtcctg   1560

caccaggact ggctgaatgg caaggagtac aagtgcaagg tctccaacaa agccctccca   1620

gcccccatcg agaaaaccat ctccaaagcc aaagggcagc cccgagaacc acaggtgtac   1680
```

accctgcccc catcccggga tgagctgacc aagaaccagg tcagcctgac ctgcctggtc 1740
aaaggcttct atcccagcga catcgccgtg gagtgggaga gcaatgggca gccggagaac 1800
aactacaaga ccacgcctcc cgtgctggac tccgacggct ccttcttcct ctacagcaag 1860
ctcaccgtgg acaagagcag gtggcagcag gggaacgtct tctcatgctc cgtgatgcat 1920
gaggctctgc acaaccacta cacgcagaag agcctctccc tgtctccggg taaatga 1977

<210> SEQ ID NO 42
<211> LENGTH: 30
<212> TYPE: DNA
<213> ORGANISM: artificial
<220> FEATURE:
<223> OTHER INFORMATION: synthetic primer

<400> SEQUENCE: 42
gttttgtcct ccaggtacag gggcgaggtc 30

<210> SEQ ID NO 43
<211> LENGTH: 30
<212> TYPE: DNA
<213> ORGANISM: Artificial
<220> FEATURE:
<223> OTHER INFORMATION: synthetic primer

<400> SEQUENCE: 43
ctgtacctgg aggacaaaac tcacacatgc 30

<210> SEQ ID NO 44
<211> LENGTH: 30
<212> TYPE: DNA
<213> ORGANISM: Artificial
<220> FEATURE:
<223> OTHER INFORMATION: synthetic primer

<400> SEQUENCE: 44
gatatctgca gtcatttacc cggagacagg 30

<210> SEQ ID NO 45
<211> LENGTH: 32
<212> TYPE: DNA
<213> ORGANISM: artificial
<220> FEATURE:
<223> OTHER INFORMATION: synthetic primer

<400> SEQUENCE: 45
atagttccgg aggtagacca ttcgtagaga tg 32

<210> SEQ ID NO 46
<211> LENGTH: 40
<212> TYPE: DNA
<213> ORGANISM: artificial
<220> FEATURE:
<223> OTHER INFORMATION: synthetic primer

<400> SEQUENCE: 46
cctgtgatgc gggtgcgatt tttttcatca gggtaactcc 40

<210> SEQ ID NO 47
<211> LENGTH: 30
<212> TYPE: DNA
<213> ORGANISM: artificial
<220> FEATURE:
<223> OTHER INFORMATION: synthetic primer

<400> SEQUENCE: 47
ctgatgaaaa aaatcgcacc cgcatcacag 30

<210> SEQ ID NO 48
<211> LENGTH: 30
<212> TYPE: DNA
<213> ORGANISM: artificial
<220> FEATURE:
<223> OTHER INFORMATION: synthetic primer

<400> SEQUENCE: 48
tttttcatca gggtaactcc aggtcatttg 30

<210> SEQ ID NO 49
<211> LENGTH: 42
<212> TYPE: DNA
<213> ORGANISM: artificial
<220> FEATURE:
<223> OTHER INFORMATION: synthetic primer

<400> SEQUENCE: 49
ggagttaccc tgatgaaaaa ccagaaaaga tggaaaagaa at 42

<210> SEQ ID NO 50
<211> LENGTH: 58
<212> TYPE: DNA
<213> ORGANISM: artificial
<220> FEATURE:
<223> OTHER INFORMATION: synthetic primer

<400> SEQUENCE: 50
accgccagag ccacctccgc ctgaaccgcc accacctttt tcatcagggt aactccag 58

<210> SEQ ID NO 51
<211> LENGTH: 55
<212> TYPE: DNA
<213> ORGANISM: artificial
<220> FEATURE:
<223> OTHER INFORMATION: synthetic primer

<400> SEQUENCE: 51
aggcggaggt ggctctggcg gtggcggatc cccagaaaag atggaaaaga aattg 55

<210> SEQ ID NO 52
<211> LENGTH: 36
<212> TYPE: DNA
<213> ORGANISM: artificial
<220> FEATURE:
<223> OTHER INFORMATION: synthetic primer

<400> SEQUENCE: 52
tagttccgga agcaaattaa aagatcctga actgag 36

<210> SEQ ID NO 53
<211> LENGTH: 42
<212> TYPE: DNA
<213> ORGANISM: artificial
<220> FEATURE:
<223> OTHER INFORMATION: synthetic primer

<400> SEQUENCE: 53
atctctacga aaggtctacc tgtatcacta ataaatatat ag 42

<210> SEQ ID NO 54
<211> LENGTH: 22

-continued

<212> TYPE: DNA
<213> ORGANISM: artificial
<220> FEATURE:
<223> OTHER INFORMATION: synthetic primer

<400> SEQUENCE: 54
ggtagacctt tcgtagagat gt 22

<210> SEQ ID NO 55
<211> LENGTH: 21
<212> TYPE: DNA
<213> ORGANISM: artificial
<220> FEATURE:
<223> OTHER INFORMATION: synthetic primer

<400> SEQUENCE: 55
aggtttttca tggaccctga c 21

<210> SEQ ID NO 56
<211> LENGTH: 45
<212> TYPE: DNA
<213> ORGANISM: artificial
<220> FEATURE:
<223> OTHER INFORMATION: synthetic primer

<400> SEQUENCE: 56
tcagggtcca tgaaaaacct ccagaaaaga tggaaaagaa attgc 45

<210> SEQ ID NO 57
<211> LENGTH: 43
<212> TYPE: DNA
<213> ORGANISM: artificial
<220> FEATURE:
<223> OTHER INFORMATION: synthetic primer

<400> SEQUENCE: 57
tcagggtcca tgaaaaacct aaaaatcgca cccgcatcac agg 43

<210> SEQ ID NO 58
<211> LENGTH: 43
<212> TYPE: DNA
<213> ORGANISM: artificial
<220> FEATURE:
<223> OTHER INFORMATION: synthetic primer

<400> SEQUENCE: 58
gtcagggtcc atgaaaaacc taggccgtcc ccgaccttgc ctg 43

<210> SEQ ID NO 59
<211> LENGTH: 41
<212> TYPE: DNA
<213> ORGANISM: artificial
<220> FEATURE:
<223> OTHER INFORMATION: synthetic primer

<400> SEQUENCE: 59
cctgtgatgc gggtgcgatt aggtttttca tggaccctga c 41

<210> SEQ ID NO 60
<211> LENGTH: 36
<212> TYPE: DNA
<213> ORGANISM: Artificial
<220> FEATURE:
<223> OTHER INFORMATION: synthetic primer

<400> SEQUENCE: 60

-continued ctccggcctc tatgcttccg taaccagcag cccctc 36

<210> SEQ ID NO 61
<211> LENGTH: 36
<212> TYPE: DNA
<213> ORGANISM: artificial
<220> FEATURE:
<223> OTHER INFORMATION: synthetic primer

<400> SEQUENCE: 61
gaggggctgc tggttacgga agcatagagg ccggag 36

<210> SEQ ID NO 62
<211> LENGTH: 41
<212> TYPE: DNA
<213> ORGANISM: artificial
<220> FEATURE:
<223> OTHER INFORMATION: synthetic primer

<400> SEQUENCE: 62
tcagggtcca tgaaaaacct tcgggcagtg acaccaccta c 41

<210> SEQ ID NO 63
<211> LENGTH: 41
<212> TYPE: DNA
<213> ORGANISM: artificial
<220> FEATURE:
<223> OTHER INFORMATION: synthetic primer

<400> SEQUENCE: 63
tcagggtcca tgaaaaacct aaccccgtag ctccatattg g 41

<210> SEQ ID NO 64
<211> LENGTH: 36
<212> TYPE: DNA
<213> ORGANISM: artificial
<220> FEATURE:
<223> OTHER INFORMATION: synthetic primer

<400> SEQUENCE: 64
ctagctccgg accagaaaag atggaaaaga aattgc 36

<210> SEQ ID NO 65
<211> LENGTH: 42
<212> TYPE: DNA
<213> ORGANISM: artificial
<220> FEATURE:
<223> OTHER INFORMATION: synthetic primer

<400> SEQUENCE: 65
tcaggatctt ttaattttga ctccaggtac aggggcgagg tc 42

<210> SEQ ID NO 66
<211> LENGTH: 24
<212> TYPE: DNA
<213> ORGANISM: artificial
<220> FEATURE:
<223> OTHER INFORMATION: synthetic primer

<400> SEQUENCE: 66
tcaaaattaa aagatcctga actg 24

<210> SEQ ID NO 67
<211> LENGTH: 42
<212> TYPE: DNA
<213> ORGANISM: Artificial

<220> FEATURE:
<223> OTHER INFORMATION: synthetic primer

<400> SEQUENCE: 67
tgggcatgtg tgagttttgt caggtttttc atggaccctg ac 42

<210> SEQ ID NO 68
<211> LENGTH: 32
<212> TYPE: DNA
<213> ORGANISM: artificial
<220> FEATURE:
<223> OTHER INFORMATION: synthetic primer

<400> SEQUENCE: 68
tagttccgga aaaaatcgca cccgcatcac ag 32

<210> SEQ ID NO 69
<211> LENGTH: 32
<212> TYPE: DNA
<213> ORGANISM: artificial
<220> FEATURE:
<223> OTHER INFORMATION: synthetic primer

<400> SEQUENCE: 69
tagttccgga aaacctaacc ccgtagctcc at 32

<210> SEQ ID NO 70
<211> LENGTH: 23
<212> TYPE: DNA
<213> ORGANISM: Artificial
<220> FEATURE:
<223> OTHER INFORMATION: synthetic primer

<400> SEQUENCE: 70
gacaaaactc acacatgccc acc 23

<210> SEQ ID NO 71
<211> LENGTH: 455
<212> TYPE: PRT
<213> ORGANISM: Artificial sequence
<220> FEATURE:
<223> OTHER INFORMATION: 26# fused protein

<400> SEQUENCE: 71

```
Asn Pro Val Ala Pro Tyr Trp Thr Ser Pro Glu Lys Met Glu Lys Lys
1               5                   10                  15

Leu His Ala Val Pro Ala Ala Lys Thr Val Lys Phe Lys Cys Pro Ser
            20                  25                  30

Ser Gly Thr Pro Asn Pro Thr Leu Arg Trp Leu Lys Asn Gly Lys Glu
        35                  40                  45

Phe Lys Pro Asp His Arg Ile Gly Gly Tyr Lys Val Arg Tyr Ala Thr
    50                  55                  60

Trp Ser Ile Ile Met Asp Ser Val Val Pro Ser Asp Lys Gly Asn Tyr
65                  70                  75                  80

Thr Cys Ile Val Glu Asn Glu Tyr Gly Ser Ile Asn His Thr Tyr Gln
                85                  90                  95

Leu Asp Val Val Glu Arg Ser Pro His Arg Pro Ile Leu Gln Ala Gly
            100                 105                 110

Leu Pro Ala Asn Lys Thr Val Ala Leu Gly Ser Asn Val Glu Phe Met
        115                 120                 125

Cys Lys Val Tyr Ser Asp Pro Gln Pro His Ile Gln Trp Leu Lys His
    130                 135                 140
```

```
Ile Glu Val Asn Gly Ser Lys Ile Gly Pro Asp Asn Leu Pro Tyr Val
145                 150                 155                 160

Gln Ile Leu Lys Thr Ala Gly Val Asn Thr Thr Asp Lys Glu Met Glu
                165                 170                 175

Val Leu His Leu Arg Asn Val Ser Phe Glu Asp Ala Gly Glu Tyr Thr
            180                 185                 190

Cys Leu Ala Gly Asn Ser Ile Gly Leu Ser His His Ser Ala Trp Leu
        195                 200                 205

Thr Val Leu Glu Ala Leu Glu Glu Arg Pro Ala Val Met Thr Ser Pro
    210                 215                 220

Leu Tyr Leu Glu Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 72
<211> LENGTH: 1374
<212> TYPE: DNA
<213> ORGANISM: Artificial sequence
<220> FEATURE:
<223> OTHER INFORMATION: Nucleotide sequence of 26# fused protein

<400> SEQUENCE: 72

```
aaacctaacc ccgtagctcc atattggaca tccccagaaa agatggaaaa gaaattgcat      60

gcagtgccgg ctgccaagac agtgaagttc aaatgccctt ccagtgggac cccaaacccc     120

acactgcgct ggttgaaaaa tggcaaagaa ttcaaacctg accacagaat tggaggctac     180

aaggtccgtt atgccacctg gagcatcata atggactctg tggtgccctc tgacaagggc     240
```

-continued

```
aactacacct gcattgtgga gaatgagtac ggcagcatca accacacata ccagctggat    300

gtcgtggagc ggtcccctca ccggcccatc ctgcaagcag ggttgcccgc caacaaaaca    360

gtggccctgg gtagcaacgt ggagttcatg tgtaaggtgt acagtgaccc gcagccgcac    420

atccagtggc taaagcacat cgaggtgaat gggagcaaga ttggcccaga caacctgcct    480

tatgtccaga tcttgaagac tgctggagtt aataccaccg acaaagagat ggaggtgctt    540

cacttaagaa atgtctcctt tgaggacgca ggggagtata cgtgcttggc gggtaactct    600

atcggactct cccatcactc tgcatggttg accgttctgg aagccctgga agagaggccg    660

gcagtgatga cctcgcccct gtacctggag gacaaaactc acacatgccc accgtgccca    720

gcacctgaac tcctgggggg accgtcagtc ttcctcttcc ccccaaaacc caaggacacc    780

ctcatgatct cccggacccc tgaggtcaca tgcgtggtgg tggacgtgag ccacgaagac    840

cctgaggtca agttcaactg gtacgtggac ggcgtggagg tgcataatgc caagacaaag    900

ccgcgggagg agcagtacaa cagcacgtac cgtgtggtca gcgtcctcac cgtcctgcac    960

caggactggc tgaatggcaa ggagtacaag tgcaaggtct ccaacaaagc cctcccagcc   1020

cccatcgaga aaaccatctc caaagccaaa gggcagcccc gagaaccaca ggtgtacacc   1080

ctgcccccat cccgggatga gctgaccaag aaccaggtca gcctgacctg cctggtcaaa   1140

ggcttctatc ccagcgacat cgccgtggag tgggagagca atgggcagcc ggagaacaac   1200

tacaagacca cgcctcccgt gctggactcc gacggctcct tcttcctcta cagcaagctc   1260

accgtggaca agagcaggtg gcagcagggg aacgtcttct catgctccgt gatgcatgag   1320

gctctgcaca accactacac gcagaagagc ctctccctgt ctccgggtaa atga         1374


<210> SEQ ID NO 73
<211> LENGTH: 32
<212> TYPE: DNA
<213> ORGANISM: artificial sequence
<220> FEATURE:
<223> OTHER INFORMATION: 26# Fw

<400> SEQUENCE: 73

tagttccgga aaacctaacc ccgtagctcc at                                    32


<210> SEQ ID NO 74
<211> LENGTH: 30
<212> TYPE: DNA
<213> ORGANISM: Artificial sequence
<220> FEATURE:
<223> OTHER INFORMATION: 26# Rev

<400> SEQUENCE: 74

gttttgtcct ccaggtacag gggcgaggtc                                       30


<210> SEQ ID NO 75
<211> LENGTH: 43
<212> TYPE: DNA
<213> ORGANISM: Artificial sequence
<220> FEATURE:
<223> OTHER INFORMATION: 9#-VEGFR1D2 downstream primer

<400> SEQUENCE: 75

catgagacgg actcagaacc acatctatga ttgtattggt ttg                        43


<210> SEQ ID NO 76
<211> LENGTH: 43
<212> TYPE: DNA
<213> ORGANISM: Artificial sequence
```

-continued

```
<220> FEATURE:
<223> OTHER INFORMATION: 9#-VEGFR2D3 upstream primer

<400> SEQUENCE: 76

caaaccaata caatcataga tgtggttctg agtccgtctc atg                43
```